US008703961B2

(12) United States Patent
Heinrich et al.

(10) Patent No.: US 8,703,961 B2
(45) Date of Patent: Apr. 22, 2014

(54) THIAZOLE DERIVATIVES FOR THE TREATMENT OF DISEASES SUCH AS CANCER

(75) Inventors: Timo Heinrich, Gross-Umstadt (DE); Hannes Koolman, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 13/515,537

(22) PCT Filed: Nov. 9, 2010

(86) PCT No.: PCT/EP2010/006822
§ 371 (c)(1),
(2), (4) Date: Jun. 13, 2012

(87) PCT Pub. No.: WO2011/072779
PCT Pub. Date: Jun. 23, 2011

(65) Prior Publication Data
US 2012/0252759 A1  Oct. 4, 2012

(30) Foreign Application Priority Data
Dec. 14, 2009  (DE) .................. 10 2009 058 280

(51) Int. Cl.
*A61K 31/429* (2006.01)
*C07D 513/04* (2006.01)
(52) U.S. Cl.
CPC .................................. *C07D 513/04* (2013.01)
USPC ........... 548/153; 544/124; 544/134; 544/331; 544/364; 546/113; 546/270.1; 546/270.4; 548/110; 548/181; 548/196; 514/234.2; 514/236.8; 514/253.1; 514/275; 514/300; 514/338; 514/342; 514/367; 514/371
(58) Field of Classification Search
USPC ................................. 548/153, 196
See application file for complete search history.

(56) References Cited

U.S. PATENT DOCUMENTS

| | | | |
|---|---|---|---|
| 4,528,291 A | | 7/1985 | Witkowski et al. |
| 4,946,855 A | * | 8/1990 | Yoshinaga et al. ............ 514/371 |
| 8,153,814 B2 | * | 4/2012 | Beaudoin et al. ............ 548/190 |
| 2002/0049215 A1 | | 4/2002 | Chong et al. |
| 2005/0193502 A1 | * | 9/2005 | Murphy et al. .................. 8/405 |
| 2006/0003968 A1 | | 1/2006 | Green et al. |
| 2009/0275592 A1 | | 11/2009 | Zeng et al. |

FOREIGN PATENT DOCUMENTS

| | | |
|---|---|---|
| EP | 0 097 323 | 1/1984 |
| EP | 0 321 115 | 6/1989 |
| WO | WO-03 027085 | 4/2003 |
| WO | WO-2004 041813 | 5/2004 |
| WO | WO-2005 077324 | 8/2005 |
| WO | WO-2006 119146 | 11/2006 |
| WO | WO-2009 011880 | 1/2009 |
| WO | WO-2010 003133 | 1/2010 |

OTHER PUBLICATIONS

Koolman et al., Synthesis, Sep. 2010, No. 18, pp. 3152-3162.*
South, Journal of Heterocyclic Chemistry, (1991), 28(4), pp. 1003-1011.*
Golub et al., Science, vol. 286, Oct. 15, 1999, pp. 531-537.*
Aikawa, Y. et al., "Roles of HIPK1 and HIPK2 in AML1- and p300-dependent transcription, hematopoiesis and blood vessel formation," The EMBO Journal, 2006, vol. 25, No. 17, pp. 3955-3965.
Antonio, C. H. et al., "Aurora kinase inhibitors in preclinical and clinical testing," Expert Opin. Investig. Drugs., 2009, vol. 18, No. 4, pp. 379-398.
Athmani, S. et al., "Azoles. Part 9.[1] Synthesis of derivatives of thieno [2,3-d]thiazoles, 4H-Pyrrolo-[2,3-d]thiazoles, 2H-Pyrazole[3,4-d]thiazole and Isoxazolo[3,4-d]thiazole from Thiazolidine-2,4-dione," J. Chem. Soc. Perkin Trans., 1992, vol. 16, pp. 973-977.
Boss, D. S. et al., "Clinical Experience with Aurora Kinase Inhibitors: A Review," The Oncologist, 2009, vol. 14, pp. 780-793.
Buolamwini, J. K., "Cell cycle molecular targets in novel anticancer drug discovery," Current Pharmaceutical Design, 2000, vol. 6, pp. 379-392.
Daouti, S. et al., "Characterization of a Novel Mitogen-activated protein inhibitor with a unique mechanism of action for cancer therapy," Cancer Research, 2009, vol. 69.
Dekhtyar, M. L. et al., "Approximation of basically and absorption region in large arrays of polymethine dyes with heterocyclic end groups," Dyes and Pigments, 2007, vol. 74, pp. 744-748.
Ferrara, N., "Vascular Endothelial Growth Factor: Basic Science and Clinical progress," Endocrine Reviews, 2004, vol. 25, No. 4, pp. 581-611.
Garuti, L. et al., "Small Molecule Aurora Kinase Inhibitors," Current Medicinal Chemistry, 2009, vol. 16, pp. 1949-1963.
Grehn, L. et al., "The Synthesis and $^{13}$C NMR Spectra of Pyrrolothiazoles and their Precursors. Bromine-induced cyclization of pyrrolylthioureas," Chemica Scripta, 1978, vol. 13, pp. 78-95.
Herman-Antosiewicz, A. et al., "Checkpoint Kinase 1 Regulates Diallyl Trisulfide-induced Mitotic Arrest in Human Prostate Cancer Cells," The Journal of Biological Chemistry, vol. 280, No. 31, pp. 28519-28528, 2005.
International Search Report for PCT/EP2010/006822 dated Jan. 31, 2011.
Karaman, M. W. et al., "A quantitive analysis of kinase inhibitor selectivity," Nature Biotechnology, Jan. 2008, vol. 26, No. 1, pp. 127-132.
Kato, T. et al., "Isolation of a Novel human gene, MARKL1, Homologous to Mark3 and its Involvement in Hepatocellular Carcinogenesis1," Neoplasia, 2001, vol. 3, No. 1, pp. 4-9.
Kusakai, G. et al., "Strong Association of ARK5 with Tumor Invasion and Metastasis," J. Exp. Clin. Cancer Res., 2004, vol. 23, No. 2, pp. 263-268.

(Continued)

*Primary Examiner* — Laura L. Stockton
(74) *Attorney, Agent, or Firm* — Millen, White, Zelano & Branigan, P.C.

(57) ABSTRACT

Compounds of the formula Ia and Ib, in which $R^1$, $R^{1'}$, $R^2$, $R^3$, $R^5$, $R^6$ and $R^7$ have the meanings indicated in claim 1, are kinase inhibitors and can be employed, inter alia, for the treatment of tumours.

13 Claims, No Drawings

(56) References Cited

OTHER PUBLICATIONS

Lapenna, S. et al., "Cell cycle kinases as therapeutic targets for cancer," Nature Reviews, Jul. 2009, vol. 8, pp. 547-566.

Mohamed, A. A. et al., "Substituent effect on the amino-imino tautomerism of aminothiazoles," Journal of Molecular Structure: THEOCHEM, 2008, vol. 849, pp. 52-61.

Pollard, J. R. et al., "Discovery and Development of Aurora Kinase Inhibitors as Anticancer Agents," Journal of Medicinal Chemstry, May 14, 2009, vol. 52, No. 9, pp. 2629-2651.

Schmidt, A. et al., "Rho GTPases regulate PRK2/PKN2 to control entry into mitosis and exit from cytokinesis," The EMBO Journal, 2007, vol. 26, No. 6, pp. 1624-1636.

Shafiee, A. et al., "Selenium Heterocycles. XXVIII (I). Synthesis of Pyrrolo[3,2-d]selenazole and Pyrrolo[3,2-d]thiazole. Two Novel Heterocycles," J. Heterocyclic Chem, 1979, vo. 16, pp. 1563-1566.

Shukri, J. et al., "Neue Sulfathiazole," Wiss. Z. Univ. Halle XXIII, 1984, pp. 91-93, XP002614789.

Suzuki, A. et al., "ARK5 suppresses the cell death induced by nutrient starvation and death receptors via inhibition of caspase 8 activation, but not by chemotherapeutic agents or UV irradiation," Oncogene, 2003, vol. 22, pp. 6177-6182.

Suzuki, A. et al., "Identification of a Novel Protein Kinase Mediating Akt Survival Signaling to ATM Protein," The Journal of Biology Chemistry, vol. 278, No. 1, pp. 48-53, 2003.

Tverdokhlebov, A. V. et al., "Pyrrolo[2,1-b]Thiazoles," Heterocyces, 2007, vol. 71, No. 4, pp. 761-798.

Wang, X. et al., "p53-Dependent Chk1 Phosphorylation is required for Maintenance of prolonged G2 Arrest," Radiation Research, 2007, vol. 168, pp. 706-715.

Wong, C C. et al., "Rho-kinase 2 is frequently overexpressed in hepatocellular carcinoma and involved in tumor invation," Hepatology, 2009, vol. 49, pp. 1583-1594.

Diener, H. et al., "Mechanism of azo coupling reactions. Part 34. 1 Reactivity of five-membered ring heteroaromatic diazonium ions," Cancer J. Chem., 1986, vol. 64, pp. 1102-1107.

\* cited by examiner

THIAZOLE DERIVATIVES FOR THE TREATMENT OF DISEASES SUCH AS CANCER

BACKGROUND OF THE INVENTION

The invention had the object of finding novel compounds having valuable properties, in particular those which can be used for the preparation of medicaments.

One of the principal mechanisms by which cellular regulation is effected is through the transduction of extracellular signals across the membrane that in turn modulate biochemical pathways within the cell. Protein phosphorylation represents one course by which intracellular signals are propagated from molecule to molecule resulting finally in a cellular response. These signal transduction cascades are highly regulated and often overlap, as is evident from the existence of many protein kinases as well as phosphatases. Phosphorylation of proteins occurs predominantly at serine, threonine or tyrosine residues, and protein kinases have therefore been classified by their specificity of phosphorylation site, i.e. serine/threonine kinases and tyrosine kinases. Since phosphorylation is such a ubiquitous process within cells and since cellular phenotypes are largely influenced by the activity of these pathways, it is currently believed that a number of disease states and/or diseases are attributable to either aberrant activation or functional mutations in the molecular components of kinase cascades. Consequently, considerable attention has been devoted to the characterisation of these proteins and compounds that are able to modulate their activity (for a review see: Weinstein-Oppenheimer et al. Pharma. &. Therap., 2000, 88, 229-279).

The present invention relates to compounds and to the use of compounds in which the inhibition, regulation and/or modulation of signal transduction by protein kinases, in particular tyrosine kinases and/or serine/threonine kinases, plays a role, furthermore to pharmaceutical compositions which comprise these compounds, and to the use of the compounds for the treatment of kinase-induced diseases.

In particular, the present invention relates to compounds and to the use of compounds in which the inhibition, regulation and/or modulation of signal transduction by kinases plays a role, in particular the protein kinases NUAK1, also known as ARKS, MAPK (MAP2K1, MAP4K2, MAP3K11), MARK3, ROCK2, also known as Rho kinase 2, CHEK1, also known as CHK1, CDK2, PKN2, KDR, also known as VEGFR, HIPK1 and AURORA.

MAPxKy (Mitogen-activated Protein (MAP) Kinase

The protein encoded by this gene is a member of the dual-specific protein kinase family which functions as a mitogen-activated protein (MAP) kinase. MAP kinases, also described as extracellular signal-regulated kinases (ERKs), function as integration point for various biochemical signals. MAP2K1 is located in front of other MAP kinases in the signal cascade and stimulates the enzymatic activity thereof as a function of many extra- and intracellular signals. As an essential component of the MAP kinase signal transduction pathway, MAP2K1 is involved in many cellular processes, such as proliferation, differentiation, transcription regulation and cell development.

Similar Considerations Apply to Other MAPKs.

The compound RO-4927350, a thiazole derivative, has been described by K. Kolinsky et al. as MEK inhibitor for the specific inhibition of the MAPK signal transduction cascade in Cancer Res. 2009; 69: 1924 ff., where the compound has an antitumour activity in vivo.

T. Kato et al. in Neoplasia 2001; 3 (1): 4-9, describe MARK3 (homologous to MARKL1) as potential target for the treatment of hepatocellular carcinogenesis.

CHEK1

Studies confirm that CHEK1 inhibition increases the cytotoxicity of DNA-damaging agents (Xiao Z, Chen Z, Gunasekera A H, et al. Chk1 mediates S and G2 arrests through Cdc25A degradation in response to DNA-damaging agents, J. Biol. Chem. 2003; 278: 21767-73;

Xiao D, Herman-Antosiewicz A, Antosiewicz J, et al. Diallyl trisulfide-induced G(2)-M phase cell cycle arrest in human prostate cancer cells is caused by reactive oxygen species-dependent destruction and hyperphosphorylation of Cdc 25 C, Oncogene 2005; 24: 6256-68;

Zhao B, Bower M J, McDevitt P J, et al. Structural basis for Chk1 inhibition by UCN-01, J. Biol. Chem. 2002; 277: 46609-15;

Maude S L, Enders G H. Cdk inhibition in human cells compromises chk1 function and activates a DNA damage response. Cancer Res. 2005; 65: 780-6.)
and the expression of CHEK1 is part of the defense mechanism of the cell for avoiding the toxicity of DNA damage.

ROCK2

ROCK2 is a serine/threonine kinase which is activated by association with RhoGTP, which results in phosphorylation of a multiplicity of substrates and ultimately results in stabilisation of filamentous actin and an increase in the activity of myosine ATPase. This in turn causes the formation of contractile actin-myosine units (stress fibres) and integrin-containing focal adhesions. Through the modulation of actin-myosine contractility, ROCK2 has a significant influence on the regulation of cell morphology, cell mobility and cell adhesion. C. Chak-Lui Wong et al. in Hepatology 2009; 49 (5): 1583-94, describe that the inhibition of Rho kinases 1 and 2 (ROCK1 and ROCK2) can be utilised for the treatment of cancer diseases. Thus, ROCK2 plays a significant role in the growth of hepatocellular carcinomas. X. Q. Wang et al. in Radiation Res. 2007; 168 (6): 706-15, describe the checkpoint kinase CHK1 as potential target for the treatment of cancer.

NUAK1

The Nuak1 gene encodes for the "NUAK family SNF1-like kinase 1". NUAK1 interacts with USPX9 and ubiquitin C.

The role of NUAK1 (ARK5) as growth or nutrition factor of tumour cells has been described by A. Suzuki et al. in J. Biol. Chem. 2003; 278 (1): 48-53, and in Oncogene 2003; 22: 6177-82.

The inhibition of NUAK1 (ARK5) thus represents a potential possibility for combating cancer

CDK2

The deactivation of CDK2 prevents the phosphorylation of the protein RB1.

The cell is thus unable to leave the G1 phase of the cell cycle, which results in stopping of all cell division.

J. K. Buolamwini in Current Pharmaceutical Design 2009; 6, (4): 379-92, describes the therapeutic potential of CDK (cyclin dependent kinase) inhibitors in the combating of cancer.

A. Schmidt et al. in EMBO J. 2007; 26: 1624-36, describe PRK2/PKN2 as potential target for the treatment of tumour diseases.

N. Ferrara in Endocrine Rev. 2004; 25 (4): 581-611, describes the use VEGF inhibitors for combating cancer.

VEGF and KDR represent a ligand-receptor pair which plays an essential role in the proliferation of vascular endothelial cells and in the formation and sprouting of blood vessels, which are known as vasculogenesis or angiogenesis.

Angiogenesis is characterised by above-average activity of vascular endothelial growth factor (VEGF). VEGF actually consists of a family of ligands (Klagsburn and D'Amore, Cytokine & Growth Factor Rev. 1996; 7: 259-70,). VEGF binds the high-affinity membrane-spanning tyrosine kinase receptor KDR and the related fms tyrosine kinase-1, also known as Flt-1 or vascular endothelial cell growth factor receptor 1 (VEGFR-1). Cell culture and gene knockout experiments indicate that each receptor contributes to different aspects of angiogenesis. KDR mediates the mitogenic function of VEGF, whereas Flt-1 appears to modulate non-mitogenic functions, such as those associated with cellular adhesion. Inhibition of KDR thus modulates the level of mitogenic VEGF activity. In fact, it has been shown that tumour growth is influenced by the antiangiogenic action of VEGF receptor antagonists (Kim et al., Nature 1993; 362: 841-4).

Three PTK (protein tyrosine kinase) receptors for VEGFR have been identified: VEGFR-1 (Flt-1); VEGRF-2 (Flk-1 or KDR) and VEGFR-3 (Flt-4).

The fact that the inhibition of VEGFR (vascular endothelial growth factor receptor 2—KDR) is of importance for tumour therapy has been shown by means of the introduced medicaments sunitinib, sorafenib and vatalanib, which also inhibit VEGFR.

HIPK1

HIPK1, a nuclear protein kinase which is present in increased concentrations in breast cancer cells, serves to phosphorylate various transcription factors, including p53.

It can be assumed that HIPK1 plays a role in cancer and tumorigenesis by regulating p53 and/or the Mdm2 function.

Y. Aikawa et al. in EMBO J. 2006; 25: 3955-65, describe the homeodomain-interacting protein kinases HIPK1, HIPK2 and HIPK3 as potential targets for the treatment of tumour diseases.

R. Copeland et al. in FASEB J. 2008; 22: 1050 ff., describe HIPK1 as target for the treatment of cancer diseases.

HIPK2 (homeodomain interacting protein kinase)

The significantly increased expression of HIPK2 in cervical cancer seems to correlate with the progression of the disease (Eva Krieghoff-Henning javascript:popRef('a1') & Thomas G Hofmann Future Oncology 2008; 4 (6): 751-54).

The role of aurora kinase inhibitors in the treatment of tumours are described by a number of authors:

D. S. Boss et al., The Oncologist 2009; 14: 780-93;

S. Lapenna et al., Nature Rev. Drug Discov. 2009; 8: 547-66; 35

L. Garuti et al., Cur. Med. Chem. 2009; 16, 1949-63;

J. R. Pollard et al., J. Med. Chem. 2009; 52 (9): 2629-51;

C. H. A. Cheung et al., Expert Opin. Investig. Drugs 2009; 18 (4): 379-98.

The present invention therefore relates to the use of the compounds of the formula I for the treatment of diseases or conditions in which inhibition of the activity of protein kinases, in particular the protein kinases NUAK1, also known as ARK5, MAPK (MAP2K1, MAP4K2, MAP3K11), MARK3, ROCK2, also known as Rho kinase 2, CHEK1, also known as CHK1, CDK2, PKN2, KDR, also known as VEGFR, HIPK1 and AURORA, is advantageous.

The synthesis of small compounds which specifically inhibit, regulate and/or modulate signal transduction by tyrosine kinases and/or serine/threonine kinases, in particular the above-mentioned protein kinases, is therefore desirable and an aim of the present invention.

It has been found that the compounds according to the invention and salts thereof have very valuable pharmacological properties while being well tolerated.

The present invention specifically relates to compounds of the formula I which inhibit, regulate and/or modulate signal transduction by protein kinases, to compositions which comprise these compounds, and to processes for the use thereof for the treatment of kinase-induced diseases and complaints, such as angiogenesis, cancer, tumour formation, growth and propagation, arteriosclerosis, ocular diseases, such as age-induced macular degeneration, choroidal neovascularisation and diabetic retinopathy, inflammatory diseases, arthritis, thrombosis, fibrosis, glomerulonephritis, neurodegeneration, psoriasis, restenosis, wound healing, trans-plant rejection, metabolic diseases and diseases of the immune system, also autoimmune diseases, cirrhosis, diabetes and diseases of the blood vessels, also instability and permeability and the like in mammals.

Solid tumours, in particular fast-growing tumours, can be treated with kinase inhibitors. These solid tumours include monocytic leukaemia, brain, urogenital, lymphatic system, stomach, laryngeal and lung carcinoma, including lung adenocarcinoma and small-cell lung carcinoma.

The compounds of the formula Ia and Ib can furthermore be used to provide additive or synergistic effects in certain existing cancer chemotherapies, and/or can be used to restore the efficacy of certain existing cancer chemotherapies and radiotherapies.

It can be shown that the compounds according to the invention have an antiproliferative action in vivo in a xenotransplant tumour model. The compounds according to the invention are administered to a patient having a hyperproliferative disease, for example to inhibit tumour growth, to reduce inflammation associated with a lymphoproliferative disease, to inhibit trans-plant rejection or neurological damage due to tissue repair, etc. The present compounds are suitable for prophylactic or therapeutic purposes. As used herein, the term "treatment" is used to refer to both prevention of diseases and treatment of pre-existing conditions. The prevention of proliferation is achieved by administration of the compounds according to the invention prior to the development of overt disease, for example to prevent the growth of tumours, prevent metastatic growth, diminish restenosis associated with cardiovascular surgery, etc. Alternatively, the compounds are used for the treatment of ongoing diseases by stabilising or improving the clinical symptoms of the patient.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

The susceptibility of a particular cell to treatment with the compounds according to the invention can be determined by in vitro tests. Typically, a culture of the cell is combined with a compound according to the invention at various concentrations for a period of time which is sufficient to allow the active agents to induce cell death or to inhibit migration, usually between about one hour and one week. In vitro testing can be carried out using cultivated cells from a biopsy sample. The viable cells remaining after the treatment are then counted.

The dose varies depending on the specific compound used, the specific disease, the patient status, etc. A therapeutic dose is typically sufficient considerably to reduce the undesired cell population in the target tissue while the viability of the patient is maintained. The treatment is generally continued until a considerable reduction has occurred, for example an at least about 50% reduction in the cell burden, and may be continued until essentially no more undesired cells are detected in the body.

For identification of a signal transduction pathway and for detection of interactions between various signal transduction pathways, various scientists have developed suitable models or model systems, for example cell culture models (for example Khwaja et al., EMBO J. 1997; 16: 2783-93) and models of transgenic animals (for example White et al., Oncogene 2001; 20: 7064-72). For the determination of certain stages in the signal transduction cascade, interacting compounds can be utilised in order to modulate the signal (for example Stephens et al., Biochemical J. 2000; 351: 95-105). The compounds according to the invention can also be used as reagents for testing kinase-dependent signal transduction pathways in animals and/or cell culture models or in the clinical diseases mentioned in this application.

Measurement of the kinase activity is a technique which is well known to the person skilled in the art. Generic test systems for the determination of the kinase activity using substrates, for example histone (for example Alessi et al., FEBS Lett. 1996; 399 (3): 333-8) or the basic myelin protein, are described in the literature (for example Campos-González, R. and Glenney, Jr., J. R. J. Biol. Chem. 1992; 267: 14535).

For the identification of kinase inhibitors, various assay systems are available. In scintillation proximity assay (Sorg et al., J. Biomol. Screen. 2002; 7: 11-19) and flashplate assay, the radioactive phosphorylation of a protein or peptide as substrate with γATP is measured. In the presence of an inhibitory compound, a decreased radioactive signal, or none at all, is detectable. Furthermore, homogeneous time-resolved fluorescence resonance energy transfer (HTR-FRET) and fluorescence polarisation (FP) technologies are suitable as assay methods (Sills et al., J. Biomol. Screen. 2002; 7 (3): 191-214).

Other non-radioactive ELISA assay methods use specific phospho-anti-bodies (phospho-ABs). The phospho-AB binds only the phosphorylated substrate. This binding can be detected by chemiluminescence using a second peroxidase-conjugated anti-sheep antibody (Ross et al. Biochem. J. 2002, 366: 977-981).

There are many diseases associated with deregulation of cellular proliferation and cell death (apoptosis). The conditions of interest include, but are not limited to, the following. The compounds according to the invention are suitable for the treatment of various conditions where there is proliferation and/or migration of smooth muscle cells and/or inflammatory cells into the intimal layer of a vessel, resulting in restricted blood flow through that vessel, for example in the case of neointimal occlusive lesions. Occlusive graft vascular diseases of interest include atherosclerosis, coronary vascular disease after grafting, vein graft stenosis, peri-anastomatic prosthetic restenosis, restenosis after angioplasty or stent placement, and the like.

PRIOR ART

Other heterocyclic compounds have been described by various authors as aurora kinase inhibitors for combating cancer:

L. Garuti et al., Curr. Med. Chem. 2009; 16: 1949-63;
J. R. Pollard et al., J. Med. Chem. 2009; 52 (9): 2629-51;
C. H. A. Cheung et al., Expert Opin. Investig. Drugs 2009; 18 (4): 379-98.
J. K. Buolamwini in Current Pharmaceutical Design 2009; 6, (4): 379-92, describes other heterocyclic compounds, inter alia a diaminothiazole derivative, as CDK inhibitor.

Thiazolopyrazoles have been described as medicaments in WO 2005/095420.

The synthesis of pyrrolo[2,1-b]thiazoles is described by A. V. Tverkhlebov in Heterocycles 2007; 71: 761-98.

L. Grehn in Chemica Scripta 1978; 13: 78-95, describes processes for the preparation of pyrrolothiazoles.

S. Athmani et al. in J. Chem. Soc. Perkin Trans. 1992; 973-77, describe the synthesis of pyrrolo[2,3-d]thiazoles.

Another synthesis of pyrrolo[3,2-d]thiazoles is described by A. Shafiee et al. in J. Heterocyclic Chem. 1979; 16: 1563-66.

Other heterocyclic compounds are described as dyes by M. L. Dekhtyar in Dyes and Pigments 2007; 74: 744-48.

Other pyrrolothiazoles are disclosed in keratin dye formulations in WO 2005/077324.

SUMMARY OF THE INVENTION

The invention relates to compounds of the formula Ia and Ib

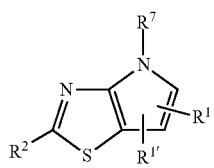

Ia

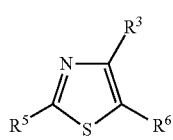

Ib in which
$R^1$ denotes H, $(CH_2)_n Ar$ or $(CH_2)_n Het$,
$R^{1'}$ denotes H or A,
$R^2$ denotes H, A, Hal, $(CH_2)_n Het^1$, $(CH_2)_n Het^3$, —C≡C—Ar, $(CH_2)_n Ar^2$, NHCONHAr, COA, COOH, COOA, COHet$^1$, COAr$^2$, CONH$_2$, CONHA, CONA$_2$, SO$_2$NH$_2$, SO$_2$NHA, S(O)$_m$A, NHCOA, SO$_2$NHA, SO$_2$NA$_2$, SO$_2$NHHet$^1$, SO$_2$NHAr$^2$ or

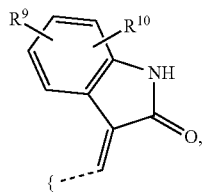

$R^3$ denotes NHCOOA' or NH$_2$,
$R^4$ denotes $(CH_2)_n Ar$, SiA$_3$ or $(CH_2)_n Het^4$,
$R^5$ denotes H, Hal or $(CH_2)_n Het^3$,
$R^6$ denotes H, —C≡C—R$^4$ or Hal,
$R^7$ denotes H, A, Ar or Het$^1$,
Ar denotes phenyl which is unsubstituted or mono-, di- or trisubstituted by Hal, A, OH, OA, CN, NO$_2$, SO$_2$A, COOH, COOA, NH$_2$, NHA, NA$_2$, NHCH$_2$Ar$^1$, CHO, COA, CHO, CONH$_2$, CONHA, CONA$_2$, Het, SO$_2$NH$_2$, SO$_2$NHA, S(O)$_m$A and/or NHCOA, Het denotes a mono- or bicyclic aromatic heterocycle having 1 to 4 N, O and/or S atoms, which may be unsubstituted or mono-, di- or trisubstituted by Hal, A, $NH_2$, NHA, $NA_2$, COOH, COOA, $CONH_2$, CONHA, $CONA_2$, CONHAr, $CONHHet^4$, $S(O)_mA$ and/or $NHCH_2Ar^1$, $Ar^1$ denotes phenyl which is unsubstituted or mono-, di- or trisubstituted by Hal, A, OH and/or OA, $Ar^2$ denotes phenyl which is monosubstituted by NHCONH-$Het^4$, $Het^1$ denotes a mono- or bicyclic aromatic, unsaturated or saturated heterocycle having 1 to 4 N, O and/or S atoms, which may be unsubstituted or mono-, di- or trisubstituted by Hal, A, COOA, $NH_2$, $NHR^8$ and/or $(CH_2)_nHet^2$, $R^8$ denotes H, A, $Ar^1$ or $Het^4$, $R^9$, $R^{10}$ each, independently of one another, denote H or Hal, $R^{11}$ denotes H or A', $Het^2$ denotes a mono- or bicyclic aromatic heterocycle having 1 to 4 N, O and/or S atoms, which may be unsubstituted or mono-, di- or trisubstituted by A, CODA and/or $NH_2$, $Het^3$ denotes a mono- or bicyclic aromatic heterocycle having 1 to 4 N, O and/or S atoms, which may be unsubstituted or mono-, di- or trisubstituted by $NH_2$, $Het^4$ denotes a mono- or bicyclic aromatic, unsaturated or saturated heterocycle having 1 to 4 N, O and/or S atoms, which may be unsubstituted or mono-, di- or trisubstituted by Hal, A, $Ar^1$, $NH_2$, $NHCH_2Ar^1$ and/or =O, A denotes unbranched or branched alkyl having 1-10 C atoms, in which 1-7 H atoms may be replaced by F and/or in which one or two non-adjacent CH and/or $CH_2$ groups may be replaced by O, NH, NA', S, SO, $SO_2$ and/or by CH=CH groups, or cyclic alkyl having 3-7 C atoms, A' denotes unbranched or branched alkyl having 1-4 C atoms, Hal denotes F, Cl, Br or I, m denotes 0, 1 or 2, n denotes 0, 1, 2, 3 or 4, and pharmaceutically usable salts, tautomers and stereoisomers thereof, including mixtures thereof in all ratios.

The compounds of the formula Ib are synthetic precursors in the preparation of compounds of the formula Ia, and, like the compounds of the formula Ia, are potent kinase inhibitors.

Compounds of the formula Ia and Ib are also taken to mean the hydrates and solvates of these compounds, furthermore pharmaceutically usable derivatives.

The invention also relates to the optically active forms (stereoisomers), the enantiomers, the racemates, the diastereomers and the hydrates and solvates of these compounds. The term solvates of the compounds is taken to mean adductions of inert solvent molecules onto the compounds which form owing to their mutual attractive force. solvates are, for example, mono- or dihydrates or alkoxides.

Pharmaceutically usable derivatives are taken to mean, for example, the salts of the compounds according to the invention and also so-called prodrug compounds.

Prodrug derivatives are taken to mean compounds of the formula Ia and Ib which have been modified by means of, for example, alkyl or acyl groups, sugars or oligopeptides and which are rapidly cleaved in the organism to form the effective compounds according to the invention.

These also include biodegradable polymer derivatives of the compounds according to the invention, as described, for example, in Int. J. Pharm. 1995; 115: 61-67.

The expression "effective amount" denotes the amount of a medicament or of a pharmaceutical active ingredient which causes in a tissue, system, animal or human a biological or medical response which is sought or desired, for example, by a researcher or physician.

In addition, the expression "therapeutically effective amount" denotes an amount which, compared with a corresponding subject who has not received this amount, has the following consequence: improved treatment, healing, prevention or elimination of a disease, syndrome, condition, complaint, disorder or side-effects or also the reduction in the advance of a disease, complaint or disorder.

The term "therapeutically effective amount" also encompasses the amounts which are effective for increasing normal physiological function.

The invention also relates to the use of mixtures of the compounds of the formula Ia and Ib, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

The invention relates to the compounds of the formula Ia and Ib and salts thereof and to a process for the preparation of compounds of the formula Ia and Ib and pharmaceutically usable salts, tautomers and stereoisomers thereof, characterised in that a) for the preparation of a compound of the formula Ia',

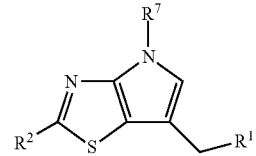

Ia' in which $R^1$ denotes Ar or Het, $R^2$ has the meanings indicated in claim 1, apart from Hal, $R^7$ denotes tert-butyloxycarbonyl, and Ar and Het have the meanings indicated in claim 1, a compound of the formula IIc

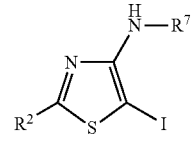

IIc in which $R^2$ has the meaning indicated in claim 1, apart from Hal, $R^7$ denotes tert-butyloxycarbonyl, is reacted with a compound of the formula IIIc

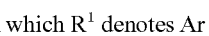

$R^1$—CH=CH—$CH_2$Br    IIIc in which $R^1$ denotes Ar or Het, and Ar and Het have the meanings indicated in claim 1, and the tert-butyloxycarbonyl group is subsequently or simultaneously cleaved off, or b) for the preparation of a compound of the formula Ib',

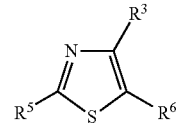

Ib' in which $R^3$ denotes NH—COO-tert-butyl, $R^5$ denotes H or $(CH_2)_nHet^3$, $R^6$ denotes —C≡C—$R^4$ and n, $R^4$ and $Het^3$ have the meanings indicated in claim 1, a compound of the formula IId

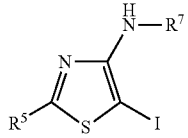

in which
R⁷ denotes tert-butyloxycarbonyl,
R² denotes H or (CH₂)ₙHet³,
and Het³ has the meaning indicated in claim 1,
is reacted with a compound of the formula IIId

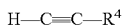

in which R⁴ has the meaning indicated in claim 1,
or
c) for the preparation of a compound of the formula Ib″

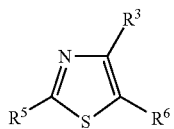

in which
R³ denotes NH—COO-tert-butyl,
R⁵ denotes Cl,
R⁶ denotes —C≡C—R⁴
and
R⁴ has the meaning indicated in claim 1,
a compound of the formula Ib‴,

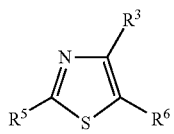

in which
R³ denotes NH—COO-tert-butyl,
R⁵ denotes H,
R⁶ denotes —C≡C—R⁴
and
R⁴ has the meaning indicated in claim 1,
is reacted with N-chlorosuccinimide,
or
d) for the preparation of a compound of the formula Ib′

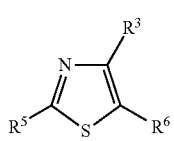

in which
R³ denotes NH—COO-tert-butyl,
R⁵ denotes (CH₂)ₙHet³,
R⁶ denotes —C≡C—R⁴
and
n, R⁴ and Het³ have the meanings indicated in claim 1, a compound of the formula Ib″

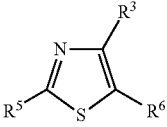

in which
R³ denotes NH—COO-tert-butyl,
R⁵ denotes Cl,
R⁶ denotes —C≡C—R⁴
and
R⁴ has the meaning indicated in claim 1,
is reacted with a compound of the formula IVa

L-(CH₂)ₙR⁵ in which R⁵ denotes Het³,
n and Het³ have the meanings indicated in claim 1,
and L denotes a boronic acid or boronic acid ester radical,
and subsequently or simultaneously the Boc group is cleaved off,
or
e) for the preparation of a compound of the formula Ia″

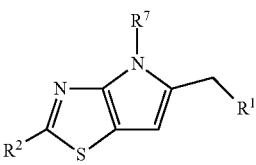

in which
R¹ denotes Ar or Het,
R² denotes H, Cl, (CH₂)ₙHet³
R⁷ denotes H,
and Ar, Het and Het³ have the meanings indicated in claim 1,
a compound of the formula Ib′

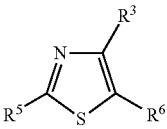

in which
R³ denotes NH—COO-tert-butyl,
R⁵ denotes H, Cl, (CH₂)ₙHet³,
R⁶ denotes —C≡C—R⁴
R⁴ denotes Ar or Het,
and n, Ar, Het, Het³ and R⁴ have the meanings indicated in claim 1,
is heated in the presence of a base,
or
f) for the preparation of a compound of the formula Ia″

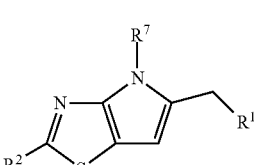

in which
R¹ denotes Ar or Het,
R² denotes Het¹
R⁷ denotes H, a compound of the formula Ia''

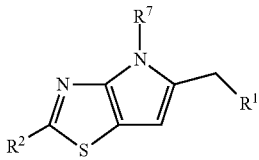

in which
R$^1$ denotes Ar or Het,
R$^2$ denotes Hal
R$^7$ denotes H,
Ar and Het have the meanings indicated in claim 1,
is reacted with a compound of the formula Va Het$^1$-H  Va in which Het$^1$ has the meaning indicated in claim 1,
and/or
a base or acid of the formula Ia or Ib is converted into one of its salts.

Above and below, the radicals R$^1$, R$^{1'}$, R$^2$, R$^3$, R$^5$, R$^6$ and R$^7$ have the meanings indicated for the formulae Ia and Ib, unless expressly indicated otherwise.

For all radicals which occur more than once, their meanings are independent of one another.

A denotes alkyl, is unbranched (linear) or branched, and has 1, 2, 3, 4, 5, 6, 7, 8, 9 or 10 C atoms. A preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethyl-propyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, furthermore preferably, for example, trifluoromethyl.

A very particularly preferably denotes alkyl having 1, 2, 3, 4, 5 or 6 C atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoro-ethyl.

A also denotes unbranched or branched alkyl having 1-10 C atoms, in which 1-7 H atoms may be replaced by OH, F, Cl and/or Br.

A furthermore denotes, for example, 2-hydroxyethyl, 3-hydroxypropyl, 2-methoxyethyl or 3-methoxypropyl.

Cyclic alkyl (cycloalkyl) preferably denotes cyclopropyl, cyclobutyl, cyclo-pentyl, cyclohexyl or cycloheptyl.

A' denotes alkyl, this is unbranched (linear) or branched, and has 1, 2, 3, 4, 5 or 6 C atoms. A' preferably denotes methyl, furthermore ethyl, propyl, iso-propyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, furthermore preferably, for example, trifluoromethyl.

A' very particularly preferably denotes methyl, ethyl, propyl, isopropyl, butyl, isobutyl, sec-butyl, tert-butyl, pentyl, hexyl or trifluoromethyl.

R$^1$ preferably denotes 4-fluorophenyl, benzyl, 3-aminophenyl, 3-(benzylamino)phenyl or 2-aminopyridin-4-yl.
R$^{1'}$ preferably denotes H.
R$^2$ preferably denotes H, Hal, Het$^1$ or —C≡C—Ar.
R$^3$ preferably denotes NHCOOA' or NH$_2$.
R$^5$ preferably denotes H.

R$^6$ preferably denotes H, 4-fluorophenylethynyl, 3-phenyl-prop-1-ynyl, triethyl-silanylethynyl, 3-aminophenylethynyl, 3-benzylaminophenylethynyl, 2-benzyl-aminopyridin-4-yl-ethynyl, pyrrolo[2,3-b]pyridin-5-ylethynyl, Hal, 3-morpholin-4-ylprop-1-ynyl, 3-(1,3-dioxo-1,3-dihydroisoindol-2-yl)prop-1-ynyl or 3-hydroxy-phenylethynyl.

R$^7$ preferably denotes H.

Ar denotes, for example, phenyl, o-, m- or p-tolyl, o-, m- or p-ethylphenyl, o-, m- or p-propylphenyl, o-, m- or p-isopropylphenyl, o-, m- or p-tert-butyl-phenyl, o-, m- or p-hydroxyphenyl, o-, m- or p-nitrophenyl, o-, m- or p-aminophenyl, o-, m- or p-(N-methylamino)phenyl, o-, m- or p-(N-methyl-aminocarbonyl)phenyl, o-, m- or p-acetamidophenyl, o-, m- or p-methoxy-phenyl, o-, m- or p-ethoxyphenyl, o-, m- or p-ethoxycarbonylphenyl, o-, m- or p-(N,N-dimethylamino)phenyl, o-, m- or p-(N,N-dimethylaminocarbonyl)-phenyl, o-, m- or p-(N-ethylamino)phenyl, o-, m- or p-(N,N-diethylamino)-phenyl, o-, m- or p-fluorophenyl, o-, m- or p-bromophenyl, o-, m- or p-chlorophenyl, o-, m- or p-(methylsulfonamido)phenyl, o-, m- or p-(methyl-sulfonyl)phenyl, o-, m- or p-cyanophenyl, o-, m- or p-carboxyphenyl, o-, m- or p-methoxycarbonylphenyl, o-, m- or p-aminosulfonylphenyl, o-, m- or p-(benzylamino)phenyl furthermore preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-nitro-4-chlorophenyl, 3-amino-4-chloro-, 2-amino-3-chloro-, 2-amino-4-chloro-, 2-amino-5-chloro- or 2-amino-6-chlorophenyl, 2-nitro-4-N,N-dimethylamino- or 3-nitro-4-N,N-dimethylaminophenyl, 2,3-diaminophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 3,6-di-chloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-meth-oxyphenyl, 3-chloro-4-acetamidophenyl, 3-fluoro-4-methoxyphenyl, 3-amino-6-methylphenyl, 3-chloro-4-acetamidophenyl or 2,5-dimethyl-4-chlorophenyl.

Ar particularly preferably denotes phenyl which is unsubstituted or mono-, di- or trisubstituted by Hal, A, OH, OA, CN, NO$_2$, SO$_2$A, COOH, COOA, NH$_2$, NHA, NA$_2$, NHCH$_2$Ar$^1$, CHO, COA, CHO, CONH$_2$, CONHA, CONA$_2$, SO$_2$NH$_2$, SO$_2$NHA and/or NHCOA.

Ar very particularly preferably denotes phenyl which is unsubstituted or mono-, di- or trisubstituted by Hal, A, OH, OA, NH$_2$, NHA, NA$_2$ and/or NHCH$_2$Ar$^1$.

Ar$^1$ preferably denotes phenyl.

Irrespective of further substitutions, Het denotes, for example, 2- or 3-furyl, 2- or 3-thienyl, 1-, 2- or 3-pyrrolyl, 1-, 2,4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, further-more preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-iso-indolyl, indazolyl, 1-, 2-, 4- or 5-benzimidazolyl, 1-, 3-, 4-, 5-, 6- or 7-benzo-pyrazolyl, 2-, 4-, 5-, 6- or 7-benzoxazolyl, 3-, 4-, 5-, 6- or 7- benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, pyrrolopyridinyl, purinyl, further preferably 1,3-benzodioxol-5- yl, 1,4-benzodioxan-6-yl, 2,1,3-benzothiadiazol-4-, -5-yl or 2,1,3-benzoxa-diazol-5-yl or dibenzofuranyl.

Het particularly preferably denotes furyl, thienyl, pyrrolyl, imidazolyl, pyrazolyl, oxazolyl, isoxazolyl, thiazolyl, isothiazolyl, pyridyl, pyrimidinyl, triazolyl, tetra-zolyl, oxa-diazolyl, thiadiazolyl, pyridazinyl, pyrazinyl, benzimidazolyl, benzo-triazolyl, quinolinyl, quinoxalinyl, quinazolinyl, pyrrolopyridinyl, purinyl, indolyl or indazolyl, each of which is unsubstituted or mono- or disubstituted by $NH_2$ and/or $NHCH_2Ar^1$.

Irrespective of further substitutions, $Het^1$ denotes, for example, 2- or 3-furyl, 2- or 3-thienyl, 1-, 2- or 3-pyrrolyl, 1-, 2,4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, indazolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7- benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxa-diazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, pyrrolopyridinyl, purinyl, further preferably 1,3-benzodioxol-5-yl, 1,4-benzodioxan-6-yl, 2,1,3-benzothia-diazol-4- or -5-yl, 2,1,3-benzoxadiazol-5-yl, azabicyclo[3.2.1]-octyl or dibenzo-furanyl.

The heterocyclic radicals may also be partially or fully hydrogenated.

Irrespective of further substitutions, $Het^1$ can thus also denote, for example, 2,3-dihydro-2-, -3-, -4- or -5-furyl, 2,5-dihydro-2-, -3-, -4- or 5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, furthermore preferably 2,3-methylenedioxyphenyl, 3,4-methylenedioxyphenyl, 2,3-ethylenedioxy-phenyl, 3,4-ethylenedioxyphenyl, 3,4-(difluoromethylenedioxy)phenyl, 2,3-dihydrobenzofuran-5- or 6-yl, 2,3-(2-oxomethylenedioxy) phenyl or also 3,4-dihydro-2H-1,5-benzodioxepin-6- or -7-yl, furthermore preferably 2,3-dihydrobenzofuranyl, 2,3-dihydro-2-oxofuranyl, 3,4-dihydro-2-oxo-1H-quinazolinyl, 2,3-dihydrobenzoxazolyl, 2-oxo-2,3-dihydrobenzoxazolyl, 2,3-dihydrobenzimidazolyl, 1,3-dihydroindole, 2-oxo-1,3-dihydroindole or 2-oxo-2,3-dihydrobenzimidazolyl.

$Het^1$ particularly preferably denotes piperidinyl, pyrrolidinyl, morpholinyl, piperazinyl, imidazolidinyl, oxazolidinyl, tetrahydropyranyl, thiazolyl, thiophenyl, furanyl, pyrrolyl, oxazolyl, isoxazolyl, oxadiazolyl, pyrazolyl, imidazolyl, triazolyl, thiadiazolyl, pyridazinyl, pyrazinyl, pyridinyl or pyrimidinyl, each of which is unsubstituted or mono- or disubstituted by $NH_2$ and/or $CH_2Het^2$.

Irrespective of further substitutions, $Het^2$ denotes, for example, 2- or 3-furyl, 2- or 3-thienyl, 1-, 2- or 3-pyrrolyl, 1-, 2,4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, indazolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxa-zolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, pyrrolopyridinyl, purinyl, further preferably 1,3-benzodioxol-5-yl, 1,4-benzo-dioxan-6-yl, 2,1,3-benzothiadiazol-4- or -5-yl, 2,1,3-benzoxadiazol-5-yl or dibenzofuranyl.

$Het^2$ particularly preferably denotes furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxa-diazolyl, thiadiazolyl, pyridazinyl, pyrazinyl, benzimidazolyl, benzo-triazolyl, quinolinyl, quinoxalinyl, quinazolinyl, pyrrolopyridinyl, purinyl, indolyl or indazolyl, each of which is unsubstituted or mono- or disubstituted by A and/or $NH_2$.

Irrespective of further substitutions, $Het^3$ denotes, for example, 2- or 3-furyl, 2- or 3-thienyl, 1-, 2- or 3-pyrrolyl, 1-, 2,4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, indazolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7- benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, pyrrolopyridinyl, purinyl, further preferably 1,3-benzodioxol-5-yl, 1,4-benzodioxan-6-yl, 2,1,3-benzothiadiazol-4- or -5-yl, 2,1,3-benzoxadiazol-5-yl or dibenzofuranyl.

$Het^3$ particularly preferably denotes furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxa-diazolyl, thiadiazolyl, pyridazinyl, pyrazinyl, benzimidazolyl, benzo-triazolyl, quinolinyl, quinoxalinyl, quinazolinyl, pyrrolopyridinyl, purinyl, indolyl or indazolyl, each of which is unsubstituted or mono- or disubstituted by A and/or $NH_2$ Irrespective of further substitutions, $Het^4$ denotes, for example, 2- or 3-furyl, 2- or 3-thienyl, 1-, 2- or 3-pyrrolyl, 1-, 2,4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, indazolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7- benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, pyrrolopyridinyl, purinyl, further preferably 1,3-benzodioxol-5-yl, 1,4-benzodioxan-6-yl, 2,1,3-benzothiadiazol-4- or -5-yl, 2,1,3-benzoxadiazol-5-yl, azabicyclo[3.2.1]-octyl or dibenzofuranyl.

The heterocyclic radicals may also be partially or fully hydrogenated. Irrespective of further substitutions, $Het^4$ can thus also denote, for example, 2,3-dihydro-2-, -3-, -4- or -5-furyl, 2,5-dihydro-2-, -3-, -4- or 5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, further preferably 2,3-methylenedioxyphenyl, 3,4-methylenedioxyphenyl, 2,3-ethylenedioxy-phenyl, 3,4-ethylenedioxyphenyl, 3,4-(difluoromethylenedioxy)phenyl, 2,3-dihydrobenzofuran-5- or 6-yl, 2,3-(2-oxomethylenedioxy)phenyl or also 3,4-dihydro-2H-1,5-benzodioxepin-6- or -7-yl, furthermore preferably 2,3-dihydro-benzofuranyl, 2,3-dihydro-2-oxo-furanyl, 3,4-dihydro-2-oxo-1H-quinazolinyl, 2,3-dihydrobenzoxazolyl, 2-oxo-2,3-dihydrobenzoxazolyl, 2,3-dihydrobenz-imidazolyl, 1,3-dihydroindole, 2-oxo-1,3-dihydroindole or 2-oxo-2,3-dihydro-benzimidazolyl.

$Het^4$ particularly preferably denotes piperidinyl, pyrrolidinyl, morpholinyl, piperazinyl, imidazolidinyl, oxazolidinyl, tetrahydropyranyl, dihydroisoindolyl, furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, pyrazinyl, benzimidazolyl, benzotriazolyl, quinolinyl, quinoxalinyl, quinazolinyl, pyrrolopyridinyl, purinyl, indolyl or indazolyl, each of which is unsubstituted or mono- or disubstituted by $NH_2$, $NHCH_2Ar^1$ and/or =O.

Hal preferably denotes F, Cl or Br, but also I, particularly preferably F or Cl; m preferably denotes 1 or 2; n preferably denotes 0, 1, 2 or 3.

Throughout the invention, all radicals which occur more than once may be identical or different, i.e. are independent of one another.

The compounds of the formula Ia and Ib may have one or more chiral centres and can therefore occur in various stereoisomeric forms. The formula Ia and Ib encompasses all these forms.

Accordingly, the invention relates, in particular, to the compounds of the formula Ia and Ib in which at least one of the said radicals has one of the preferred meanings indicated above. Some preferred groups of compounds may be expressed by the following sub-formulae Iaa to Iaj, which conform to the formula Ia and Ib and in which the radicals not designated in greater detail have the meaning indicated for the formula Ia and Ib, but in which in Iaa Ar denotes phenyl which is unsubstituted or mono-, di- or trisubstituted by Hal, OH, OA, $NH_2$, NHA, $NA_2$ and/or $NHCH_2Ar^1$;

in Iab Het denotes furyl, thienyl, pyrrolyl, imidazolyl, pyrazolyl, oxazo-lyl, isoxazolyl, thiazolyl, isothiazolyl, pyridyl, pyrimidinyl, triazolyl, tetrazolyl, oxadiazolyl, thiadiazolyl, pyridazinyl, pyrazinyl, benzimidazolyl, benzotriazolyl, quinolinyl, quinoxalinyl, quinazolinyl, pyrrolopyridinyl, purinyl, indolyl or indazolyl, each of which is unsubstituted or mono- or disubstituted by $NH_2$ and/or $NHCH_2Ar^1$;

in Iac $Ar^1$ denotes phenyl;

in Iad $Het^1$ denotes piperidinyl, pyrrolidinyl, morpholinyl, piperazinyl, imidazolidinyl, oxazolidinyl, tetrahydropyranyl, thiazolyl, thiophenyl, furanyl, pyrrolyl, oxazolyl, isoxazolyl, oxadiazolyl, pyrazolyl, imidazolyl, triazolyl, thiadiazolyl, pyridazinyl, pyrazinyl, pyridinyl or pyrimidinyl, each of which is unsubstituted or mono- or disubstituted by $NH_2$ and/or $CH_2Het^2$;

in Iae $Het^2$ denotes furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, pyrazinyl, benzimidazolyl, benzotriazolyl, quinolinyl, quinoxalinyl, quinazolinyl, pyrrolopyridinyl, purinyl, indolyl or indazolyl, each of which is unsubstituted or mono- or disubstituted by A and/or $NH_2$;

in Iaf $Het^3$ denotes furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, pyrazinyl, benzimidazolyl, benzotriazolyl, quinolinyl, quinoxalinyl, quinazolinyl, pyrrolopyridinyl, purinyl, indolyl or indazolyl, each of which is unsubstituted or mono- or disubstituted by A and/or $NH_2$;

in Iag $Het^4$ denotes piperidinyl, pyrrolidinyl, morpholinyl, piperazinyl, imidazolidinyl, oxazolidinyl, tetrahydropyranyl, dihydroiso-indolyl, furyl, thienyl, pyrrolyl, imidazolyl, pyrazolyl, oxazolyl, isoxazolyl, thiazolyl, isothiazolyl, pyridyl, pyrimidinyl, tri-azolyl, tetrazolyl, oxadiazolyl, thiadiazolyl, pyridazinyl, pyrazinyl, benzimidazolyl, benzotriazolyl, quinolinyl, quinoxalinyl, quinazolinyl, pyrrolopyridinyl, purinyl, indolyl or indazolyl, each of which is unsubstituted or mono- or disubstituted by $NH_2$, $NHCH_2Ar^1$ and/or =O;

in Iah $R^1$ denotes H, $(CH_2)_n$Ar or $(CH_2)_n$Het,
$R^1$ denotes H,
$R^2$ denotes H, Hal, $(CH_2)_n Het^1$, $(CH_2)_n Het^3$ or —C≡C—Ar,
$R^3$ denotes NHCOOA' or $NH_2$,
$R^4$ denotes $(CH_2)_n$Ar, $SiA_3$ or $(CH_2)_n Het^4$,
$R^5$ denotes H or $(CH_2)_n Het^3$,
$R^6$ denotes H, —C≡C—$R^4$ or Hal,
$R^7$ denotes H,
Ar denotes phenyl which is unsubstituted or mono-, di- or trisubstituted by Hal, A, OH, OA, CN, $NO_2$, $SO_2A$, COOH, COOA, $NH_2$, NHA, $NA_2$, $NHCH_2Ar^1$, CHO, COA, CHO, $CONH_2$, CONHA, $CONA_2$, $SO_2NH_2$, $SO_2NHA$ and/or NHCOA,
Het denotes a mono- or bicyclic aromatic heterocycle having 1 to 4 N, O and/or S atoms, which may be unsubstituted or mono-, di- or trisubstituted by Hal, A, $NH_2$ and/or $NHCH_2Ar^1$,
$Ar^1$ denotes phenyl which is unsubstituted or mono-, di- or tri-substituted by Hal, A, OH and/or OA,
$Het^1$ denotes a mono- or bicyclic aromatic, unsaturated or saturated heterocycle having 1 to 4 N, O and/or S atoms, which may be unsubstituted or mono-, di- or trisubstituted by Hal, A, $NH_2$ and/or $CH_2Het^2$, Het² denotes a mono- or bicyclic aromatic heterocycle having 1 to 4 N, O and/or S atoms, which may be unsubstituted or mono-, di- or trisubstituted by A and/or NH₂, Het³ denotes a mono- or bicyclic aromatic heterocycle having 1 to 4 N, O and/or S atoms, which may be unsubstituted or mono-, di- or trisubstituted by NH₂, Het⁴ denotes a mono- or bicyclic aromatic, unsaturated or saturated heterocycle having 1 to 4 N, O and/or S atoms, which may be unsubstituted or mono-, di- or trisubstituted by Hal, A, NH₂, NHCH₂Ar¹ and/or =O, A denotes unbranched or branched alkyl having 1-10 C atoms,
in which 1-7 H atoms may be replaced by OH, F, Cl and/or Br, A' denotes unbranched or branched alkyl having 1-4 C atoms, Hal denotes F, Cl, Br or I, n denotes 0, 1, 2, 3 or 4;

and pharmaceutically usable salts, tautomers and stereoisomers thereof, including mixtures thereof in all ratios.

The compounds of the formula Ia and Ib and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants known per se which are not mentioned here in greater detail.

Compounds of the formula Ia' can preferably be obtained by reacting a compound of the formula IIc with a compound of the formula IIIc. The starting compounds of the formulae IIc and IIIc are generally known. If they are novel, however, they can be prepared by methods known per se.

The reaction is carried out under conditions as are known to the person skilled in the art for an amino-palladation reaction (Example 1). Diverse catalysts can be used.

Depending on the conditions used, the reaction time is between a few minutes and 14 days, the reaction temperature is between about −30° and 140°, normally between 30° and 120°, in particular between about 60° and about 90°.

Suitable inert solvents are, for example, hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon di-sulfide; carboxylic acids, such as formic acid or acetic acid; nitro compounds, such as nitromethane or nitrobenzene; esters, such as ethyl acetate, or mixtures of the said solvents.

Particular preference is given to DMF.

Compounds of the formula Ib' can preferably be obtained by reacting a compound of the formula IId with a compound of the formula IIId.

The starting compounds of the formulae IId and IIId are generally known. If they are novel, however, they can be prepared by methods known per se.

The reaction is carried out under conditions as are known to the person skilled in the art for a Sonogashira reaction (Example 2). Diverse catalysts can be used.

Depending on the conditions used, the reaction time is between a few minutes and 14 days, the reaction temperature is between about −30° and 140°, normally between 10° and 100°, in particular between about 20° and about 80°.

Suitable inert solvents are, for example, hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon di-sulfide; carboxylic acids, such as formic acid or acetic acid; nitro compounds, such as nitromethane or nitrobenzene; esters, such as ethyl acetate, or mixtures of the said solvents.

Particular preference is given to tetrahydrofuran.

Compounds of the formula Ib" in which $R^5$ denotes chlorine can preferably be obtained by reacting a compound of the formula Ib" in which $R^5$ denotes H with N-chlorosuccinimide (Example 3).

The reaction is preferably carried out in THF at −78° C. after prior addition of BuLi in n-hexane.

Compounds of the formula Ib' in which $R^5$ denotes Het³ can preferably be obtained by reacting a compound of the formula Ib' in which $R^5$ denotes chlorine with a compound of the formula IVa (Example 4).

The reaction is carried out under conditions as are known to the person skilled in the art for a Suzuki reaction.

In the compounds of the formula IVa, L preferably denotes

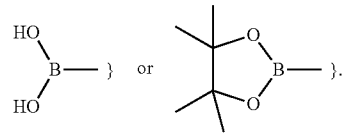

The reaction is carried out under standard conditions of a Suzuki coupling. Depending on the conditions used, the reaction time is between a few minutes and 14 days, the reaction temperature is between about −30° and 140°, normally between 0° and 100°, in particular between about 60° and about 90°.

Suitable inert solvents are, for example, hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon di-sulfide; carboxylic acids, such as formic acid or acetic acid; nitro compounds, such as nitromethane or nitrobenzene; esters, such as ethyl acetate, or mixtures of the said solvents.

Particular preference is given to ethanol, toluene, dimethoxyethane and/or water.

Compounds of the formula Ia" can also preferably be obtained by heating a compound of the formula Ib" in the presence of a base (Example 5). A suitable base is preferably potassium tert-butoxide.

Depending on the conditions used, the reaction time is between a few minutes and 14 days, the reaction temperature is between about −30° and 140°, normally between 30° and 120°, in particular between about 80° and about 110°.

Suitable inert solvents are, for example, hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon di-sulfide; carboxylic acids, such as formic acid or acetic acid; nitro compounds, such as nitromethane or nitrobenzene; esters, such as ethyl acetate, or mixtures of the said solvents.

Particular preference is given to NMP (N-methylpyrrolidone).

Furthermore, compounds of the formula Ib" can be obtained by reacting a compound of the formula Ib" in which $R^2$ denotes Hal, such as, for example, chlorine, with a compound of the formula Va (Example 6).

Depending on the conditions used, the reaction time is between a few minutes and 14 days, the reaction temperature is between about 0° and 140°, normally between 30° and 140°, in particular between about 80° and about 130°.

The reaction is carried out with or without solvents.

Analogously to process step e), the compounds of the formula Ia" according to the invention

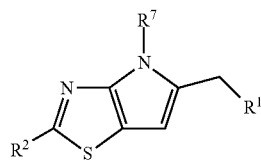

Ia"

in which
$R^1$ denotes Ar or Het,
$R^7$ denotes H,
and $R^2$, Ar, Het have the meanings indicated in claim 1, are obtained by heating a compound of the formula Ib'

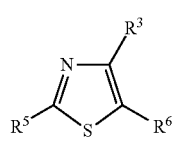

Ib' in which
$R^3$ denotes NH—COO-tert-butyl,
$R^6$ denotes —C≡C—$R^4$
$R^4$ denotes Ar or Het,
and Ar, Het, $R^2$ and $R^4$ have the meanings indicated in claim 1,
in the presence of a base (Example 5).

Furthermore, free amino groups can be acylated in a conventional manner using an acid chloride or anhydride or alkylated using an unsubstituted or substituted alkyl halide, advantageously in an inert solvent, such as dichloromethane or THF, and/or in the presence of a base, such as tri-ethylamine or pyridine, at temperatures between −60 and +30°.

The compounds of the formulae Ia and Ib can furthermore be obtained by liberating them from their functional derivatives by solvolysis, in particular hydrolysis, or by hydrogenolysis.

Preferred starting materials for the solvolysis or hydrogenolysis are those which contain corresponding protected amino and/or hydroxyl groups instead of one or more free amino and/or hydroxyl groups, preferably those which carry an amino-protecting group instead of an H atom bonded to an N atom, for example those which conform to the formula Ia and Ib, but contain an NHR' group (in which $R^7$ is an amino-protecting group, for example BOC or CBZ) instead of an $NH_2$ group.

Preference is furthermore given to starting materials which carry a hydroxyl-protecting group instead of the H atom of a hydroxyl group, for example those which conform to the formula Ia and Ib, but contain an R"O-phenyl group (in which R" is a hydroxyl-protecting group) instead of a hydroxyphenyl group.

It is also possible for a plurality of—identical or different—protected amino and/or hydroxyl groups to be present in the molecule of the starting material. If the protecting groups present are different from one another, they can in many cases be cleaved off selectively.

The term "amino-protecting group" is known in general terms and relates to groups which are suitable for protecting (blocking) an amino group against chemical reactions, but are easy to remove after the desired chemical reaction has been carried out elsewhere in the molecule. Typical of such groups are, in particular, unsubstituted or substituted acyl, aryl, aralkoxymethyl or aralkyl groups. Since the amino-protecting groups are removed after the desired reaction (or reaction sequence), their type and size are furthermore not crucial; however, preference is given to those having 1-20, in particular 1-8, carbon atoms. The term "acyl group" is to be understood in the broadest sense in connection with the present process. It includes acyl groups derived from aliphatic, araliphatic, aromatic or heterocyclic carboxylic acids or sulfonic acids, and, in particular, alkoxy-carbonyl, aryloxycarbonyl and especially aralkoxycarbonyl groups. Examples of such acyl groups are alkanoyl, such as acetyl, propionyl and butyryl; aralkanoyl, such as phenylacetyl; aroyl, such as benzoyl and tolyl; aryloxyalkanoyl, such as POA; alkoxycarbonyl, such as methoxycarbonyl, ethoxycarbonyl, 2,2,2-trichloroethoxycarbonyl, BOC and 2-iodoethoxy-carbonyl; aralkoxycarbonyl, such as CBZ ("carbobenzoxy"), 4-methoxy-benzyloxycarbonyl and FMOC; and arylsulfonyl, such as Mtr, Pbf and Pmc. Preferred amino-protecting groups are BOC and Mtr, furthermore CBZ, Fmoc, benzyl and acetyl.

The term "hydroxyl-protecting group" is likewise known in general terms and relates to groups which are suitable for protecting a hydroxyl group against chemical reactions, but are easy to remove after the desired chemical reaction has been carried out elsewhere in the molecule. Typical of such groups are the above-mentioned unsubstituted or substituted aryl, aralkyl or acyl groups, furthermore also alkyl groups. The nature and size of the hydroxyl-protecting groups are not crucial since they are removed again after the desired chemical reaction or reaction sequence; preference is given to groups having 1-20, in particular 1-10, carbon atoms. Examples of hydroxyl-protecting groups are, inter alia, tertbutoxycarbonyl, benzyl, p-nitrobenzoyl, p-toluenesulfonyl, tert-butyl and acetyl, where benzyl and tert-butyl are particularly preferred. The COOH groups in aspartic acid and glutamic acid are preferably protected in the form of their tert-butyl esters (for example Asp(OBut)).

The compounds of the formula Ia and Ib are liberated from their functional derivatives—depending on the protecting group used—for example using strong acids, advantageously using TFA or perchloric acid, but also using other strong inorganic acids, such as hydrochloric acid or sulfuric acid, strong organic carboxylic acids, such as trichloroacetic acid, or sulfonic acids, such as benzene- or p-toluenesulfonic acid. The presence of an additional inert solvent is possible, but is not always necessary. Suitable inert solvents are preferably organic, for example carboxylic acids, such as acetic acid, ethers, such as tetrahydrofuran or dioxane, amides, such as DMF, halogenated hydrocarbons, such as dichloromethane, furthermore also alcohols, such as methanol, ethanol or isopropanol, and water. Mixtures of the above-mentioned solvents are furthermore suitable. TFA is preferably used in excess without addition of a further solvent, and perchloric acid is preferably used in the form of a mixture of acetic acid and 70% perchloric acid in the ratio 9:1. The reaction temperatures for the cleavage are advantageously between about 0 and about 50°, preferably between 15 and 30° (room temperature).

The BOC, OBut, Pbf, Pmc and Mtr groups can, for example, preferably be cleaved off using TFA in dichloromethane or using approximately 3 to 5N HCl in dioxane at 15-30°, and the FMOC group can be cleaved off using an approximately 5 to 50% solution of dimethylamine, diethylamine or piperidine in DMF at 15-30°.

Hydrogenolytically removable protecting groups (for example CBZ or benzyl) can be cleaved off, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or amides, such as DMF. The hydrogenolysis is generally carried out at temperatures between about 0 and 100° and pressures between about 1 and 200 bar, preferably at 20-30° and 1-10 bar. Hydrogenolysis of the CBZ group succeeds well, for example, on 5 to 10% Pd/C in methanol or using ammonium formate (instead of hydrogen) on Pd/C in methanol/DMF at 20-30°.

Pharmaceutical Salts and Other Forms

The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds of the formula Ia and Ib are for the most part prepared by conventional methods. If the compound of the formula Ia or Ib contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminium salts of the compounds of the formula Ia and Ib are likewise included. In the case of certain compounds of the formula Ia and Ib, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoaryl-sulfonates, such as ethanesulfonate, toluenesulfonate and benzene-sulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds of the formula Ia and Ib include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitro-benzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethane-sulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenyl-acetate, 3-phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese(III), manganese(II), potassium, sodium and zinc salts, but this is not intended to represent a restriction. Of the above-mentioned salts, preference is given to ammonium; the alkali metal salts sodium and potassium, and the alkaline earth metal salts calcium and magnesium. Salts of the compounds of the formula Ia and Ib which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloro-procaine, choline, N,N'-dibenzyl-ethylenediamine(benzathine), dicyclo-hexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, iso-propylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris(hydroxymethyl)methylamine(tromethamine), but this is not intended to represent a restriction.

Compounds of the present invention which contain basic nitrogen-containing groups can be quaternised using agents such as ($C_1$-$C_4$)alkyl halides, for example methyl, ethyl, isopropyl and tert-butyl chloride, bromide and iodide; di($C_1$-$C_4$) alkyl sulfates, for example dimethyl, diethyl and diamyl sulfate; ($C_{10}$-$C_{18}$)alkyl halides, for example decyl, dodecyl, lauryl, myristyl and stearyl chloride, bromide and iodide; and aryl($C_1$-$C_4$)alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

Particular preference is given to hydrochloride, dihydrochloride, hydro-bromide, maleate, mesylate, phosphate, sulfate and succinate.

The acid-addition salts of basic compounds of the formula Ia and Ib are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds of the formula Ia and Ib are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expression "pharmaceutically acceptable salt" in the present connection is taken to mean an active ingredient which comprises a compound of the formula Ia and Ib in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

The invention furthermore relates to medicaments comprising at least one compound of the formula Ia and Ib and/or pharmaceutically usable salts and stereoisomers thereof, including mixtures thereof in all ratios, and optionally excipients and/or adjuvants.

Pharmaceutical formulations can be administered in the form of dosage units which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinyl-pyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tabletting machine, giving lumps of non-uniform shape, which are broken up to form granules. The granules can be lubricated by addition of stearic acid, a stearate salt, talc or mineral oil in order to prevent sticking to the tablet casting moulds.

The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formula Ia and Ib and salts thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds of the formula Ia and Ib and the salts thereof can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmeth-acrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, poly-orthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Res. 1986; 3 (6): 318 ff.

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula Ia or Ib depends on a number of factors, including, for example, the age and weight of the animal, the precise condition that requires treatment, and its severity, the nature of the formulation and the method of administration, and is ultimately determined by the treating doctor or vet. However, an effective amount of a compound according to the invention for the treatment of neoplastic growth, for example colon or breast carcinoma, is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

The invention furthermore relates to medicaments comprising at least one compound of the formula Ia or Ib and/or pharmaceutically usable salts and stereoisomers thereof, including mixtures thereof in all ratios, and at least one further medicament active ingredient.

The invention also relates to a set (kit) consisting of separate packs of
(a) an effective amount of a compound of the formula Ia or Ib and/or pharmaceutically usable salts and stereoisomers thereof, including mixtures thereof in all ratios, and
(b) an effective amount of a further medicament active ingredient.

The set comprises suitable containers, such as boxes, individual bottles, bags or ampoules. The set may, for example, comprise separate ampoules, each containing an effective amount of a compound of the formula Ia or Ib and/or pharmaceutically usable salts and stereoisomers thereof, including mixtures thereof in all ratios, and an effective amount of a further medicament active ingredient in dissolved or lyophilised form.

Use

The present compounds are suitable as pharmaceutical active ingredients for mammals, especially for humans, in the treatment of tyrosine kinase-induced diseases. These diseases include the proliferation of tumour cells, pathological neovascularisation (or angiogenesis) which promotes the growth of solid tumours, ocular neovascularisation (diabetic retinopathy, age-induced macular degeneration and the like) and inflammation (psoriasis, rheumatoid arthritis and the like).

The present invention encompasses the use of the compounds of the formula Ia and Ib and/or physiologically acceptable salts thereof for the preparation of a medicament for the treatment or prevention of cancer. Preferred carcinomas for the treatment originate from the group cerebral carcinoma, urogenital tract carcinoma, carcinoma of the lymphatic system, stomach carcinoma, laryngeal carcinoma and lung carcinoma. A further group of preferred forms of cancer are monocytic leukaemia, lung adenocarcinoma, small-cell lung carcinomas, pancreatic cancer, glioblastomas and breast carcinoma.

Also encompassed is the use of the compounds according to claim 1 according to the invention and/or physiologically acceptable salts thereof for the preparation of a medicament for the treatment or prevention of a disease in which angiogenesis is implicated.

Such a disease in which angiogenesis is implicated is an ocular disease, such as retinal vascularisation, diabetic retinopathy, age-induced macular degeneration and the like.

The use of compounds of the formula Ia and Ib and/or physiologically acceptable salts and solvates thereof for the preparation of a medicament for the treatment or prevention of inflammatory diseases also falls within the scope of the present invention. Examples of such inflammatory diseases include rheumatoid arthritis, psoriasis, contact dermatitis, delayed hypersensitivity reaction and the like.

Also encompassed is the use of the compounds of the formula Ia and Ib and/or physiologically acceptable salts thereof for the preparation of a medicament for the treatment or prevention of a tyrosine kinase-induced disease or a tyrosine kinase-induced condition in a mammal, in which to this method a therapeutically effective amount of a compound according to the invention is administered to a sick mammal in need of such treatment.

The therapeutic amount varies according to the specific disease and can be determined by the person skilled in the art without undue effort.

The present invention also encompasses the use compounds of the formula Ia and Ib and/or physiologically acceptable salts and solvates thereof for the preparation of a medicament for the treatment or prevention of retinal vascularisation.

Methods for the treatment or prevention of ocular diseases, such as diabetic retinopathy and age-induced macular degeneration, are likewise part of the invention. The use for the treatment or prevention of inflammatory diseases, such as rheumatoid arthritis, psoriasis, contact dermatitis and delayed hypersensitivity reaction, as well as the treatment or prevention of bone pathologies from the group osteosarcoma, osteoarthritis and rickets, likewise falls within the scope of the present invention.

The expression "tyrosine kinase-induced diseases or conditions" refers to pathological conditions that depend on the activity of one or more tyrosine kinases. Tyrosine kinases either directly or indirectly participate in the signal transduction pathways of a variety of cellular activities, including proliferation, adhesion and migration and differentiation. Diseases associated with tyrosine kinase activity include proliferation of tumour cells, pathological neovascularisation that promotes the growth of solid tumours, ocular neovascularisation (diabetic retinopathy, age-induced macular degeneration and the like) and inflammation (psoriasis, rheumatoid arthritis and the like).

The compounds of the formula Ia and Ib can be administered to patients for the treatment of cancer, in particular fast-growing tumours.

The invention thus relates to the use of compounds of the formula Ia and Ib, and pharmaceutically usable salts and stereoisomers thereof, including mixtures thereof in all ratios, for the preparation of a medicament for the treatment of diseases in which the inhibition, regulation and/or modulation of kinase signal transduction plays a role.

Preference is given to the use of compounds of the formula I, and pharmaceutically usable salts and stereoisomers thereof, including mixtures thereof in all ratios,
for the preparation of a medicament for the treatment of diseases which are influenced by inhibition of tyrosine kinases by the compounds according to claim 1.

Particular preference is given to the use for the treatment of a disease where the disease is a solid tumour.

The solid tumour is preferably selected from the group of tumours of the lung, squamous epithelium, the bladder, the stomach, the kidneys, of head and neck, the oesophagus, the cervix, the thyroid, the intestine, the liver, the brain, the prostate, the urogenital tract, the lymphatic system, the stomach and/or the larynx.

The solid tumour is furthermore preferably selected from the group lung adenocarcinoma, small-cell lung carcinomas, pancreatic cancer, glioblastomas, colon carcinoma and breast carcinoma.

Preference is furthermore given to the use for the treatment of a tumour of the blood and immune system, preferably for the treatment of a tumour selected from the group of acute myeloid leukaemia, chronic myeloid leukaemia, acute lymphatic leukaemia and/or chronic lymphatic leukaemia.

The disclosed compounds of the formula Ia and Ib can be administered in combination with other known therapeutic agents, including anticancer agents. As used here, the term "anticancer agent" relates to any agent which is administered to a patient with cancer for the purposes of treating the cancer.

The anti-cancer treatment defined herein may be applied as a sole therapy or may involve, in addition to the compound of the invention, conventional surgery or radiotherapy or chemotherapy. Such chemotherapy may include one or more of the following categories of anti- tumour agents:

(i) antiproliferative/antineoplastic/DNA-damaging agents and combinations thereof, as used in medical oncology, such as alkylating agents (for example cis-platin, carboplatin, cyclophosphamide, nitrogen mustard, melphalan, chloroambucil, busulphan and nitrosoureas); antimetabolites (for example antifolates such as fluoropyrimidines like 5-fluorouracil and tegafur, raltitrexed, methotrexate, cytosine arabinoside, hydroxyurea and gemcitabine); antitumour antibiotics (for example anthracyclines, like adriamycin, bleomycin, doxorubicin, daunomycin, epirubicin, idarubicin, mitomycin-C, dactinomycin and mithramycin); antimitotic agents (for example vinca alkaloids, like vincristine, vinblastine, vindesine and vinorelbine, and taxoids, like taxol and taxotere); topoisomerase inhibitors (for example epipodophyllotoxins, like etoposide and teniposide, amsacrine, topotecan, irinotecan and camptothecin) and cell-differentiating agents (for example all-trans-retinoic acid, 13-cis-retinoic acid and fenretinide);

(ii) cytostatic agents, such as antioestrogens (for example tamoxifen, toremifene, raloxifene, droloxifene and iodoxyfene), oestrogen receptor downregulators (for example fulvestrant), antiandrogens (for example bicalutamide, flutamide, nilutamide and cyproterone acetate), LHRH antagonists or LHRH agonists (for example goserelin, leuprorelin and buserelin), progesterones (for example megestrol acetate), aromatase inhibitors (for example as anastrozole, letrozole, vorazole and exemestane) and inhibitors of 5α-reductase, such as finasteride;

(iii) agents which inhibit cancer cell invasion (for example metallo-proteinase inhibitors, like marimastat, and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab [Herceptin™] and the anti-erbb1 antibody cetuximab [C225]), farnesyl transferase inhibitors, tyrosine kinase inhibitors and serine/threonine kinase inhibitors, for example inhibitors of the epidermal growth factor family (for example EGFR family tyrosine kinase inhibitors, such as N-(3-chloro-4-fluorophenyl)-7-methoxy-6- (3-morpholinopropoxy) quinazolin-4-amine (gefitinib, AZD-1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholino-propoxy)quinazolin-4-amine (CI 1033)), for example inhibitors of the platelet-derived growth factor family and for example inhibitors of the hepatocyte growth factor family;

(v) antiangiogenic agents, such as those which inhibit the effects of vascular endothelial growth factor, (for example the anti-vascular endothelial cell growth factor antibody bevacizumab [Avastin™], compounds such as those disclosed in published international patent applications WO 97/22596, WO 97/30035, WO 97/32856 and WO 98/13354) and compounds that work by other mechanisms (for example linomide, inhibitors of integrin αvβ3 function and angiostatin);

(vi) vessel-damaging agents, such as combretastatin A4 and compounds disclosed in international patent applications WO 99/02166, WO 00/40529, WO 00/41669, WO 01/92224, WO 02/04434 and WO 02/08213;

(vii) antisense therapies, for example those which are directed to the targets listed above, such as ISIS-2503, an anti-Ras antisense;

(viii) gene therapy approaches, including, for example, approaches for replacement of aberrant genes, such as aberrant p53 or aberrant BRCA1 or BRCA2, GDEPT (gene-directed enzyme pro-drug therapy) approaches, such as those using cytosine deaminase, thymidine kinase or a bacterial nitroreductase enzyme, and approaches for increasing patient tolerance to chemotherapy or radiotherapy, such as multi-drug resistance gene therapy; and (ix) immunotherapy approaches, including, for example, ex-vivo and in-vivo approaches for increasing the immunogenicity of patient tumour cells, such as transfection with cytokines, such as interleukin 2, interleukin 4 or granulocyte-macrophage colony stimulating factor, approaches for decreasing T-cell energy, approaches using transfected immune cells, such as cytokine-transfected dendritic cells, approaches using cytokine-transfected tumour cell lines, and approaches using anti-idiotypic anti-bodies.

The medicaments from Table 1 below are preferably, but not exclusively, combined with the compounds of the formula I.

TABLE 1

| | | |
|---|---|---|
| Alkylating agents | Cyclophosphamide | Lomustine |
| | Busulfan | Procarbazine |
| | Ifosfamide | Altretamine |
| | Melphalan | Estramustine phosphate |
| | Hexamethylmelamine | Mechloroethamine |
| | Thiotepa | Streptozocin |
| | Chloroambucil | Temozolomide |
| | Dacarbazine | Semustine |
| | Carmustine | |
| Platinum agents | Cisplatin | Carboplatin |
| | Oxaliplatin | ZD-0473 (AnorMED) |
| | Spiroplatin | Lobaplatin (Aetema) |
| | Carboxyphthalatoplatinum | Satraplatin (Johnson |
| | Tetraplatin | Matthey) |
| | Ormiplatin | BBR-3464 (Hoffmann-La |
| | Iproplatin | Roche) |
| | | SM-11355 (Sumitomo) |
| | | AP-5280 (Access) |

TABLE 1-continued

| | | |
|---|---|---|
| Antimetabolites | Azacytidine | Tomudex |
| | Gemcitabine | Trimetrexate |
| | Capecitabine | Deoxycoformycin |
| | 5-Fluorouracil | Fludarabine |
| | Floxuridine | Pentostatin |
| | 2-Chlorodesoxyadenosine | Raltitrexed |
| | 6-Mercaptopurine | Hydroxyurea |
| | 6-Thioguanine | Decitabine (SuperGen) |
| | Cytarabine | Clofarabine (Bioenvision) |
| | 2-Fluorodesoxycytidine | Irofulven (MGI Pharma) |
| | Methotrexate | DMDC (Hoffmann- |
| | Idatrexate | La Roche) |
| | | Ethynylcytidine (Taiho) |
| Topoisomerase inhibitors | Amsacrine | Rubitecan (SuperGen) |
| | Epirubicin | Exatecan mesylate (Daiichi) |
| | Etoposide | Quinamed (ChemGenex) |
| | Teniposide or mitoxantrone | Gimatecan (Sigma-Tau) |
| | Irinotecan (CPT-11) | Diflomotecan (Beaufour-Ipsen) |
| | 7-Ethyl-10-hydroxy-camptothecin | TAS-103 (Taiho) |
| | Topotecan | Elsamitrucin (Spectrum) |
| | Dexrazoxanet (TopoTarget) | J-107088 (Merck & Co) |
| | Pixantrone (Novuspharma) | BNP-1350 (BioNumerik) |
| | Rebeccamycin analogue (Exelixis) | CKD-602 (Chong Kun Dang) |
| | BBR-3576 (Novuspharma) | KW-2170 (Kyowa Hakko) |
| Antitumour antibiotics | Dactinomycin (Actinomycin D) | Amonafide |
| | Doxorubicin (Adriamycin) | Azonafide |
| | Deoxyrubicin | Anthrapyrazole |
| | Valrubicin | Oxantrazole |
| | Daunorubicin (Daunomycin) | Losoxantrone |
| | Epirubicin | Bleomycin sulfate |
| | Therarubicin | (Blenoxan) |
| | Idarubicin | Bleomycinic acid |
| | Rubidazon | Bleomycin A |
| | Plicamycinp | Bleomycin B |
| | Porfiromycin | Mitomycin C |
| | Cyanomorpholinodoxorubicin | MEN-10755 (Menarini) |
| | Mitoxantron (Novantron) | GPX-100 (Gem Pharmaceuticals) |
| Antimitotic agents | Paclitaxel | SB 408075 (GlaxoSmithKline) |
| | Docetaxel | E7010 (Abbott) |
| | Colchicine | PG-TXL (Cell Therapeutics) |
| | Vinblastine | IDN 5109 (Bayer) |
| | Vincristine | A 105972 (Abbott) |
| | Vinorelbine | A 204197 (Abbott) |
| | Vindesine | LU 223651 (BASF) |
| | Dolastatin 10 (NCI) | D 24851 (ASTA Medica) |
| | Rhizoxin (Fujisawa) | ER-86526 (Eisai) |
| | Mivobulin (Warner-Lambert) | Combretastatin A4 (BMS) |
| | Cemadotin (BASF) | Isohomohalichondrin-B |
| | RPR 109881A (Aventis) | (PharmaMar) |
| | TXD 258 (Aventis) | ZD 6126 (AstraZeneca) |
| | Epothilone B (Novartis) | PEG-Paclitaxel (Enzon) |
| | T 900607 (Tularik) | AZ10992 (Asahi) |
| | T 138067 (Tularik) | !DN-5109 (Indena) |
| | Cryptophycin 52 (Eli Lilly) | AVLB (Prescient |
| | Vinflunine (Fabre) | NeuroPharma) |
| | Auristatin PE (Teikoku Hormone) | Azaepothilon B (BMS) |
| | BMS 247550 (BMS) | BNP-7787 (BioNumerik) |
| | BMS 184476 (BMS) | CA-4-prodrug (OXiGENE) |
| | BMS 188797 (BMS) | Dolastatin-10 (NrH) |
| | Taxoprexin (Protarga) | CA-4 (OXiGENE) |
| Aromatase inhibitors | Aminoglutethimide | Exemestane |
| | Letrozole | Atamestan (BioMedicines) |
| | Anastrazole | YM-511 (Yamanouchi) |
| | Formestan | |
| Thymidylate synthase inhibitors | Pemetrexed (Eli Lilly) | Nolatrexed (Eximias) |
| | ZD-9331 (BTG) | CoFactor ™ (BioKeys) |
| DNA antagonists | Trabectedin (PharmaMar) | Mafosfamide (Baxter International) |
| | Glufosfamide (Baxter International) | Apaziquone (Spectrum Pharmaceuticals) |
| | Albumin + 32P (Isotope Solutions) | O6-benzylguanine (Paligent) |
| | Thymectacin (NewBiotics) | |
| | Edotreotid (Novartis) | |

TABLE 1-continued

| | | |
|---|---|---|
| Farnesyl transferase inhibitors | Arglabin (NuOncology Labs) Ionafarnib (Schering-Plough) BAY-43-9006 (Bayer) | Tipifarnib (Johnson & Johnson) Perillyl alcohol (DOR BioPharma) |
| Pump inhibitors | CBT-1 (CBA Pharma) Tariquidar (Xenova) MS-209 (Schering AG) | Zosuquidar trihydrochloride (Eli Lilly) Biricodar dicitrate (Vertex) |
| Histone acetyl transferase inhibitors | Tacedinaline (Pfizer) SAHA (Aton Pharma) MS-275 (Schering AG) | Pivaloyloxymethyl butyrate (Titan) Depsipeptide (Fujisawa) |
| Metalloproteinase inhibitors | Neovastat (Aeterna Laboratories) | CMT-3 (CollaGenex) BMS-275291 (Celltech) |
| Ribonucleoside reductase inhibitors | Marimastat (British Biotech) Gallium maltolate (Titan) Triapin (Vion) | Tezacitabine (Aventis) Didox (Molecules for Health) |
| TNF-alpha agonists/antagonists | Virulizin (Lorus Therapeutics) CDC-394 (Celgene) | Revimid (Celgene) |
| Endothelin-A receptor antagonists | Atrasentan (Abbot) ZD-4054 (AstraZeneca) | YM-598 (Yamanouchi) |
| Retinoic acid receptor agonists | Fenretinide (Johnson & Johnson LGD-1550 (ligand) | Alitretinoin (Ligand) |
| Immunomodulators | Interferon Oncophage (Antigenics) GMK (Progenics) Adenocarcinoma vaccine (Biomira) CTP-37 (AVI BioPharma) JRX-2 (Immuno-Rx) PEP-005 (Peplin Biotech) Synchrovax vaccines (CTL Immuno) Melanoma vaccine (CTL Immuno) p21-RAS vaccine (GemVax) | Dexosome therapy (Anosys Pentrix (Australian Cancer Technology) JSF-154 (Tragen) Cancer vaccine (Intercell) Norelin (Biostar) BLP-25 (Biomira) MGV (Progenics) !3-Alethin (Dovetail) CLL-Thera (Vasogen) |
| Hormonal and antihormonal agents | Oestrogens Conjugated oestrogens Ethynyloestradiol Chlorotrianisene Idenestrol Hydroxyprogesterone caproate Medroxyprogesterone Testosterone Testosterone propionate Fluoxymesterone Methyltestosterone Diethylstilbestrol Megestrol Tamoxifen Toremofin Dexamethasone | Prednisone Methylprednisolone Prednisolone Aminoglutethimide Leuprolide Goserelin Leuporelin Bicalutamide Flutamide Octreotide Nilutamide Mitotan P-04 (Novogen) 2-Methoxyoestradiol (EntreMed) Arzoxifen(Eli Lilly) |
| Photodynamic agents | Talaporfin (Light Sciences) Theralux (Theratechnologies) Motexafin-Gadolinium (Pharmacyclics) | Pd-Bacteriopheophorbid (Yeda) Lutetium-Texaphyrin (Pharmacyclics) Hypericin |
| Tyrosine kinase inhibitors | Imatinib (Novartis) Leflunomide(Sugen/Pharmacia ZD1839 (AstraZeneca) Erlotinib (Oncogene Science) Canertjnib (Pfizer) Squalamine (Genaera) SU5416 (Pharmacia) SU6668 (Pharmacia) ZD4190 (AstraZeneca) ZD6474 (AstraZeneca) Vatalanib (Novartis) PKI166 (Novartis) GW2016 (GlaxoSmithKline) EKB-509 (Wyeth) EKB-569 (Wyeth) | Kahalide F (PharmaMar) CEP-701 (Cephalon) CEP-751 (Cephalon) MLN518 (Millenium) PKC412 (Novartis) Phenoxodiol O Trastuzumab (Genentech) C225 (ImClone) rhu-Mab (Genentech) MDX-H210 (Medarex) 2C4 (Genentech) MDX-447 (Medarex) ABX-EGF (Abgenix) IMC-1C11 (ImClone) |
| Various agents | SR-27897 (CCK-A inhibitor, Sanofi-Synthelabo) Tocladesine (cyclic AMP agonist, Ribapharm) Alvocidib (CDK inhibitor, Aventis CV 247 (COX-2 inhibitor, Ivy Medical) P54 (COX-2 inhibitor, Phytopharm) | BCX-1777 (PNP inhibitor, BioCryst) Ranpirnase (ribonuclease stimulant, Alfacell) Galarubicin (RNA synthesis inhibitor, Dong-A) Tirapazamine (reducing agent, SRI International) |

TABLE 1-continued

| | |
|---|---|
| CapCell ™ (CYP450 stimulant, Bavarian Nordic) | N-Acetylcysteine (reducing agent, Zambon) |
| GCS-IOO (gal3 antagonist, GlycoGenesys) | R-Flurbiprofen (NF-kappaB inhibitor, Encore) |
| G17DT immunogen (gastrin inhibitor, Aphton) | 3CPA (NF-kappaB inhibitor, Active Biotech) |
| Efaproxiral (oxygenator, Allos Therapeutics) | Seocalcitol (vitamin D receptor agonist, Leo) |
| PI-88 (heparanase inhibitor, Progen) | 131-I-TM-601 (DNA antagonist, Trans Molecular) |
| Tesmilifen (histamine antagonist, YM BioSciences) | Eflornithin (ODC inhibitor, ILEX Oncology) |
| Histamine (histamine H2 receptor agonist, Maxim) | Minodronic acid (osteoclast inhibitor, Yamanouchi) |
| Tiazofurin (IMPDH inhibitor, Ribapharm) | Indisulam (p53 stimulant, Eisai) |
| Cilengitide (integrin antagonist Merck KGaA) | Aplidin (PPT inhibitor, PharmaMar) |
| SR-31747 (IL-1 antagonist, Sanofi-Synthelabo) | Rituximab (CD20 antibody, Genentech) |
| CCI-779 (mTOR kinase inhibitor, Wyeth) | Gemtuzumab (CD33 antibody, Wyeth Ayerst) |
| Exisulind (PDE-V inhibitor, Cell Pathways) | PG2 (haematopoiesis promoter, Pharmagenesis) |
| CP-461 (PDE-V inhibitor, Cell Pathways) | Immunol ™ (triclosan mouthwash, Endo) |
| AG-2037 (GART inhibitor, Pfizer) | Triacetyluridine (uridine prodrug, Wellstat) |
| WX-UK1 (plasminogen activator inhibitor, Wilex) | SN-4071 (sarcoma agent, Signature BioScience) |
| PBI-1402 (PMN stimulant, ProMetic LifeSciences) | TransMID-107 ™ (immunotoxin, KS Biomedix) |
| Bortezomib (proteasome inhibitor Millennium) | PCK-3145 (apoptosis promoter, Procyon) |
| SRL-172 (T-cell stimulant, SR Pharma) | Doranidazole (apoptosis promoter, Pola) |
| TLK-286 (glutathione-S transferase inhibitor, Telik) | CHS-828 (cytotoxic agent, Leo) |
| PT-100 (growth factor agonist, Point Therapeutics) | trans-Retinic acid (differentiator, NIH) |
| Midostaurin (PKC inhibitor, Novartis) | MX6 (apoptosis promoter, MAXIA) |
| Bryostatin-1 (PKC stimulant, GPC Biotech) | Apomine (apoptosis promoter, ILEX Oncology) |
| CDA-II (apoptosis promoter, Everlife) | Urocidin (apoptosis promoter Bioniche) |
| SDX-101 (apoptosis promoter, Salmedix) | Ro-31-7453 (apoptosis promoter, La Roche) |
| Ceflatonin (apoptosis promoter ChemGenex) | Brostallicin (apoptosis promoter, Pharmacia) |

A combined treatment of this type can be achieved with the aid of simultaneous, consecutive or separate dispensing of the individual components of the treatment. Combination products of this type employ the compounds according to the invention.

Assays

The compounds of the formula Ia and Ib described in the examples were tested by the assays described below and were found to have kinase inhibitory activity. Other assays are known from the literature and could readily be performed by the person skilled in the art (see, for example, Dhanabal et al. Cancer Res. 1999; 59: 189-97; Xin et al. J. Biol. Chem. 1999; 274: 9116-21; Sheu et al. Anticancer Res. 1998; 18: 4435-41; Ausprunk et al. Dev. Biol.1974; 38: 237-48; Gimbrone et al. J. Natl. Cancer Inst. 1974; 52: 413-27; Nicosia et al. In Vitro 1982; 18: 538-49).

Filter Binding Assay

The substances are tested in accordance with the following provisions:

All equipment, solvents, buffers and enzymes used are commercially available.

All kinase assays were carried out using the Multidrop 384 from Thermo-Fisher at room temperature in a total assay volume of 25.5 µl. 15 µl of an enzyme mix comprising enzyme and substrate in buffer are added to the test batch comprising either 0.5 µl of test substance, DMSO control or empty container. Test substances are pre-incubated in the presence of the enzyme and substrate for 5 minutes before the reaction is initiated by addition of 10 µl of ATP (concentration kinase-dependent of 5, 20 or 50 mM). The reaction is terminated by addition of 5 µl of orthophosphoric acid (50 mM). The test containers are then transferred onto P81 Unifilter plates by means of a "Packard Harvester" and dried in air. The dry Unifilter plates are sealed after the addition of MicroScint O, and the radioactivity is determined in a Packard Topcount NXT.

Assay of NUAK1 Inhibition

NUAK1 (5-20 mU diluted in 50 mM Tris pH 7.5, 0.1 mM EGTA, 0.1% β-mercaptoethanol, 1 mg/ml of BSA) is tested against ALNRTSSDSALHRRR as substrate. The final volume of 25.5 µl contains 50 mM Tris pH 7.5, 0.1 mM EGTA, 0.3 mM ALNRTSSDSALHRRR, 10 mM magnesium acetate and 0.02 mM [$^{33}$P-γ-ATP] (50-1000 cpm/pmole) and is incubated at room temperature for 30 min. Tests are terminated by the addition of 5 μl of a 0.5 M (3%) orthophosphoric acid soln. and then transferred onto P81 Unifilter plates and washed with 50 mM orthophosphoric acid buffer.

Measurement of Met Kinase Activity

According to the manufacturer's data (Met, active, upstate, catalogue No. 14-526), Met kinase is expressed for the purposes of protein production in insect cells (Sf21; *S. frugiperda*) and subsequent affinity-chromatographic purification as "N-terminal 6His-tagged" recombinant human protein in a baculovirus expression vector.

The kinase activity can be measured using various available measurement systems. In the scintillation proximity method (Sorg et al., J. of Biomolecular Screening, 2002, 7, 11-19), the flashplate method or the filter binding test, the radioactive phosphorylation of a protein or peptide as substrate is measured using radioactively labelled ATP ($^{32}$P-ATP, $^{33}$P-ATP). In the case of the presence of an inhibitory compound, a reduced radioactive signal, or none at all, can be detected. Furthermore, homogeneous time-resolved fluorescence resonance energy transfer (HTR-FRET) and fluorescence polarisation (FP) technologies can be used as assay methods (Sills et al., J. Biomol. Screen. 2002; 7 (3): 191-214).

Other non-radioactive ELISA assay methods use specific phospho-anti-bodies (phospho-ABs). The phospho-antibody only binds the phosphorylated substrate. This binding can be detected by chemiluminescence using a second peroxidase-conjugated antibody (Ross et al. Biochem. J. 2002, 366: 977-981).

Flashplate Method (Met Kinase)

The test plates used are 96-well Flashplate$^R$ microtitre plates from Perkin Elmer (Cat. No. SMP200). The components of the kinase reaction described below are pipetted into the assay plate. The Met kinase and the substrate poly Ala-Glu-Lys-Tyr, (pAGLT, 6:2:5:1), are incubated for 3 hrs at room temperature with radioactively labelled $^{33}$P-ATP in the presence and absence of test substances in a total volume of 100 μl. The reaction is terminated using 150 μl of a 60 mM EDTA solution. After incubation for a further 30 min at room temperature, the supernatants are filtered off with suction, and the wells are washed three times with 200 μl of 0.9% NaCl solution each time. The measurement of the bound radioactivity is carried out by means of a scintillation measuring instrument (Topcount NXT, Perkin-Elmer).

The full value used is the inhibitor-free kinase reaction. This should be approximately in the range 6000-9000 cpm. The pharmacological zero value used is staurosporin in a final concentration of 0.1 mM. The inhibitory values (1050) are determined using the RS1_MTS program.

Kinase Reaction Conditions Per Well:
30 μl of assay buffer
10 μl of substance to be tested in assay buffer with 10% of DMSO
10 μl of ATP (final concentration 1 μM cold, 0.35 μCi of $^{33}$P-ATP)
50 μl of Met kinase/substrate mixture in assay buffer;
(10 ng of enzyme/well, 50 ng of pAGLT/well)
Solutions Used:
Assay Buffer:
50 mM HEPES
3 mM magnesium chloride
3 μM sodium orthovanadate
3 mM manganese(II) chloride
1 mM dithiothreitol (DTT)
pH=7.5 (to be set using sodium hydroxide)

Stop Solution:
60 mM Titriplex III (EDTA)
$^{33}$P-ATP: Perkin-Elmer;
Met kinase: Upstate, Cat. No. 14-526, stock 1 μg/10 μl; spec. activity 954 U/mg;
Poly-Ala-Glu-Lys-Tyr, 6: 2: 5: 1: Sigma Cat. No. P1152

In-vivo Tests

Experimental procedure: Female Balb/C mice (breeder: Charles River Wiga) were 5 weeks old on arrival. They were acclimatised to our keeping conditions for 7 days. Each mouse was subsequently injected subcutaneously in the pelvic area with 4 million TPR-Met/NIH3T3 cells in 100 μl of PBS (without Ca++ and Mg++). After 5 days, the animals were randomised into 3 groups, so that each group of 9 mice had an average tumour volume of 110 μl (range: 55-165). 100 μl of vehicle (0.25% methylcellulose/100 mM acetate buffer, pH 5.5) were administered daily to the control group, and 200 mg/kg of "A56" or "A91" dissolved in the vehicle (volume likewise 100 it/animal) were administered daily to the treatment groups, in each case by gastric tube. After 9 days, the controls had an average volume of 1530 μl and the experiment was terminated.

Measurement of the tumour volume: The length (L) and breadth (B) were measured using a Vernier calliper, and the tumour volume was calculated from the formula L×B×B/2.

Keeping conditions: 4 or 5 animals per cage, feeding with commercial mouse food (Sniff).

Conditions for the HPLC-based Analytical Methods:
ESI-MS: Agilent 1200 Binary Pump
Solvent A: water/0.05% of formic acid
Solvent B: ACN/0.04% of formic acid
Minimum pressure limit (bar): 0.0; Maximum pressure limit (bar): 200.0;
Post run time (min): 0.00;
Gradient program: Time Flow Rate Composition
0.00 (min) 2.40 (ml/min) A=96.0% B=4.0% gradient to
2.80 (min) 2.40 (ml/min) A=0.0% B=100.0%
3.30 (min) 2.40 (ml/min) A=0.0% B=100.0% gradient to
3.40 (min) 2.40 (ml/min) A=96.0% B=4.0%
Column: Chromolith Performance Speed ROD RP18e/50-4.6 nm
Autosampler: Agilent 1200 ALS G1329A
Pump: Agilent 1200 BinPump G1312A, Degasser: Agilent 1200 G1379B
Detector: Agilent 1200 VWL G1314B
MS: Agilent 6110 Quadrupole LC/MS
ESI interface G1946-60450, positive ionisation (or negative ionisation as indicated below), Injection volume: 10 μl
ESI-HRMS: Agilent 1100 Binary Pump
Solvent A: water/0.1% of FAc
Solvent B: ACN/0.1% of FAc
Minimum pressure limit (bar): 0.0; Maximum pressure limit (bar): 400.0;
Post run time (min): 0.00
Gradient program: Time Flow Rate Composition
0.00 (min) 0.50 (ml/min) A=98.0% B=2.0%
5.00 (min) 0.50 (ml/min) A=2.0% B=98.0%
8.00 (min) 0.50 (ml/min) A=2.0% B=98.0%
8.10 (min) 0.50 (ml/min) A=98.0% B=2.0%
13.00 (min) 0.50 (ml/min) A=98.0% B=2.0%
Column: 135- Purospher Star RP-18e (3 μm), 55-2, Art. 1.50241, No. 242994
Autosampler: Agilent 1100 ALS G1329A
Pump: Agilent 1100 BinPump G1312A
Column oven: Agilent 1100 Column Oven G1316A
Detection: Agilent 1100 DAD G1315B
MS: Thermo LTQ XL Orbitrap ESI interface
positive ionisation
Injection volume: 5-20 ul
APCI-MS:
Solvent A:water+0.1% of HCOOH
Solvent B:acetonitrile+0.1% of HCOOH
Solvent C:C
Solvent D:D
Min pressure (bar):0
Max pressure (bar):300
Delay volume (ml):0.00
Equilibration time (min):0.00
Gradient curve: linear
Gradient program:

| Time (min) | Flow (ml/min) | A (%) | B (%) | C (%) | D (%) |
|---|---|---|---|---|---|
| 0.00 | 0.50 | 98 | 2 | 0 | 0 |
| 5.00 | 0.50 | 2 | 98 | 0 | 0 |
| 8.00 | 0.50 | 2 | 98 | 0 | 0 |
| 8.10 | 0.50 | 98 | 2 | 0 | 0 |
| 13.00 | 0.50 | 98 | 2 | 0 | 0 |

Column: Purosphere RP-18, 55-2, Art. 1.50241.0001, batch: 641047
Pump: Finnigan Spectra P4000 system
Detection: Finnigan UV6000LP
MS: Finnigan LCQ Deca
APCI interface, Positive ionisation
Inj. vol.: 10 µl
$
Agilent
Column: Chromolite Performance RP18-e 50-4.6 mm
A: acetonitrile comprising 0.05% of formic acid
B:H₂O comprising 0.05% of formic acid
Flow rate: 2.4 ml/min
Method:

| Time [min] | % of B |
|---|---|
| 0 | 4 |
| 2.8 | 100 |
| 3.3 | 100 |
| 3.4 | 4 |

§
Agilent
Column:
XBridge C8 (50×4.6 mm, 3.5µ), +ve mode
Method:
A: 0.1% of TFA in H₂O
B: 0.1% of TFA in acetonitrile
Flow rate: 2.0 ml/min
Gradient:

| Time [min] | % of B |
|---|---|
| 0 | 5 |
| 8.0 | 100 |
| 8.1 | 100 |
| 8.5 | 5 |
| 10 | 5 |

Above and below, all temperatures are indicated in ° C. In the following examples, "convention work-up" means: water is added if necessary, the pH is adjusted, if necessary, to values between 2 and 10, depending on the constitution of the end product, the mixture is extracted with ethyl acetate or dichloromethane, the phases are separated, the organic phase is dried over sodium sulfate and evaporated, and the residue is purified by chromatography on silica gel and/or by crystallisation. Rf values on silica gel; eluent: ethyl acetate/methanol 9:1;

Mass spectrometry (MS): EI (electron impact ionisation) M⁺

FAB (fast atom bombardment) (M+H)⁺

ESI (electrospray ionisation) (M+H)⁺

APCI-MS (atmospheric pressure chemical ionisation—mass spectrometry) (M+H)⁺;

melting point m.p. in ° C.

EXAMPLE 1

Preparation of 6-benzyl-4H-pyrrolo[2,3-d]thiazole ("A7")

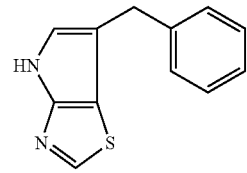 [SMILES: c1ccc(Cc2c[nH]c3ncsc23)cc1]

1.1 tert-Butyl N-(1,3-thiazol-4-yl)carbamate ("1")

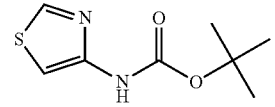

5.80 ml (41.84 mmol) of triethylamine and subsequently, with ice-bath cooling, 9.10 ml (42.19 mmol) of diphenyl azidophosphate are introduced into a solution of 4.85 g (37.55 mmol) of 4-thiazolecarboxylic acid in 180 ml of tert-butanol under nitrogen, and the reaction mixture is heated under reflux for 16 h. The solvent is removed in vacuo, the residue is taken up in dichloromethane and washed twice with water and saturated NaCl solution. The organic phase is dried over sodium sulfate, evaporated in vacuo, and the residue is purified by chromatography on silica gel (eluent: cyclohexane/ethyl acetate 1/1), giving 7.07 g (35.30 mmol, 94%) of tert-butyl N-(1,3-thiazol-4-yl)carbamate as beige crystals; ESI-MS: m/e: 201 ([M+H]⁺).

1.2 tert-Butyl N-(5-iodo-1,3-thiazol-4-yl)carbamate ("2")

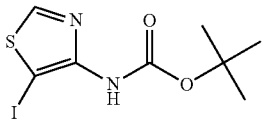

1033 mg (4.59 mmol) of N-iodosuccinimide are introduced into a solution of 800 mg (3.99 mmol) of tert-butyl N-(1,3-thiazol-4-yl)carbamate in 40 ml of dichloroethane, and the reaction mixture is heated under reflux for 2 h. After cooling, the mixture is washed twice with water and with saturated sodium thiosulfate solution. The combined organic phases are dried over sodium sulfate, evaporated in vacuo, and the residue is purified by flash chromatography on silica gel (eluent: cyclohexane/ethyl acetate 8/2 to 1/1), giving 1.19 g (3.43 mmol, 85%) of tert-butyl N-(5-iodo-1,3-thiazol-4-yl)carbamate as white crystals after crystallisation from diethyl ether; ESI-MS: m/e: 327 ([M+H]$^+$).

1.3 652 mg (2.00 mmol) of tert-butyl N-(5-iodo-1,3-thiazol-4-yl)carbamate and 2.6 g (8.00 mmol) of caesium carbonate are dissolved in 10 ml of dry DMF in a dried Schlenk flask under nitrogen, and 622 mg (3.00 mmol) of cinnamyl bromide are added. After stirring at room temperature for 2 h and positive reaction monitoring by means of thin-layer chromatography, 22 mg (0.10 mmol) of Pd(OAc)$_2$ and 52 mg (0.20 mmol) of PPh$_3$ are introduced, and the reaction mixture is stirred at 100° C. for 19 h. Saturated NaCl solution is then added to the reaction mixture, which is then extracted with ethyl acetate.

The combined organic phases are dried over sodium sulfate, evaporated in vacuo together with about three times the amount of SiO$_2$ and heated at 100° C. and about 10 mbar for 5 h. The substrate/silica gel mixture is subsequently purified directly by chromatography on a silica-gel column (eluent: cyclohexane/ethyl acetate 1/1), giving 214 mg (0.99 mmol, 49%) of 6-benzyl-4H-pyrrolo[2,3-d]thiazole as yellow residue;

m.p. 133-135;
APCI-MS: R$_t$: 3.90 min; m/e (%): 215 (100, [M+H]$^+$);
$^1$H NMR (400 MHz, DMSO-d$_6$): δ [ppm] 3.90 (s, 2H), 7.01 (dd, J$_{H,H}$=2.3 Hz, J$_{H,H}$=1.3 Hz, 1H), 7.14-7.34 (m, 5H), 8.65 (d, J$_{H,H}$=1.3 Hz, 1H), 11.58 (s, 1H);
$^{13}$C NMR (100 MHz, DMSO-d$_6$): δ [ppm] 32.14, 111.80, 113.02, 119.80, 125.42, 127.78, 127.96, 140.00, 149.75, 151.27.

EXAMPLE 2

Preparation of tert-butyl N-{5-[2-(4-fluorophenyl)ethynyl]-1,3-thiazol-4-yl}carbamate ("A15")

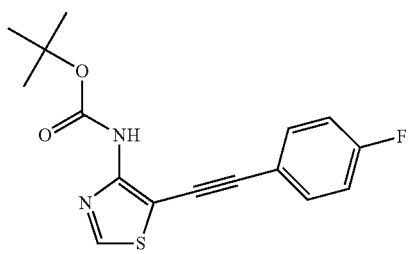 [SMILES: CC(C)(C)OC(=O)Nc1ncsc1C#Cc1ccc(F)cc1]

2.93 g (9 mmol) of caesium carbonate are dried in an evacuated Schlenk flask under temperature, and 50 ml of dry tetrahydrofuran, 978 mg (3.00 mmol) of tert-butyl N-(5-iodo-1,3-thiazol-4-yl)carbamate, 396 mg (3.30 mmol) of 1-ethynyl-4-fluorobenzene, 122 mg (0.15 mmol) of Pd(dppf)$_2$Cl$_2$.CH$_2$Cl$_2$ and 57 mg (0.30 mmol) of CuI are subsequently added under nitrogen. The reaction mixture is heated at 50° C. for 6 h, subsequently cooled and filtered through Celite, and the solvent is removed in vacuo. The residue is taken up with ethyl acetate and washed with saturated NaCl solution. The combined organic phases are dried over sodium sulfate, evaporated in vacuo, and the residue is purified by chromatography on silica gel (eluent: cyclohexane/ethyl acetate 1/1), giving 820 mg (2.57 mmol, 85%) of tert-butyl N-{5-[2-(4-fluorophenyl)ethynyl]-1,3-thiazol-4-yl}carbamate as yellow solid from diethyl ether;

m.p. 139-144;
$^1$H NMR (400 MHz, DMSO-d$_6$): δ [ppm] 1.45 (s, 9H), 7.22-7.39 (m, 2H), 7.50-7.68 (m, 2H), 8.98 (s, 1H), 9.62 (s, 1H);
$^{13}$C NMR (100 MHz, DMSO-d$_6$): δ [ppm] 27.43, 78.84, 96.31, 105.54, 115.35 (d, $^2$J$_{C,F}$=22 Hz), 117.92, 117.95, 132.88 (d, $^3$J$_{C,F}$=8 Hz), 150.65, 151.83, 152.1, 161.63 (d, $^1$J$_{C,F}$=246 Hz);
ESI-MS: R$_t$: 2.47 min; m/e (%): 319 (100, [M+H]$^+$).

EXAMPLE 3

Preparation of tert-butyl N-{2-chloro-5-[2-(4-fluorophenyl)ethynyl]-1,3-thiazol-4-yl}carbamate ("A29a")

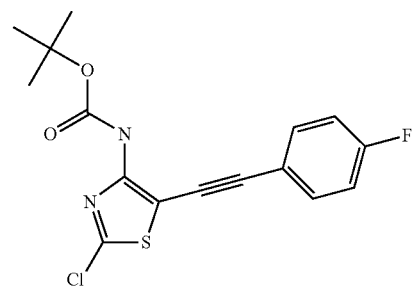 [SMILES: CC(C)(C)OC(=O)Nc1nc(Cl)sc1C#Cc1ccc(F)cc1]

2.63 g (8.26 mmol) of tert-butyl N-{5-[2-(4-fluorophenyl)ethynyl]-1,3-thiazol-4-yl}carbamate are dissolved in 100 ml of dry THF in a dried Schlenk flask under nitrogen and cooled to −78° C. 11 ml of a 15% solution of n-BuLi in n-hexane are then slowly added dropwise, and the mixture is stirred at −78° C. for 20 min. 1120 mg (8.38 mmol) of N-chlorosuccinimide dissolved in 1 ml of dry THF are subsequently added dropwise, and the mixture is stirred at −78° C. for 15 min, then quenched using 10 ml of n-butanol and warmed to RT. The solvent is removed in vacuo, and the residue is purified directly by chromatography on silica gel (eluent: cyclohexane/ethyl acetate 99/1), giving 2.3 g (6.51 mmol, 78%) of tert-butyl N-{2-chloro-5-[2-(4-fluorophenyl)ethynyl]-1,3-thiazol-4-yl}-carbamate as beige solid from PE; ESI-MS: m/e: 353 ([M+H]$^+$).

EXAMPLE 4

Preparation of tert-butyl N-[2-(2-aminopyrimidin-5-yl)-5-[2-(4-fluorophenyl)-ethynyl]-1,3-thiazol-4-yl]carbamate ("A29")

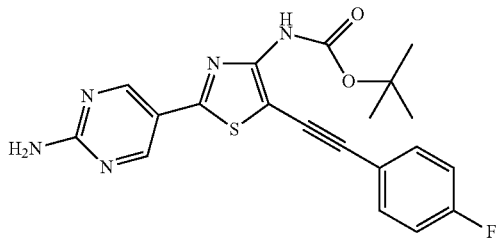 [SMILES: CC(C)(C)OC(=O)Nc1nc(-c2cnc(N)nc2)sc1C#Cc1ccc(F)cc1]

705 mg (2.00 mmol) of tert-butyl N-{2-chloro-5-[2-(4-fluorophenyl)ethynyl]-1,3-thiazol-4-yl}carbamate are dissolved in a mixture of 4 ml of DMF, 2 ml of water and 8 ml of DME together with 663 mg (3.00 mmol) of pinacolyl 2-amino-pyrimidine-5-boronate, and 829 mg (6.00 mmol) of potassium carbonate and 81 mg (0.10 mmol) of Pd(dppf)$_2$Cl$_2$.CH$_2$Cl$_2$ are introduced. Argon is subsequently passed through the reaction mixture for 10 min, the vessel is sealed and heated at 85° C. for 44 h. After cooling, the reaction mixture is extracted twice with saturated NaCl solution, and the aqueous phases are extracted with ethyl acetate. The combined organic phases are dried over sodium sulfate, evaporated in vacuo, and the residue is purified by flash chromatography on silica gel (eluent: cyclohexane/ethyl acetate 1/2; 1% of triethylamine), giving 205 mg (0.49 mmol, 25%) of tert-butyl N-[2-(2-aminopyrimidin-5-yl)-5-[2-(4-fluorophenyl)ethynyl]-1,3-thiazol-4-yl]carbamate as yellow solid; m.p. 201-203;

$^1$H NMR (300 MHz, DMSO-d$_6$): δ [ppm] 1.46 (s, 9H), 7.23-7.49 (m, 4H), 7.51-7.70 (m, 2H), 8.72 (s, 2H), 9.63 (s, 1H);

ESI-MS: R$_t$: 2.43 min; m/e (%): 412 (100, [M+H]$^+$), 356 (60, [M-tBu+2H]$^+$).

EXAMPLE 5

Preparation of 5-(4-fluorophenyl)-4H-pyrrolo[2,3-d]-1,3-thiazole ("A1")

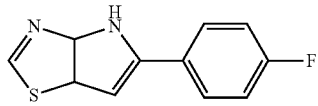 [SMILES: Fc1ccc(C2=CC3SC=NC3N2)cc1]

238 mg (0.75 mmol) of tert-butyl N-{5-[2-(4-fluorophenyl)ethynyl]-1,3-thiazol-4-yl}carbamate are dissolved in 4.5 ml of NMP in a microwave vessel, and 143 mg (1.27 mmol) of KO$^t$Bu are added. The reaction vessel is sealed under nitrogen and heated at 90° C. for 20 min in the microwave while cooling in a stream of nitrogen. The mixture is diluted with 50 ml of diethyl ether and washed with 50 ml of sat. NaCl solution. The aqueous phase is again extracted with diethyl ether. The combined organic phases are dried over sodium sulfate, evaporated in vacuo, and the residue is purified by chromatography on silica gel (eluent: cyclohexane/ethyl acetate 1/1), giving 109 mg (0.49 mmol, 66%) of 5-(4-fluorophenyl)-4H-pyrrolo[2,3-d]-1,3-thiazole as white crystals; m.p. 244-245;

$^1$H NMR (300 MHz, DMSO-d$_6$): δ [ppm] 6.87 (d, J$_{H,H}$=2.0 Hz, 1H), 7.20-7.29 (m, 2H), 7.75-7.83 (m, 2H), 8.77 (s, 1H), 12.33 (bs, 1H).

$^{13}$C NMR (100 MHz, DMSO-d$_6$): δ [ppm] 96.58, 114.59, 115.75 (d, $^2$J$_{C,F}$=19 Hz), 126.05 (d, $^3$J$_{C,F}$=7 Hz), 129.24, 135.17, 150.79, 152.97, 161.05 (d, $^1$J$_{C,F}$=250 Hz);

ESI-MS: ft: 2.28 min; m/e (%): 219 (100, [M+H]$^+$).

EXAMPLE 6

Preparation of 5-(4-fluorophenyl)-2-morpholin-4-yl-4H-pyrrolo[2,3-c]thiazole ("A12")

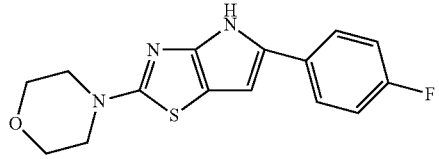 [SMILES: Fc1ccc(-c2cc3sc(N4CCOCC4)nc3[nH]2)cc1]

126 mg (0.50 mmol) of 2-chloro-5-(4-fluorophenyl)-4H-pyrrolo[2,3-d]thiazole are suspended in 2 ml of morpholine in a microwave vessel and irradiated at 130° C. for 2 h and subsequently purified directly by chromatography on silica gel (eluent: cyclohexane/ethyl acetate 1/1), giving 139 mg (0.45 mmol, 91%) of 5-(4-fluorophenyl)-2-morpholin-4-yl-4H-pyrrolo[2,3-d]thiazole as beige crystals; m.p. 240-248;

$^1$H NMR (300 MHz, DMSO-d$_6$): δ [ppm] 3.35-3.51 (m, 4H), 3.66-3.81 (m, 4H), 6.65 (d, J$_{H,H}$=1.3 Hz, 1H), 7.16 (t, J$_{H,H}$=8.9 Hz, 2H), 7.55-7.69 (m, 2H), 11.78 (s, 1H);

$^{13}$C NMR (75 MHz, DMSO-d$_6$): δ [ppm] 48.03, 65.34, 97.17, 105.45, 115.48 (d, $^2$J$_{C,F}$=21 Hz), 124.52 (d, $^3$J$_{C,F}$=7 Hz), 128.77, 129.90, 148.59, 160.11 (d, $^1$J$_{C,F}$=240 Hz), 170.62;

ESI-MS: R$_t$: 2.33 min; m/e (%): 304 (100, [M+H]$^+$).

The following compounds are obtained analogously to the examples described above

| Compound No. | Name and/or structure | m.p. [° C.]; MS |
| --- | --- | --- |
| "A3" | 4H-Pyrrolo[2,3-d]thiazole | 150-151; APCI-MS: R$_t$: 2.50 min; m/e (%): 125 (100, [M + H]$^+$) |

$^1$H NMR (300 MHz, DMSO-d$_6$): δ [ppm] 6.39 (dd, J$_{H,H}$ = 3.1 Hz, J$_{H,H}$ = 1.8 Hz, 1H), 7.12 (td, J$_{H,H}$ = 3.0 Hz, J$_{H,H}$ = 1.4 Hz, 1H), 8.73 (d, J$_{H,H}$ = 1.3 Hz, 1H), 11.79 (s, 1H);
$^{13}$C NMR (75 MHz, DMSO-d$_6$) δ [ppm] 98.83, 112.86, 122.94, 150.39, 151.94.

| Compound No. | Name and/or structure | m.p. [° C.]; MS |
|---|---|---|
| "A4" | 3-(4H-Pyrrolo[2,3-d]thiazol-5-yl)phenylamine | 160-161; ESI-MS: $R_t$: 1.57 min; m/e (%): 216 (100, [M + H]$^+$) |
| | $^1$H NMR (300 MHz, DMSO-d$_6$): δ [ppm] 5.10 (s, 2H), 6.49 (d, $J_{H,H}$ = 7.5 Hz, 1H), 6.69 (d, $J_{H,H}$ = 1.6 Hz, 1H), 6.98-6.83 (m, 3H), 7.05 (t, $J_{H,H}$ = 8.0 Hz, 1H), 8.73 (s, 1H), 12.15 (s, 1H); $^{13}$C NMR (75 MHz, DMSO-d$_6$) δ [ppm] 95.82, 109.74, 112.33, 112.90, 114.34, 129.23, 133.16, 137.13, 148.78, 150.08, 152.66. | |
| "A5" | Benzyl-[4-(4H-pyrrolo[2,3-d]thiazol-5-yl)-pyridin-2-yl]amine | ESI-MS: m/e (%): 307 (100, [M + H]$^+$) |
| "A6" | Benzyl-[3-(4H-pyrrolo[2,3-d]thiazol-5-yl)-phenyl]amine | 169-170; ESI-MS: m/e (%): 306 (100, [M + H]$^+$) |
| | $^1$H NMR (400 MHz, DMSO-d$_6$): δ [ppm] 4.34 (d, $J_{H,H}$ = 6.1 Hz, 2H), 6.27 (t, $J_{H,H}$ = 6.1 Hz, 1H), 6.51 (dd, $J_{H,H}$ = 8.0 Hz, $J_{H,H}$ = 1.5 Hz, 1H), 6.71 (d, $J_{H,H}$ = 1.9 Hz, 1H), 6.88-7.01 (m, 2H), 7.07 (t, $J_{H,H}$ = 7.8 Hz, 1H), 7.22 (t, $J_{H,H}$ = 7.3 Hz, 1H), 7.33 (t, $J_{H,H}$ = 7.6 Hz, 2H), 7.41 (d, $J_{H,H}$ = 7.6 Hz, 2H), 8.74 (s, 1H), 12.20 (s, 1H); $^{13}$C NMR (100 MHz, DMSO-d$_6$): δ [ppm] 45.83, 95.44, 107.06, 111.13, 111.73, 113.85, 126.07, 126.75, 127.72, 128.69, 132.61, 136.59, 139.79, 148.45, 149.75, 152.14. | |
| "A2" | 5-Benzyl-4H-pyrrolo[2,3-d]thiazole | m.p. 117-122; ESI-MS: m/e: 215 ([M + H]$^+$); |
| | $^1$H NMR (400 MHz, DMSO-d$_6$): δ [ppm] 3.99 (s, 2H), 6.13 (bs, 1H), 7.17-7.32 (m, 5H), 8.62 (s, 1H), 11.78 (bs, 1H); $^{13}$C NMR (100 MHz, DMSO-d$_6$): δ [ppm] 33.86, 96.48, 112.32, 125.58, 127.80, 127.90, 136.04, 139.35, 148.15, 150.93; APCI-MS: $R_t$: 3.97 min; m/e (%): 215 (100, [M + H]$^+$). | |

| Compound No. | Name and/or structure | m.p. [° C.]; MS |
|---|---|---|
| "A8" | 6-Benzyl-2-pyridin-4-yl-4H-pyrrolo[2,3-d]-thiazole | 185-187; ESI-MS: $R_t$: 1.89 min; m/e (%): 292 (100, [M + H]$^+$) |

$^1$H NMR (400 MHz, DMSO-d$_6$): δ [ppm] 3.94 (s, 2H), 7.08-7.39 (m, 6H), 7.75 (dd, $J_{H,H}$ = 4.5 Hz, $J_{H,H}$ = 1.6 Hz, 2H), 8.61 (dd, $J_{H,H}$ = 4.5 Hz, $J_{H,H}$ = 1.6 Hz, 2H), 11.86 (s, 1H);
$^{13}$C NMR (100 MHz, DMSO-d$_6$): δ [ppm] 31.87, 113.71, 114.42, 118.53, 122.03, 125.58, 127.91, 128.00, 139.68, 140.45, 150.01, 151.13, 159.15

| | | |
|---|---|---|
| "A9" | 4-(4H-Pyrrolo[2,3-d]thiazol-5-yl)pyridin-2-ylamine | ESI-MS: $R_t$: 1.27 min; m/e (%): 217 (100, [M + H]$^+$) |

$^1$H NMR (500 MHz, DMSO-d$_6$): δ [ppm] 6.05 (s, 2H), 6.51 (d, $J_{H,H}$ = 8.6 Hz, 1H), 6.66 (d, $J_{H,H}$ = 1.9 Hz, 1H), 7.75 (dd, $J_{H,H}$ = 8.6 Hz, $J_{H,H}$ = 2.4 Hz, 1H), 8.35 (d, $J_{H,H}$ = 2.2 Hz, 1H), 8.68 (d, $J_{H,H}$ = 3.5 Hz, 1H), 12.09 (s, 1H)

| | | |
|---|---|---|
| "A10" | 2-Chloro-5-(4-fluorophenyl)-4H-pyrrolo-[2,3-d]thiazole | 150-151; ESI(−)-MS: $R_t$: 2.54 min; m/e (%): 250 (100, [M − 2H]$^-$), 252 (45, [M]$^-$), 251 (20, [M − 1H]$^-$) |

$^1$H NMR (300 MHz, DMSO-d$_6$): δ [ppm] 6.83 (s, 1H), 7.13-7.35 (m, 2H), 7.66-7.90 (m, 2H), 12.48 (s, 1H);
$^{13}$C NMR (75 MHz, DMSO-d$_6$): δ [ppm] 97.24, 115.78 (d, $^2J_{C,F}$ = 21 Hz), 126.15 (d, $^3J_{C,F}$ = 7 Hz), 128.78, 134.37, 145.89, 147.25, 150.15, 161.17 (d, $^1J_{C,F}$ = 243 Hz)

| | | |
|---|---|---|
| "A11" | 5-(4-Fluorophenyl)-2-(4-fluorophenyl-ethynyl)-4H-pyrrolo[2,3-d]thiazole | >200; ESI-MS: $R_t$: 2.91 min; m/e (%): 337 (100, [M + H]$^+$) |

$^1$H NMR (400 MHz, DMSO-d$_6$): δ [ppm] 6.92 (s, 1H), 7.25-7.36 (m, 4H), 7.68-7.76 (m, 2H), 7.84 (dd, $J_{H,H}$ = 8.8 Hz, $J_{H,H}$ 5.4 Hz, 2H), 12.55 (s, 1H)

| Compound No. | Name and/or structure | m.p. [° C.]; MS |
|---|---|---|
| "A13" | 5-(4-Fluorophenyl)-2-(4-pyridin-4-ylmethyl-piperazin-1-yl)-4H-pyrrolo[2,3-d]thiazole | >170; ESI-MS: R$_t$: 1.88 min; m/e (%): 394 (100, [M + H]$^+$) |

$^1$H NMR (400 MHz, DMSO-d$_6$): δ [ppm] 2.52-2.56 (m, 4H), 3.42-3.49 (m, 5H), 3.59 (s, 2H), 6.65 (d, J$_{H,H}$ = 1.9 Hz, 1H), 7.16 (t, J$_{H,H}$ = 8.9, 2H), 7.37 (d, J$_{H,H}$ = 5.6 Hz, 2H), 7.62 (dd, J$_{H,H}$ = 8.8 Hz, J$_{H,H}$ = 5.4 Hz, 2H), 8.53 (d, J$_{H,H}$ = 5.3 Hz, 2H), 11.77 (s, 1H);
$^{13}$C NMR (100 MHz, DMSO-d$_6$): δ [ppm] 47.37, 51.16, 59.87, 96.69, 105.00, 115.00 (d, $^2$J$_{C,F}$ = 22 Hz), 120.53, 123.24, 123.94 (d, $^3$J$_{C,F}$ = 8 Hz), 128.08, 129.41, 147.64 (d, $^1$J$_{C,F}$ = 220 Hz), 148.20, 149.06, 169.79

| | | |
|---|---|---|
| "A14" | 5-[5-(4-Fluorophenyl)-4H-pyrrolo[2,3-d]-thiazol-2-yl]pyrimidin-2-ylamine | >220; ESI-MS: R$_t$: 2.20 min m/e (%): 312 (100, [M + H]$^+$) |

$^1$H NMR (400 MHz, DMSO-d$_6$): δ [ppm] 6.89 (d, J$_{H,H}$ = 1.9 Hz, 1H), 7.20 (s, 2H), 7.21-7.30 (m, 4H), 8.74 (s, 2H), 12.37 (s, 1H)

| | | |
|---|---|---|
| "A16" | tert-Butyl [5-(3-phenylprop-1-ynyl)thiazol-4-yl]carbamate | 121-122; ESI-MS: m/e (%): 259 (100, [M − tBu + 2H]$^+$), 314 (68, [M]$^+$), 315 (10, [M + H]$^+$) |

$^1$H NMR (300 MHz, DMSO-d$_6$): δ [ppm] 1.41 (s, 9H), 3.93 (s, 2H), 7.15-7.45 (m, 5H), 8.88 (s, 1H), 9.33 (s, 1H);
$^{13}$C NMR (75 MHz, DMSO-d$_6$): δ [ppm] 25.15, 27.94, 71.64, 79.12, 97.52, 126.59, 127.84, 128.43, 136.01, 150.46, 2 × 151.35, 152.64

| | | |
|---|---|---|
| "A17" | tert-Butyl (5-triethylsilanylethynylthiazol-4-yl)carbamate | 88-90; APCI-MS: R$_t$: 5.52 min; m/e (%): 282 (100, [M − tBu + 2H]$^+$), 239 (40, [M − BOC + H]$^+$), 338 (17, [M]$^+$) |

$^1$H NMR (300 MHz, DMSO-d$_6$): δ [ppm] 0.62 (dt, J$_{H,H}$ = 8.3 Hz, J$_{H,H}$ = 4.2 Hz, 6H), 0.98 (t, J$_{H,H}$ = 7.8 Hz, 9H), 1.43 (s, 9H), 8.91 (s, 1H), 9.39 (s, 1H);
$^{13}$C NMR (75 MHz, DMSO-d$_6$): δ [ppm] 3.71, 7.28, 27.91, 79.17, 94.95, 101.41, 107.65, 151.40, 152.28, 152.37

| Compound No. | Name and/or structure | m.p. [° C.]; MS |
|---|---|---|
| "A18" | tert-Butyl [5-(3-aminophenylethynyl)-thiazol-4-yl]carbamate | 166-167<br>ESI-MS: R$_t$: 1.99 min;<br>m/e (%): 316<br>(100, [M + H]$^+$) |

$^1$H NMR (400 MHz, DMSO-d$_6$): δ [ppm] 1.45 (s, 9H), 5.27 (s, 2H), 6.57-6.71 (m, 3H), 7.05 (t, J$_{H,H}$ = 7.8 Hz, 1H), 8.95 (s, 1H), 9.50 (s, 1H).
EI-MS: m/e (%): 215 (100, [M − BOC]$^+$), 315 (20, [M]$^+$);
$^{13}$C NMR (100 MHz, DMSO-d$_6$): δ [ppm] 27.45, 77.09, 78.79, 98.37, 106.73, 114.36, 115.24, 117.99, 121.57, 128.68, 148.30, 150.13, 151.64, 151.95

| Compound No. | Name and/or structure | m.p. [° C.]; MS |
|---|---|---|
| "A19" | tert-Butyl [5-(3-benzylaminophenyl-ethynyl)thiazol-4-yl]carbamate | 126-129;<br>ESI-MS: R$_t$: 2.61 min;<br>m/e (%): 250<br>(100, [M − tBu + 2H]$^+$),<br>406 (20, [M + H]$^+$) |

$^1$H NMR (400 MHz, DMSO-d$_6$): δ [ppm] 1.43 (s, 9H), 4.28 (d, J$_{H,H}$ = 6.0 Hz, 2H), 6.47 (t, J$_{H,H}$ = 6.1 Hz, 1H), 6.61-6.70 (m, 3H), 7.04-7.13 (m, 1H), 7.18-7.31 (m, 1H), 7.31-7.45 (m, 4H), 8.94 (s, 1H), 9.49 (s, 1H);
$^{13}$C NMR (100 MHz, DMSO-d$_6$): δ [ppm] 27.44, 45.61, 77.28, 78.77, 98.37, 106.61, 113.10, 113.23, 118.24, 121.67, 126.17, 126.54, 127.80, 128.67, 139.24, 148.18, 150.16, 151.70, 151.91

| Compound No. | Name and/or structure | m.p. [° C.]; MS |
|---|---|---|
| "A20" | tert-Butyl [5-(2-benzylaminopyridin-4-yl-ethynyl)thiazol-4-yl]carbamate | 185-189;<br>EI-MS: m/e (%): 57<br>(65, [CCH$_3$]$^{+\cdot}$), 105<br>(100, [C$_7$H$_7$N]$^{+\cdot}$), 306<br>(55, [M − OCOCCH$_3$]$^{+\cdot}$), 406<br>(40, [M]$^{+\cdot}$) |

$^1$H NMR (400 MHz, DMSO-d$_6$): δ [ppm] 1.44 (s, 9H), 4.48 (d, J$_{H,H}$ = 6.0 Hz, 2H), 6.49-6.59 (m, 2H), 7.20-7.29 (m, 2H), 7.31 (d, J$_{H,H}$ = 4.4 Hz, 4H), 7.98 (d, J$_{H,H}$ = 5.2 Hz, 1H), 9.01 (s, 1H), 9.68 (s, 1H);
$^{13}$C NMR (100 MHz, DMSO-d$_6$): δ [ppm] 27.43, 43.50, 78.97, 80.87, 95.75, 104.86, 108.56, 112.22, 126.05, 126.59, 127.70, 129.54, 139.70, 147.59, 151.21, 151.73, 152.89, 158.15

-continued

| Compound No. | Name and/or structure | m.p. [° C.]; MS |
|---|---|---|
| "A21" | tert-Butyl [5-(1H-pyrrolo[2,3-b]pyridin-5-yl-ethynyl)thiazol-4-yl]carbamate | >158 (decomposition); ESI-MS: $R_t$: 2.04 min; m/e (%): 341 (100, [M + H]$^+$) |

$^1$H NMR (300 MHz, DMSO-d$_6$): δ [ppm] 1.47 (s, 9H), 6.50 (d, $J_{H,H}$ = 3.4 Hz, 1H), 7.41-7.67 (m, 2H), 8.11 (d, $J_{H,H}$ = 2.0 Hz, 1H), 8.34 (d, $J_{H,H}$ = 1.9 Hz, 1H), 8.96 (s, 1H), 9.54 (s, 1H), 11.93 (s, 1H);
$^{13}$C NMR (75 MHz, DMSO-d$_6$): δ [ppm] 27.95, 79.30, 97.06, 100.28, 106.89, 110.16, 119.11, 127.66, 130.63, 144.87, 146.02, 147.54, 150.75, 152.10, 152.43

| | | |
|---|---|---|
| "A22" | 5-(1H-Pyrrolo[2,3-b]pyridin-5-ylethynyl)-thiazol-4-ylamine | ESI-MS: m/e (%): 241 (100, [M + H]$^+$) |

| | | |
|---|---|---|
| "A23" | tert-Butyl (2-pyridin-4-ylthiazol-4-yl)-carbamate | 192-193; EI-MS: m/e (%): 57 (100, [CCH$_3$]$^{+\bullet}$), 177 (80, [M − BOC]$^{+\bullet}$), 277 (10, [M ]$^{+\bullet}$). ESI-MS: m/e (%): 278 (100, [M + H]$^+$) |

$^1$H NMR (300 MHz, DMSO-d$_6$): δ [ppm] 1.49 (s, 9H), 7.45 (s, 1H), 7.81 (dd, $J_{H,H}$ = 4.5 Hz, $J_{H,H}$ = 1.6 Hz, 2H), 8.70 (dd, $J_{H,H}$ = 4.5 Hz, $J_{H,H}$ = 1.6 Hz, 2H), 10.38 (s, 1H);
$^{13}$C NMR (75 MHz, DMSO-d$_6$): δ [ppm] 27.98, 79.64, 101.56, 119.47, 139.30, 149.91, 150.68, 152.76, 161.16

| | | |
|---|---|---|
| "A24" | tert-Butyl N-(2-pyridin-4-yl-5-iodo-1,3-thiazol-4-yl)carbamate | 197; EI-MS: m/e (%): 57 (100, [CCH$_3$]$^{+\bullet}$), 303 (80, [M− BOC]$^{+\bullet}$), 403 (10, [M ]$^{+\bullet}$) |

$^1$H NMR (400 MHz, DMSO-d$_6$): δ [ppm] 1.46 (s, 9H), 7.80 (dd, $J_{H,H}$ = 4.5 Hz, $J_{H,H}$ = 1.6 Hz, 2H), 8.72 (dd, $J_{H,H}$ = 5.9 Hz, $J_{H,H}$ = 1.5 Hz, 2H), 9.27 (s, 1H);
$^{13}$C NMR (100 MHz, DMSO-d$_6$): δ [ppm] 27.52, 73.10, 78.88, 118.88, 138.16, 150.32, 152.32, 165.41

-continued

| Compound No. | Name and/or structure | m.p. [° C.]; MS |
|---|---|---|
| "A25" | tert-Butyl [5-(3-morpholin-4-ylprop-1-ynyl)-2-pyridin-4-ylthiazol-4-yl]carbamate | 94-100; ESI-MS: $R_t$: 1.37 min; m/e (%): 401 (100, [M + H]$^+$) |
| "A26" | tert-Butyl {5-[3-(1,3-dioxo-1,3-dihydro-isoindol-2-yl)prop-1-ynyl]thiazol-4-yl}-carbamate | 132-141; ESI-MS: $R_t$: 2.19 min; m/e (%): 328 (100, [M − tBu + 2H]$^+$), 384 (15, [M + H]$^+$) |

$^1$H NMR (400 MHz, DMSO-d$_6$): δ [ppm] 1.33 (s, 9H), 4.65 (s, 2H), 7.84-7.96 (m, 4H), 8.91 (s, 1H), 9.44 (s, 1H);
$^{13}$C NMR (100 MHz, DMSO-d$_6$): δ [ppm] 27.16, 27.29, 71.37, 78.69, 92.47, 105.53, 122.81, 130.95, 134.18, 150.82, 151.78, 151.97, 166.11

| | | |
|---|---|---|
| "A27" | 3-(4-Aminothiazol-5-ylethynyl)phenol | ESI-MS: $R_t$: 1.83 min; m/e (%): 217 (100, [M + H]$^+$) |
| "A28" | tert-Butyl [2-(2-aminopyridin-3-yl)-5-(4-fluorophenylethynyl)thiazol-4-yl]carbamate | ESI-MS: $R_t$: 3.32 min; m/e (%): 411 (100, [M + H]$^+$) |

$^1$H NMR (400 MHz, DMSO-d$_6$): δ [ppm] 1.48 (s, 9H), 6.67 (dd, $J_{H,H}$ = 7.7 Hz, $J_{H,H}$ = 4.7 Hz, 1H), 7.35-7.25 (m, 2H), 7.58-7.67 (m, 4H), 7.90 (dd, J = 7.7 Hz, $J_{H,H}$ = 1.7 Hz, 1H), 8.13 (dd, $J_{H,H}$ = 4.7 Hz, $J_{H,H}$ = 1.7 Hz, 1H), 9.89 (s, 1H);
$^{13}$C NMR (100 MHz, DMSO-d$_6$): δ [ppm] 27.43, 78.41, 79.32, 97.25, 100.85, 108.17, 111.68, 115.55 (d, $^2J_{C,F}$ = 23 Hz), 118.02, 132.90 (d, $^3J_{C,F}$ = 8 Hz), 135.56, 149.33, 150.59, 151.41, 155.11, 161.62 (d, $^1J_{C,F}$ = 247 Hz), 162.98

| Compound No. | Name and/or structure | m.p. [° C.]; MS |
|---|---|---|
| "A30" | 3-[5-(4-Fluorophenyl)-4H-pyrrolo[2,3-d]-thiazol-2-yl]pyridin-2-ylamine | 300-301;<br>ESI-MS: R$_t$: 1.95 min;<br>m/e (%): 311<br>(100, [M + H]$^+$) |
| "A31" | 3-[5-(4-Fluorophenyl)-4H-pyrrolo[2,3-d]-thiazol-2-yl]-5-(1-piperidin-4-yl-1H-pyrazol-4-yl)pyridin-2-ylamine | >230°(decomposition)<br>ESI-MS: R$_t$: 1.70 min;<br>$^\$$ m/e (%): 460 (100, [M + H]$^+$);<br>ESI-HRMS: R$_t$: 4.55 min, m/e [M + H]$^+$;<br>calculated for C$_{24}$H$_{23}$FN$_7$S: 460.1719;<br>found: 460.1704 |

$^1$H NMR (400 MHz, DMSO-d$_6$): δ [ppm] 2.30-2.13 (m, 4H), 3.17-3.08 (m, 2H), 3.45-3.40 (m, 2H), 4.57-4.50 (m, 1H), 7.02 (d, J = 1.7 Hz, 1H), 7.32 (d, J = 8.9 Hz, 2H), 7.86 (d, J = 3.4 Hz, 2H), 8.06 (s, 1H), 8.33 (s, 1H), 8.39 (d, J = 1.9 Hz, 1H), 8.41 (s, 1H), 12.58 (s, 1H);

$^{13}$C NMR (100 MHz, DMSO-d$_6$): δ [ppm] = 28.03, 41.33, 54.87, 94.87, 96.83, 115.3 (d, $^2$J$_{C,F}$ = 22 Hz), 115.86, 115.98, 117.9, 125.6, 125.9 (d, $^3$J$_{C,F}$ = 7 Hz), 128.0, 135.8, 135.6, 136.5, 148.6, 150.9, 157.9, 159.6, 160.9 (d, $^1$J$_{C,F}$ = 250 Hz)

| | | |
|---|---|---|
| "A32" | 6-(4,4-Dimethylpent-2-ynyl)-4H-pyrrolo-[2,3-d]thiazole | 116-118;<br>ESI-MS: R$_t$: 2.40 min;<br>$^\$$ m/e (%): 219 (100, [M + H]$^+$);<br>ESI-HRMS: R$_t$: 6.19 min m/e [M + H]$^+$; m/e calculated for C$_{12}$H$_{15}$N$_2$S: 219.0956;<br>found: 219.0951 |

$^1$H NMR (300 MHz, DMSO-d$_6$): δ [ppm] = 1.21 (d, J = 8.6 Hz, 9H), 2.51 (dd, J = 3.6 Hz, 1.8 Hz, 1H), 3.52 (d, J = 0.7 Hz, 2H), ), 6.94 (dd, J = 2.3 Hz, 1.2 Hz, 1H), 8.72 (d, J = 1.3 Hz, 1H), 11.58 (s, 1H);

$^{13}$C NMR (75 MHz, DMSO-d$_6$): δ [ppm] = 16.27, 26.99, 31.03, 76.00, 89.60, 109.98, 112.08, 119.57, 150.62, 151.57

| Compound No. | Name and/or structure | m.p. [° C.]; MS |
|---|---|---|
| "A33" | Methyl 2-tert-butyl-3-(4H-pyrrolo[2,3-d]-thiazol-6-ylmethyl)-1H-indole-5-carboxylate<br>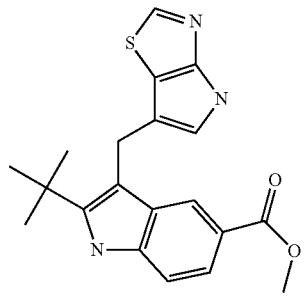 | >167 (decomposition); ESI-MS: $R_t$: 2.42 min; $^\$$ m/e (%): 368 (100, [M + H]$^+$); ESI-HRMS: $R_t$: 6.08 min, m/e [M + H]$^+$; m/e calculated for $C_{20}H_{22}N_3O_2S$: 368.1432; found: 368.1425 |

$^1$H NMR (300 MHz, DMSO-d$_6$): δ [ppm] = 1.46 (s, 9H), 3.83 (s, 3H), 4.27 (s, 2H), 6.93 (d, J = 1.0 Hz, 2H), 7.45 (d, J = 8.5 Hz, 1H), 7.72 (dd, J = 8.5 Hz, J = 1.6, 1H), 8.07 (d, J = 1.4 Hz, 1H), 8.54 (d, J = 1.3 Hz, 1H), 11.01 (s, 1H), 11.53 (s, 2H);

$^{13}$C NMR (75 MHz, DMSO-d$_6$): δ [ppm] = 21.72, 30.39, 33.26, 51.41, 107.98, 110.48, 114.55, 119.34, 119.44, 120.26, 120.79, 121.46, 121.62, 125.43, 129.12, 137.42, 144.72, 150.12

| | | |
|---|---|---|
| "A34" | 2-tert-Butyl-3-(4H-pyrrolo[2,3-d]thiazol-6-ylmethyl)-1H-pyrrolo[2,3-b]pyridine<br>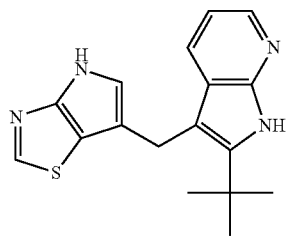 [SMILES: CC(C)(C)c1[nH]c2ncccc2c1Cc1c[nH]c2ncsc12] | 220-225; ESI-MS: $R_t$: 1.77 min; $^\$$ m/e (%): 311 (100, [M + H]$^+$); EI-HRMS: m/e calculated for $C_{17}H_{18}N_4S$: 310.1252; found: 310.1201 |

$^1$H NMR (300 MHz, DMSO-d$_6$): δ [ppm] = 1.41 (s, 9H), 4.16 (s, 2H), 6.97-6.84 (m, 2H), 7.67 (dd, J = 7.8 Hz, J = 1.2 Hz, 1H), 8.10 (s, 1H), 8.50 (d, J = 1.3 Hz, 1H), 11.10 (s, 1H), 11.46 (s, 1H);

$^{13}$C NMR (75 MHz, DMSO-d$_6$): δ [ppm] = 21.79, 30.44, 33.55, 39.53, 105.35, 112.15, 114.57, 114.66, 119.39, 121.73, 125.50, 141.45, 143.57, 147.63, 150.03, 151.37

| | | |
|---|---|---|
| "A35" | 6-(3,5-Difluorobenzyl)-4H-pyrrolo-[2,3-d]thiazole<br>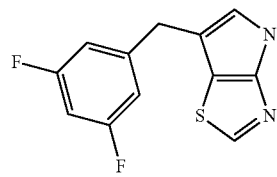 | ESI-MS: $R_t$: 4.49 min; $^\S$ [M]$^+$ 251 |

$^1$H NMR (400 MHz, CDCl$_3$) δ [ppm] 8.61 (br. s, 1H), 8.48 (d, J = 1.3, 1H), 6.89 (d, J = 1.0, 1H), 6.83-6.74 (m, 2H), 6.67 (m, 1H), 3.96 (s, 2H)

-continued

| Compound No. | Name and/or structure | m.p. [° C.]; MS |
|---|---|---|
| "A36" | 6-(4-Methoxybenzyl)-4H-pyrrolo-[2,3-d]thiazole<br><br>¹H NMR (400 MHz, CDCl₃) δ [ppm] 8.66 (br. s, 1H), 8.50 (s, 1H), 7.19 (d, J = 8.5, 2H), 6.87 (d, J = 8.5, 2H), 3.91 (s, 2H), 3.81 (s, 3H) | ESI-MS: R$_t$: 4.123 min;<br>§ [M]⁺ 245 |
| "A37" | 6-(4-Bromobenzyl)-4H-pyrrolo[2,3-d]thiazole<br><br>¹H NMR (400 MHz, CDCl₃) δ [ppm] 8.61 (br. s, 1H), 8.47 (s, 1H), 7.46-7.41 (m, 2H), 7.15 (d, J = 8.4, 2H), 6.86 (s, 1H), 3.94 (s, 2H) | ESI-MS: R$_t$: 4.793 min;<br>§ [M]⁺ 293 |
| "A38" | 6-(4-Isopropylbenzyl)-4H-pyrrolo-[2,3-d]thiazole<br><br>¹H NMR (400 MHz, CDCl₃) δ [ppm] 9.10 (br. s, 1H), 8.52 (d, J = 1.2, 1H), 7.27 (s, 5H), 7.19 (s, 4H), 6.90 (d, J = 1.0, 1H), 3.95 (s, 2H), 2.90 (quint, J = 6.9, 1H), 1.25 (d, J = 6.9, 6H) | ESI-MS: R$_t$: 5.225 min;<br>§ [M]⁺ 257 |
| "A39" | 6-(4-Bromo-2-fluorobenzyl)-4H-pyrrolo-[2,3-d]thiazole<br><br>¹H NMR (400 MHz, CDCl₃) δ [ppm] 8.56 (br. s, 1H), 8.47 (d, J = 1.3, 1H), 7.24 (t, J = 8.8, 2H), 7.11 (t, J = 7.9, 1H), 6.88 (s, 1H), 3.96 (s, 2H) | ESI-MS: R$_t$: 4.837 min;<br>§ [M]⁺ 311 |
| "A40" | 6-(4-tert-Butylbenzyl)-4H-pyrrolo-[2,3-d]thiazole<br><br>¹H NMR (400 MHz, CDCl₃) δ [ppm] 8.59 (br. s, 1H), 8.46 (s, 1H), 7.39-7.31 (m, 2H), 7.21 (d, J = 8.3, 2H), 6.85 (d, J = 1.1, 1H), 3.95 (s, 2H), 1.32 (s, 9H) | ESI-MS: R$_t$: 5.439 min;<br>§ [M]⁺ 271.3 |

| Compound No. | Name and/or structure | m.p. [° C.]; MS |
|---|---|---|
| "A41" | 6-(2-Chlorobenzyl)-4H-pyrrolo-[2,3-d]thiazole | ESI-MS: R$_t$: 4.581 min; § [M]$^+$ 249 |

$^1$H NMR (400 MHz, CDCl$_3$) δ [ppm] 9.11 (br. s, 1H), 8.51 (s, 1H), 7.40 (dd, J = 7.3, 2.0, 1H), 7.29 (dd, J = 7.3, 2.3, 1H), 7.25-7.21 (m, 1H), 7.21-7.17 (m, 1H), 6.92 (d, J = 1.1, 1H), 4.11 (s, 2H)

| | | |
|---|---|---|
| "A42" | 6-(4-Fluorobenzyl)-4H-pyrrolo[2,3-d]thiazole | ESI-MS: R$_t$: 4.37 min; § [M]$^+$ 233 |

$^1$H NMR (400 MHz, CDCl$_3$) δ [ppm] 8.65 (br. s, 1H), 8.46 (s, 1H), 7.25-7.20 (m, 2H), 7.04-6.96 (m, 2H), 6.85 (d, J = 1.0, 1H), 3.96 (s, 2H)

| | | |
|---|---|---|
| "A43" | 6-(3-Fluorobenzyl)-4H-pyrrolo-[2,3-d]thiazole | ESI-MS: R$_t$: 4.367 min; § [M]$^+$ 233 |

$^1$H NMR (400 MHz, CDCl$_3$) δ [ppm] 8.80 (br. s, 1H), 8.49 (s, 1H), 7.29 (dd, J = 7.0, 5.2, 1H), 7.06 (d, J = 7.5, 1H), 6.99-6.90 (m, 2H), 6.89 (d, J = 1.0, 1H), 3.98 (s, 2H)

| | | |
|---|---|---|
| "A44" | 6-(2,3-Difluorobenzyl)-4H-pyrrolo-[2,3-d]thiazole | ESI-MS: RT: 4.454 min; § [M]$^+$ 251 |

$^1$H NMR (400 MHz, CDCl$_3$) δ [ppm] 8.95 (s, 1H), 8.51 (s, 1H), 7.04 (m, 3H), 6.93 (s, 1H), 4.04 (s, 2H)

| Compound No. | Name and/or structure | m.p. [° C.]; MS |
|---|---|---|
| "A45" | 6-(2,4-Difluorobenzyl)-4H-pyrrolo-[2,3-d]thiazole | ESI-MS: RT: 4.488 min; § [M]+ 251 |
| | $^1$H NMR (400 MHz, CDCl$_3$) δ [ppm] 8.92 (s, 1H), 8.49 (s, 1H), 7.24-7.16 (m, 1H), 6.87 (m, 1H), 6.82 (m, 1H), 3.96 (s, 2H) | |
| "A46" | 6-(2,5-Difluorobenzyl)-4H-pyrrolo-[2,3-d]thiazole | ESI-MS: RT: 4.438 min; § [M]+ 251 |
| | $^1$H NMR (400 MHz, CDCl$_3$) δ [ppm] 9.54 (s, 1H), 8.63 (s, 1H), 7.07-7.00 (m, 1H), 6.99 (s, 1H), 6.95-6.88 (m, 2H), 3.99 (s, 2H) | |
| "A47" | 6-(3,4-Difluorobenzyl)-4H-pyrrolo-[2,3-d]thiazole | ESI-MS: RT: 4.508 min; § [M]+ 251 |
| | $^1$H NMR (400 MHz, CDCl$_3$) δ [ppm] 8.93 (s, 1H), 8.52 (s, 1H), 7.13-7.06 (m, 1H), 7.07-7.02 (m, 1H), 6.99 (s, 1H), 6.91 (s, 1H), 3.95 (s, 2H) | |
| "A48" | 6-(6-Chloropyridin-3-ylmethyl)-4H-pyrrolo-[2,3-d]thiazole | ESI-MS: RT: 3.549 min; § [M]+ 250 |
| | $^1$H NMR (400 MHz, CDCl$_3$) δ [ppm] 9.17 (s, 1H), 8.55 (s, 1H), 8.36 (d, J = 2.3, 1H), 7.55 (dd, J = 8.2, 2.5, 1H), 7.29 (d, J = 8.4, 1H), 6.92 (s, 1H), 3.99 (s, 2H) | |

| Compound No. | Name and/or structure | m.p. [° C.]; MS |
|---|---|---|
| "A49" | 6-(3-Chlorobenzyl)-4H-pyrrolo-[2,3-d]thiazole 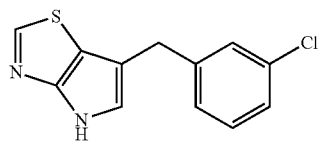 | ESI-MS: RT: 4.679 min; §[M]+ 249 |
| | ¹H NMR (400 MHz, CDCl₃) δ [ppm] 8.56 (br. s, 1H), 8.46 (d, J = 1.4, 1H), 7.27-7.25 (m, 1H), 7.23 (m, 2H), 7.17 (m, 1H), 6.87 (m, 1H), 3.96 (s, 2H) | |
| "A50" | 6-(3,4-Dichlorobenzyl)-4H-pyrrolo-[2,3-d]thiazole 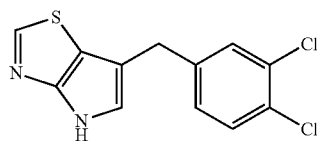 | ESI-MS: RT: 5.029 min; §[M]+ 283 |
| | ¹H NMR (400 MHz, CDCl₃) δ [ppm] 9.06 (br. s, 1H), 8.52 (s, 1H), 7.37 (dd, J = 10.3, 5.1, 2H), 7.11 (dd, J = 8.2, 2.0, 1H), 6.89 (s, 1H), 3.94 (s, 2H) | |

6-benzyl-2-pyridin-3-yl-4H-pyrrolo[2,3-d]thiazole ("A51")

$^1$H NMR (400 MHz, DMSO-d$_6$) δ [ppm] 11.77 (s, 1H), 9.02 (d, J=2.2, 1 H), 8.55 (dd, J=4.8, 1.5, 1 H), 8.20-8.09 (m, 1H), 7.46 (dd, J=8.0, 4.8, 1 H), 7.31 (m, 1H), 7.27 (m, 3H), 7.20 (m, 1H), 7.09 (d, J=2.4, 1H), 3.92 (s, 2H);

6-benzyl-2-(1-methyl-1H-pyrazol-4-yl)-4H-pyrrolo[2,3-d]thiazole ("A52")

$^1$H NMR (400 MHz, DMSO-d$_6$) δ [ppm] 11.46 (s, 1H), 8.18 (s, 1H), 7.78 (d, J=0.7, 1 H), 7.31-7.22 (m, 4H), 7.21-7.15 (m, 1H), 6.90 (d, J=2.4, 1H), 3.87 (s, 2H), 3.84 (s, 3H);

5-(6-benzyl-4H-pyrrolo[2,3-d]thiazol-2-yl)pyridin-2-ylamine ("A53")

$^1$H NMR (400 MHz, DMSO-d$_6$) δ [ppm] 11.49 (d, J=2.0, 1 H), 8.37 (d, J=2.2, 1 H), 7.75 (dd, J=8.7, 2.5, 1 H), 7.28 (m, 4H), 7.18 (m, 1H), 6.91 (d, J=2.4, 1H), 6.47 (dd, J=8.8, 0.4, 1H), 6.41 (s, 2H), 3.87 (s, 2H);

6-prop-2-ynyl-4H-pyrrolo[2,3-d]thiazole ("A54")

$^1$H NMR (400 MHz, CDCl₃) δ [ppm] 8.63 (s, 1H), 8.53 (d, J=1.1, 1H), 6.98 (d, J=1.2, 1H), 3.62 (d, J=2.0, 3H), 2.19 (t, J=2.6, 1H);

3-(6-benzyl-4H-pyrrolo[2,3-d]thiazol-2-yl)pyridin-2-ylamine ("A55"), 6-benzyl-2-(1H-pyrazol-4-yl)-4H-pyrrolo[2,3-d]thiazole ("A56"), 6-benzyl-2-(5-bromopyridin-3-yl)-4H-pyrrolo[2,3-d]thiazole ("A57"), 6-benzyl-2-pyrimidin-5-yl-4H-pyrrolo[2,3-d]thiazole ("A58"), morpholin-4-yl-[3-(4H-pyrrolo[2,3-d]thiazol-6-ylmethyl)-1H-indol-5-yl]-methanone ("A59"), N-(2-methoxyethyl)-3-(4H-pyrrolo[2,3-d]thiazol-6-ylmethyl)-1H-indole-5-carboxamide ("A60"), N-(4-fluorobenzyl)-3-(4H-pyrrolo[2,3-d]thiazol-6-ylmethyl)-1H-indole-5-carboxamide ("A61"), N-(2-aminoethyl)-2-[4-(4H-pyrrolo[2,3-d]thiazol-6-ylmethyl)-1,2,3-triazol-1-yl]acetamide ("A62"), 1-piperazin-1-yl-2-[4-(4H-pyrrolo[2,3-d]thiazol-6-ylmethyl)-1,2,3-triazol-1-yl]ethanone ("A63"), N-(piperidin-4-yl)-2-[4-(4H-pyrrolo[2,3-d]thiazol-6-ylmethyl)-1,2,3-triazol-1-yl]acetamide ("A64"), 6-(1-pyridin-3-ylmethyl-1H-1,2,3-triazol-4-ylmethyl) 4H-pyrrolo[2,3-d]-thiazole ("A65"), $^1$H NMR (400 MHz, CDCl₃) δ [ppm] 8.61 (dd, J=4.8, 1.5, 1H), 8.58 (d, J=1.9, 2H), 8.47 (d, J=1.3, 1 H), 7.58 (d, J=8.4, 1 H), 7.31 (dd, J=7.8, 4.8, 1H), 7.25 (s, 1H), 6.93 (d, J=1.1, 1H), 5.53 (s, 2H), 4.11 (s, 2H);

6-(1-pyridin-4-ylmethyl-1H-1,2,3-triazol-4-ylmethyl) 4H-pyrrolo[2,3-d]-thiazole ("A66")

$^1$H NMR (400 MHz, CDCl₃) δ [ppm] 8.61 (dd, J=4.4, 1.6, 3H), 8.48 (d, J=1.3, 1H), 7.09 (dd, J=4.5, 1.5, 2H), 6.96 (d, J=1.1, 1H), 5.53 (s, 2H), 4.14 (s, 2H);

6-benzyl-2-(5-(1-methyl-1H-pyrazol-4-yl)pyridin-3-yl)-4H-pyrrolo[2,3-d]thiazole ("A67"), 6-benzyl-2-(5-(1H-pyrazol-4-yl)pyridin-3-yl)-4H-pyrrolo[2,3-d]thiazole ("A68"), 6-benzyl-2-(5-(4-fluorophenyl)pyridin-3-yl)-4H-pyrrolo[2,3-d]thiazole ("A69"), 6-(5-methanesulfonylthiophen-2-ylmethyl)-4H-pyrrolo[2,3-d]thiazole ("A70"), 6-[1-(2-morpholin-4-ylethyl)-1H-1,2,3-triazol-4-ylmethyl) 4H-pyrrolo[2,3-d]-thiazole ("A71")

$^1$H NMR (400 MHz, CDCl₃) δ [ppm] 8.57 (s, 1H), 8.49 (d, J=1.3, 1H), 7.42 (s, 1H), 6.96 (d, J=1.1, 1 H), 4.43 (t, J=6.3, 2H), 4.12 (s, 2H), 3.71-3.60 (m, 5H), 2.80 (t, J=6.3, 2H), 2.53-2.42 (m, 4H);

6-benzyl-2-{5-[1-((E)-3-phenylallyl)-1H-pyrazol-4-yl]pyridin-3-yl}-4H-pyrrolo-[2,3-d]thiazole ("A72")

$^1$H NMR (400 MHz, DMSO-d$_6$) δ [ppm] 11.47 (s, 1H), 8.27 (s, 1H), 7.85 (d, J=0.6, 1H), 7.45 (d, J=7.1, 2H), 7.36-7.22 (m, 7H), 7.21-7.15 (m, 1H), 6.91 (d, J=2.4, 1H), 6.59 (d, J=16.0, 1H), 6.51 (t, J=6.1, 1H), 4.92 (d, J=5.9, 2H), 3.87 (s, 2H).

Results of the Receptor Binding Tests

The compounds shown here were tested at a concentration of 1 μM against 102 kinases. As shown by the comparison, both the compounds of the formula Ia and also those of the formula Ib are associated with a high degree of potency and selectivity, making them suitable for use in targeted tumour therapy.

The % values indicated are a measure of the residual kinase activity remaining if the kinase is treated with the substance under the conditions described in the filter binding assay. Within the bounds of measurement accuracy, it can be assumed that a % value of about 50 corresponds to an $IC_{50}$ of 10 μM. W. Karaman et al. in Nature Biotechnology 2008; 26 (1): 127-32, describe the quantitative analysis of kinase inhibitor selectivity.

Some compounds according to the invention are shown by way of example below along with the kinases which inhibits the substance to the extent of about 50% or greater:

6-benzyl-4H-pyrrolo[2,3-d]thiazole ("A7")
Aurora A (33%); Rock II (36%); CDK2 (41%); CK2 (53%); NUAK1 (27%);
3-(4-aminothiazol-5-ylethynyl)phenol ("A27")
Nek2A (59%); NUAK1 (49%);
tert-butyl{5-[3-(1,3-dioxo-1,3-dihydroisoindol-2-yl)prop-1-ynyl]-thiazol-4-yl}carbamate ("A26")
CDK2 (28%); NUAK1 (24%);
tert-butyl[5-(3-morpholin-4-ylprop-1-ynyl)-2-pyridin-4-ylthiazol-4-yl]-carbamate ("A25")
HIPK1 (48%);
5-(1H-pyrrolo[2,3-b]pyridin-5-ylethynyl)thiazol-4-ylamine ("A22")
Aurora A (39%); HIPK1 (36%); MARK2 (31%); MKK1 (43%); PDK1 (53%); GSK3b (9%); CHK1 (40%); CDK2 (52%); PRK2 (38%); MAPK8 (34%); MARK3 (15%); HIPK2 (44%); PAK-4 (34%); VEGFR (11%); GCK 31%); NUAK1 (16%); MLK3 (23%).

If it is furthermore assumed that the kinase inhibitors behave normally in the activity measurement concentration range considered, a regression line having a slope of 1 can be assumed for this range considered. $IC_{50}$ values shown below for the compounds can thus be obtained for a multiplicity of kinases.

$IC_{50}$: 10 nM-1 μM=A; 1 μM-10 μM=B; 10 μM-100 μM=C

NA here means that the compound has exerted absolutely no inhibitory effects on the kinase (no activity) at the test concentration of 1 μM.

It can be seen from the table with the $IC_{50}$ values derived from the % inhibition data that the compounds presented here provide an extremely high measure of flexible kinase inhibition.

| Kinase | "A26" | "A7" | "A27" | "A22" | "A25" | "A31" |
|---|---|---|---|---|---|---|
| MAP2K1 | B | B | NA | A | B | |
| SRC | C | B | B | C | B | |
| MAPK1 | C | NA | B | C | NA | |
| MAPK8 | C | B | B | B | NA | |
| MAPK14 | C | B | B | C | C | |
| MAPK11 | NA | B | B | NA | NA | |
| MAPK12 | C | NA | B | B | C | |
| MAPK13 | C | B | B | C | NA | |
| RPS6KA1 | NA | C | NA | NA | C | |
| MAPKAPK2 | C | NA | C | NA | NA | |
| RPS6KA5 | NA | B | C | C | C | |
| MAPKAPK5 | B | NA | C | C | NA | |
| PRKCA | B | C | NA | B | C | |
| PDPK1 | B | NA | NA | B | NA | |
| AKT1 | NA | NA | NA | C | NA | |
| SGK | B | NA | NA | B | C | |
| RPS6KB1 | NA | B | B | B | NA | |
| GSK3B | B | B | B | A | NA | |
| ROCK2 | NA | A | C | NA | C | |
| PRKAA1 | C | C | B | C | C | |
| CHEK1 | C | NA | C | A | C | |
| CSNK2A1 | C | NA | NA | NA | NA | |
| CSK | C | B | C | C | NA | |
| CDK2 | A | A | C | B | C | |
| CSNK1D | NA | B | B | C | NA | |
| NEK6 | C | C | C | NA | B | |
| NEK2 | B | NA | B | NA | B | |
| LCK | NA | C | B | NA | NA | |
| PRKACA | C | NA | B | B | NA | |
| PBK | C | NA | NA | B | NA | |
| RPS6KA3 | NA | B | B | C | NA | |
| IKBKB | NA | B | B | C | NA | |
| MYLK | NA | NA | B | NA | NA | |
| PKN2 | B | B | C | A | NA | |
| MKNK2 | C | NA | NA | NA | NA | |
| CAMK1 | NA | B | B | C | B | |
| PIM2 | NA | NA | B | C | B | |
| MAPK10 | NA | NA | B | NA | NA | |
| MAPKAPK3 | NA | NA | C | NA | C | |
| MAPK8 | B | NA | NA | A | NA | |
| MKNK1 | NA | NA | C | C | NA | |
| SRPK1 | NA | C | B | NA | NA | |
| AKT2 | NA | NA | B | NA | B | |
| AURKB | NA | B | C | C | NA | |
| CHEK2 | NA | NA | C | NA | NA | |
| EEF2K | C | C | B | C | NA | |
| MARK3 | B | B | C | A | NA | |
| STK3 | NA | B | B | C | NA | |
| PRKD2 | NA | B | B | NA | NA | |
| MAPK9 | NA | C | B | NA | NA | |
| DYRK3 | B | C | C | C | C | |
| HIPK2 | B | NA | NA | A | NA | |
| HIPK3 | C | B | B | B | C | |
| PAK4 | B | NA | NA | A | NA | |
| DYRK2 | NA | NA | B | NA | NA | |
| CAMKK2 | C | C | C | NA | NA | |
| PIM1 | C | C | B | B | NA | |
| PIM3 | NA | B | B | C | NA | |
| PAK6 | NA | NA | C | C | C | |
| PLK1 | NA | NA | C | B | NA | |
| BRSK2 | NA | NA | C | NA | NA | |
| MELK | NA | B | B | NA | NA | |
| PRKCZ | C | NA | NA | NA | C | |
| MAPK1 | C | C | NA | B | C | |
| FGFR1 | B | B | NA | B | NA | |
| INSRR | B | NA | NA | B | NA | |
| EPHA2 | NA | C | NA | NA | NA | |
| MST4 | C | NA | NA | B | NA | |
| SYK | NA | NA | C | C | NA | |
| YES1 | NA | NA | NA | B | NA | |
| IGF1R | NA | C | NA | B | NA | |
| KDR | NA | B | B | A | NA | |
| BTK | NA | C | C | C | C | |
| INSR | B | NA | C | C | NA | |
| EPHB3 | B | NA | B | C | NA | |
| TBK1 | NA | NA | NA | NA | C | A |
| IKBKE | C | C | NA | NA | B | |
| NUAK1 | A | A | A | A | C | |
| MAP3K9 | B | B | B | B | NA | |
| MINK1 | C | B | B | B | C | |
| MAP4K2 | B | B | B | A | NA | |
| IRAK4 | C | NA | C | NA | C | |
| TTK | C | C | C | C | C | |
| DYRK1A | C | NA | C | NA | NA | |
| MAP3K11 | B | C | C | A | NA | |
| STK11 | C | C | NA | NA | NA | |
| ERBB4 | NA | C | B | NA | NA | |
| PAK2 | NA | B | NA | NA | NA | |
| BRSK1 | NA | B | B | B | NA | |
| AURKA | B | A | B | A | NA | |
| RIPK2 | C | C | B | B | NA | |
| HIPK1 | NA | NA | B | A | A | |

-continued

| Kinase | "A26" | "A7" | "A27" | "A22" | "A25" | "A31" |
|---|---|---|---|---|---|---|
| MARK4 | NA | NA | B | C | C | |
| MARK2 | B | C | C | A | NA | |
| MET | NA | B | C | NA | NA | |
| TGFBR1 | C | C | B | C | B | |
| PDPK1 | C | NA | NA | B | NA | |

The following examples relate to medicaments:

EXAMPLE A

Injection Vials

A solution of 100 g of an active ingredient of the formula I and 5 g of disodium hydrogenphosphate in 3 l of bidistilled water is adjusted to pH 6.5 using 2 N hydrochloric acid, sterile filtered, transferred into injection vials, lyophilised under sterile conditions and sealed under sterile conditions. Each injection vial contains 5 mg of active ingredient.

EXAMPLE B

Suppositories

A mixture of 20 g of an active ingredient of the formula I with 100 g of soya lecithin and 1400 g of cocoa butter is melted, poured into moulds and allowed to cool. Each suppository contains 20 mg of active ingredient.

EXAMPLE C

Solution

A solution is prepared from 1 g of an active ingredient of the formula I, 9.38 g of NaH$_2$PO$_4$.2H$_2$O, 28.48 g of Na$_2$HPO$_4$.12H$_2$O and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE D

Ointment 500 mg of an active ingredient of the formula I are mixed with 99.5 g of Vaseline under aseptic conditions.

EXAMPLE E

Tablets

A mixture of 1 kg of active ingredient of the formula I, 4 kg of lactose, 1.2 kg of potato starch, 0.2 kg of talc and 0.1 kg of magnesium stearate is pressed in a conventional manner to give tablets in such a way that each tablet contains 10 mg of active ingredient.

EXAMPLE F

Dragees

Tablets are pressed analogously to Example E and subsequently coated in a conventional manner with a coating of sucrose, potato starch, talc, tragacanth and dye.

EXAMPLE G

Capsules 2 kg of active ingredient of the formula I are introduced into hard gelatine capsules in a conventional manner in such a way that each capsule contains 20 mg of the active ingredient.

EXAMPLE H

Ampoules

A solution of 1 kg of active ingredient of the formula I in 60 l of bidistilled water is sterile filtered, transferred into ampoules, lyophilised under sterile conditions and sealed under sterile conditions. Each ampoule contains 10 mg of active ingredient.

The invention claimed is:
1. A compound, which is one of the following compounds

| No. | Name and/or structure |
|---|---|
| "A31" | 3-[5-(4-Fluorophenyl)-4H-pyrrolo[2,3-d]thiazol-2-yl]-5-(1-piperidin-4-yl-1H-pyrazol-4-yl)pyridin-2-ylamine |
| "A32" | 6-(4,4-Dimethylpent-2-ynyl)-4H-pyrrolo[2,3-d]thiazole |
| "A33" | Methyl 2-tert-butyl-3-(4H-pyrrolo[2,3-d]thiazol-6-ylmethyl)-1H-indole-5-carboxylate |
| "A34" | 2-tert-Butyl-3-(4H-pyrrolo[2,3-d]thiazol-6-ylmethyl)-1H-pyrrolo[2,3-b]pyridine |
| "A35" | 6-(3,5-Difluorobenzyl)-4H-pyrrolo[2,3-d]thiazole |
| "A36" | 6-(4-Methoxybenzyl)-4H-pyrrolo[2,3-d]thiazole |
| "A37" | 6-(4-Bromobenzyl)-4H-pyrrolo[2,3-d]thiazole |
| "A38" | 6-(4-Isopropylbenzyl)-4H-pyrrolo[2,3-d]thiazole |
| "A39" | 6-(4-Bromo-2-fluorobenzyl)-4H-pyrrolo[2,3-d]thiazole |
| "A40" | 6-(4-tert-Butylbenzyl)-4H-pyrrolo[2,3-d]thiazole |
| "A41" | 6-(2-Chlorobenzyl)-4H-pyrrolo[2,3-d]thiazole |
| "A42" | 6-(4-Fluorobenzyl)-4H-pyrrolo[2,3-d]thiazole |
| "A43" | 6-(3-Fluorobenzyl)-4H-pyrrolo[2,3-d]thiazole |
| "A44" | 6-(2,3-Difluorobenzyl)-4H-pyrrolo[2,3-d]thiazole |
| "A45" | 6-(2,4-Difluorobenzyl)-4H-pyrrolo[2,3-d]thiazole |
| "A46" | 6-(2,5-Difluorobenzyl)-4H-pyrrolo[2,3-d]thiazole |
| "A47" | 6-(3,4-Difluorobenzyl)-4H-pyrrolo[2,3-d]thiazole |
| "A48" | 6-(6-Chloropyridin-3-ylmethyl)-4H-pyrrolo[2,3-d]thiazole |
| "A49" | 6-(3-Chlorobenzyl)-4H-pyrrolo[2,3-d]thiazole |
| "A50" | 6-(3,4-Dichlorobenzyl)-4H-pyrrolo[2,3-d]thiazole |
| "A51" | 6-Benzyl-2-pyridin-3-yl-4H-pyrrolo[2,3-d]thiazole |
| "A52" | 6-Benzyl-2-(1-methyl-1H-pyrazol-4-yl)-4H-pyrrolo-[2,3-d]thiazole |
| "A53" | 5-(6-Benzyl-4H-pyrrolo[2,3-d]thiazol-2-yl)pyridin-2-ylamine |
| "A54" | 6-Prop-2-ynyl-4H-pyrrolo[2,3-d]thiazole |
| "A55" | 3-(6-Benzyl-4H-pyrrolo[2,3-d]thiazol-2-yl)pyridin-2-ylamine |
| "A56" | 6-Benzyl-2-(1H-pyrazol-4-yl)-4H-pyrrolo[2,3-d]thiazole |
| "A57" | 6-Benzyl-2-(5-bromopyridin-3-yl)-4H-pyrrolo[2,3-d]thiazole |
| "A58" | 6-Benzyl-2-pyrimidin-5-yl-4H-pyrrolo[2,3-d]thiazole |
| "A59" | Morpholin-4-yl-[3-(4H-pyrrolo[2,3-d]thiazole-6-ylmethyl)-1H-indol-5-yl]methanone |
| "A60" | N-(2-Methoxyethyl)-3-(4H-pyrrolo[2,3-d]thiazole-6-ylmethyl)-1H-indole-5-carboxamide |
| "A61" | N-(4-Fluorobenzyl)-3-(4H-pyrrolo[2,3-d]thiazol-6-ylmethyl)-1H-indole-5-carboxamide |
| "A62" | N-(2-Aminoethyl)-2-[4-(4H-pyrrolo[2,3-d]thiazol-6-ylmethyl)-1,2,3-triazol-1-yl]acetamide |

| No. | Name and/or structure |
|---|---|
| "A63" | 1-Piperazin-1-yl-2-[4-(4H-pyrrolo[2,3-d]thiazol-6-ylmethyl)-1,2,3-triazol-1-yl]ethanone |
| "A64" | N-(Piperidin-4-yl)-2-[4-(4H-pyrrolo[2,3-d]thiazol-6-ylmethyl)-1,2,3-triazol-1-yl]acetamide |
| "A65" | 6-(1-Pyridin-3-ylmethyl-1H-1,2,3-triazol-4-ylmethyl) 4H-pyrrolo[2,3-d]thiazole |
| "A66" | 6-(1-Pyridin-4-ylmethyl-1H-1,2,3-triazol-4-ylmethyl) 4H-pyrrolo[2,3-d]thiazole |
| "A67" | 6-Benzyl-2-(5-(1-methyl-1H-pyrazol-4-yl)pyridin-3-yl)-4H-pyrrolo[2,3-d]thiazole |
| "A68" | 6-Benzyl-2-(5-(1H-pyrazol-4-yl)pyridin-3-yl)-4H-pyrrolo[2,3-d]thiazole |
| "A69" | 6-Benzyl-2-(5-(4-fluorophenyl)pyridin-3-yl)-4H-pyrrolo[2,3-d]thiazole |
| "A70" | 6-(5-Methanesulfonylthiophen-2ylmethyl)-4H-pyrrolo[2,3-d]thiazole |
| "A71" | 6-[1-(2-Morpholin-4-ylethyl)-1H-1,2,3-triazol-4-ylmethyl] 4H-pyrrolo[2,3-d]thiazole |
| "A72" | 6-Benzyl-2-{5-[1-((E)-3-phenylallyl)-1H-pyrazol-4-yl]pyridin-3-yl}-4H-pyrrolo[2,3-d]thiazole | or a pharmaceutically acceptable salt, tautomer or stereoisomers thereof.

2. A pharmaceutical composition comprising a compound of claim 1, and one or more pharmaceutically acceptable excipients and/or adjuvants.

3. A compound according to claim 1, or a pharmaceutically acceptable salt thereof.

4. A compound, which is one of the following compounds

| No. | Name and/or structure |
|---|---|
| "2" | tert-Butyl N-(5-iodo-1,3-thiazol-4-yl)carbamate |
| "A1" | 5-(4-Fluorophenyl)-4H-pyrrolo[2,3-d]-1,3-thiazole 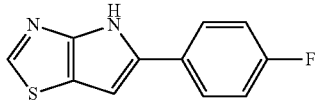 [SMILES: Fc1ccc(-c2cc3scnc3[nH]2)cc1] |
| "A2" | 5-Benzyl-4H-pyrrolo[2,3-d]thiazole |
| "A4" | 3-(4H-Pyrrolo[2,3-d]thiazol-5-yl)phenylamine 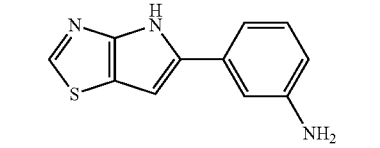 [SMILES: Nc1cccc(-c2cc3scnc3[nH]2)c1] |
| "A5" | Benzyl-[4-(4H-pyrrolo[2,3-d]thiazol-5-yl)pyridin-2-yl]amine 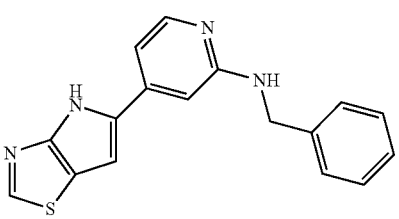 |
| "A6" | Benzyl-[3-(4H-pyrrolo[2,3-d]thiazol-5-yl)phenyl]amine |
| "A7" | 6-Benzyl-4H-pyrrolo[2,3-d]thiazole 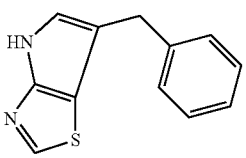 |

-continued

| No. | Name and/or structure |
|---|---|
| "A8" | 6-Benzyl-2-pyridin-4-yl-4H-pyrrolo[2,3-d]thiazole |
| "A9" | 4-(4H-Pyrrolo[2,3-d]thiazol-5-yl)pyridin-2-ylamine |
| "A10" | 2-Chloro-5-(4-fluorophenyl)-4H-pyrrolo[2,3-d]thiazole |
| "A11" | 5-(4-Fluorophenyl)-2-(4-fluorophenylethynyl)-4H-pyrrolo[2,3-d]thiazole |
| "A12" | 5-(4-Fluorophenyl)-2-morpholin-4-yl-4H-pyrrolo[2,3-d]thiazole |
| "A13" | 5-(4-Fluorophenyl)-2-(4-pyridin-4-ylmethylpiperazin-1-yl)-4H-pyrrolo[2,3-d]thiazole |
| "A14" | 5-[5-(4-Fluorophenyl)-4H-pyrrolo[2,3-d]thiazol-2-yl]pyrimidin-2-ylamine |

| No. | Name and/or structure |
|---|---|
| "A15" | tert-Butyl N-{5-[2-(4-fluorophenyl)ethynyl]-1,3-thiazol-4-yl}carbamate 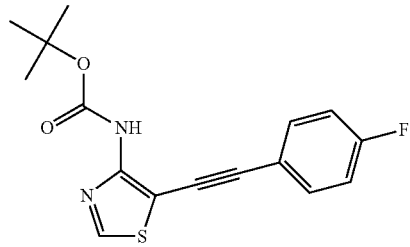 [SMILES: CC(C)(C)OC(=O)Nc1ncsc1C#Cc1ccc(F)cc1] |
| "A16" | tert-Butyl [5-(3-phenylprop-1-ynyl)thiazol-4-yl]carbamate 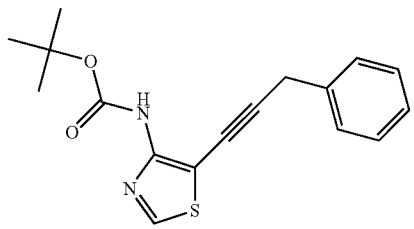 [SMILES: CC(C)(C)OC(=O)Nc1ncsc1C#CCc1ccccc1] |
| "A17" | tert-Butyl (5-triethylsilanylethynylthiazol-4-yl)carbamate 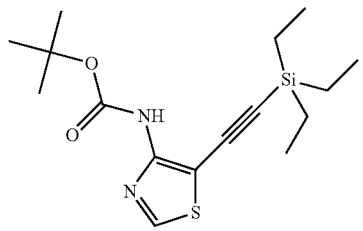 [SMILES: CC[Si](C#Cc1scnc1NC(=O)OC(C)(C)C)(CC)CC] |
| "A18" | tert-Butyl [5-(3-aminophenylethynyl)thiazol-4-yl]carbamate 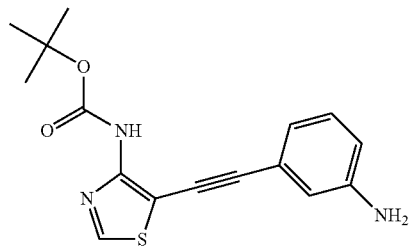 [SMILES: CC(C)(C)OC(=O)Nc1ncsc1C#Cc1cccc(N)c1] |
| "A19" | tert-Butyl [5-(3-benzylaminophenylethynyl)thiazol-4-yl]carbamate 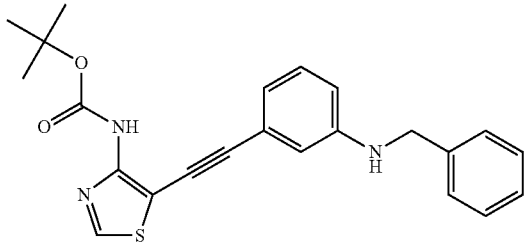 [SMILES: CC(C)(C)OC(=O)Nc1ncsc1C#Cc1cccc(NCc2ccccc2)c1] |

-continued
| No. | Name and/or structure |
|---|---|
| "A20" | tert-Butyl [5-(2-benzylaminopyridin-4-ylethynyl)thiazol-4-yl]carbamate 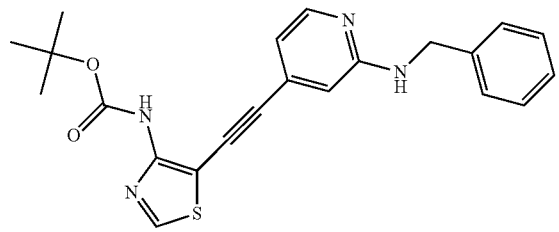 [SMILES: CC(C)(C)OC(=O)Nc1ncsc1C#Cc1ccnc(NCc2ccccc2)c1] |
| "A21" | tert-Butyl [5-(1H-pyrrolo[2,3-b]pyridin-5-ylethynyl)thiazol-4-yl]carbamate 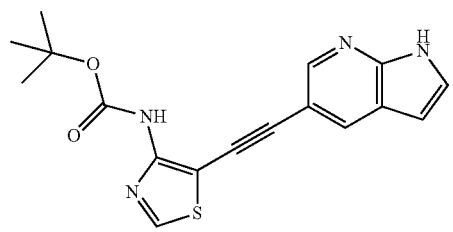 [SMILES: CC(C)(C)OC(=O)Nc1ncsc1C#Cc1cnc2[nH]ccc2c1] |
| "A22" | 5-(1H-Pyrrolo[2,3-b]pyridin-5-ylethynyl)thiazol-4-ylamine 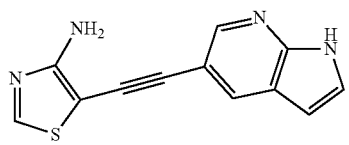 |
| "A24" | tert-Butyl N-(2-pyridin-4-yl-5-iodo-1,3-thiazol-4-yl)carbamate 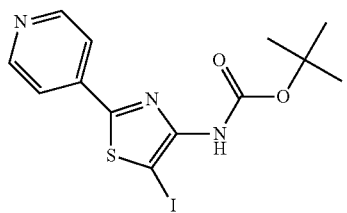 [SMILES: CC(C)(C)OC(=O)Nc1nc(-c2ccncc2)sc1I] |
| "A25" | tert-Butyl [5-(3-morpholin-4-ylprop-1-ynyl)-2-pyridin-4-ylthiazol-4-yl]carbamate 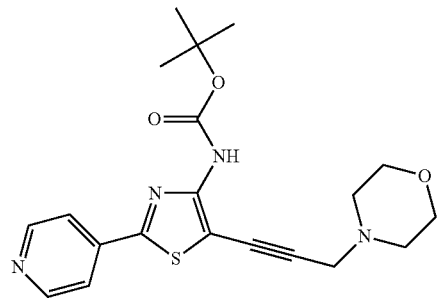 [SMILES: CC(C)(C)OC(=O)Nc1nc(-c2ccncc2)sc1C#CCN1CCOCC1] |

| No. | Name and/or structure |
|---|---|
| "A26" | tert-Butyl {5-[3-(1,3-dioxo-1,3-dihydroisoindol-2-yl)prop-1-ynyl]thiazol-4-yl}-carbamate 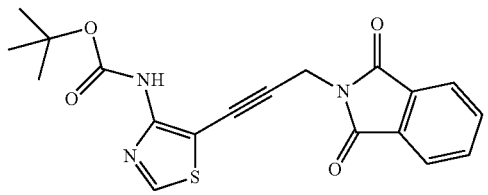 [SMILES: CC(C)(C)OC(=O)Nc1ncsc1C#CCN1C(=O)c2ccccc2C1=O] |
| "A27" | 3-(4-Aminothiazol-5-ylethynyl)phenol 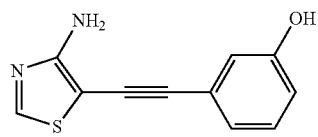 |
| "A28" | tert-Butyl [2-(2-aminopyridin-3-yl)-5-(4-fluorophenylethynyl)thiazol-4-yl]carbamate 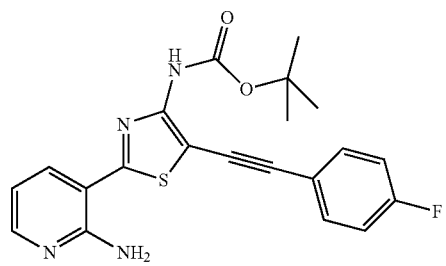 [SMILES: CC(C)(C)OC(=O)Nc1nc(-c2cccnc2N)sc1C#Cc1ccc(F)cc1] |
| "A29a" | tert-Butyl N-{2-chloro-5-[2-(4-fluorophenyl)ethynyl]-1,3-thiazol-4-yl}carbamate 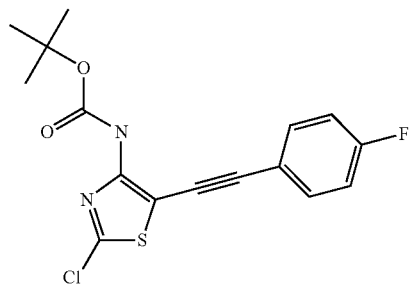 [SMILES: CC(C)(C)OC(=O)Nc1nc(Cl)sc1C#Cc1ccc(F)cc1] |
| "A29" | tert-Butyl N-[2-(2-aminopyrimidin-5-yl)-5-[2-(4-fluorophenyl)ethynyl]-1,3-thiazol-4-yl]carbamate 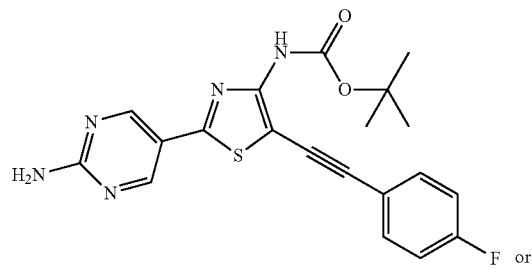 [SMILES: CC(C)(C)OC(=O)Nc1nc(-c2cnc(N)nc2)sc1C#Cc1ccc(F)cc1 ; "or"] or |

| No. | Name and/or structure |
|---|---|
| "A30" | 3-[5-(4-Fluorophenyl)-4H-pyrrolo[2,3-d]thiazol-2-yl]pyridin-2-ylamine |

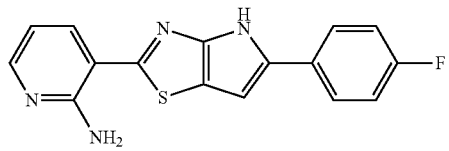 [SMILES: Nc1ncccc1-c1nc2[nH]c(-c3ccc(F)cc3)cc2s1]

or a pharmaceutically acceptable salt, tautomer or stereoisomers thereof.

5. A pharmaceutical composition comprising a compound of claim 4, and one or more pharmaceutically acceptable excipients and/or adjuvants.

6. A compound according to claim 4, or a pharmaceutically acceptable salt thereof.

7. A compound according to claim 1, which is one of the following compounds

| | |
|---|---|
| "A31" | 3-[5-(4-Fluorophenyl)-4H-pyrrolo[2,3-d]thiazol-2-yl]-5-(1-piperidin-4-yl-1H-pyrazol-4-yl)pyridin-2-ylamine |
| "A32" | 6-(4,4-Dimethylpent-2-ynyl)-4H-pyrrolo[2,3-d]thiazole |
| "A33" | Methyl 2-tert-butyl-3-(4H-pyrrolo[2,3-d]thiazol-6-ylmethyl)-1H-indole-5-carboxylate |
| "A34" | 2-tert-Butyl-3-(4H-pyrrolo[2,3-d]thiazol-6-ylmethyl)-1H-pyrrolo[2,3-b]pyridine |

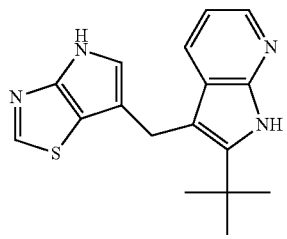 [SMILES: CC(C)(C)c1[nH]c2ncccc2c1Cc1c[nH]c2ncsc12]

| | |
|---|---|
| "A59" | Morpholin-4-yl-[3-(4H-pyrrolo[2,3-d]thiazole-6-ylmethyl)-1H-indol-5-yl]methanone |
| "A60" | N-(2-Methoxyethyl)-3-(4H-pyrrolo[2,3-d]thiazole-6-ylmethyl)-1H-indole-5-carboxamide |
| "A61" | N-(4-Fluorobenzyl)-3-(4H-pyrrolo[2,3-d]thiazol-6-ylmethyl)-1H-indole-5-carboxamide |
| "A62" | N-(2-Aminoethyl)-2-[4-(4H-pyrrolo[2,3-d]thiazol-6-ylmethyl)-1,2,3-triazol-1-yl]-acetamide |
| "A63" | 1-Piperazin-1-yl-2-[4-(4H-pyrrolo[2,3-d]thiazol-6-ylmethyl)-1,2,3-triazol-1-yl]-ethanone |
| "A64" | N-(Piperidin-4-yl)-2-[4-(4H-pyrrolo[2,3-d]thiazol-6-ylmethyl)-1,2,3-triazol-1-yl]-acetamide |
| "A65" | 6-(1-Pyridin-3-ylmethyl-1H-1,2,3-triazol-4-ylmethyl) 4H-pyrrolo [2,3-d]thiazole |
| "A66" | 6-(1-Pyridin-4-ylmethyl-1H-1,2,3-triazol-4-ylmethyl) 4H-pyrrolo [2,3-d]thiazole |
| "A67" | 6-Benzyl-2-(5-(1-methyl-1H-pyrazol-4-yl)pyridin-3-yl)-4H-pyrrolo[2,3-d]thiazole |
| "A68" | 6-Benzyl-2-(5-(1H-pyrazol-4-yl)pyridin-3-yl)-4H-pyrrolo[2,3-d]thiazole |
| "A69" | 6-Benzyl-2-(5-(4-fluorophenyl)pyridin-3-yl)-4H-pyrrolo[2,3-d]thiazole |
| "A70" | 6-(5-Methanesulfonylthiophen-2ylmethyl)-4H-pyrrolo[2,3-d]thiazole |
| "A71" | 6-[1-(2-Morpholin-4-ylethyl)-1H-1,2,3-triazol-4-ylmethyl] 4H-pyrrolo[2,3-d]thiazole or |
| "A72" | 6-Benzyl-2-{5-[1-((E)-3-phenylallyl)-1H-pyrazol-4-yl]pyridin-3-yl}-4H-pyrrolo-[2,3-d]thiazole | or a pharmaceutically acceptable salt, tautomer or stereoisomers thereof.

8. A compound according to claim 1, which is one of the following compounds

| | |
|---|---|
| "A35" | 6-(3,5-Difluorobenzyl)-4H-pyrrolo[2,3-d]thiazole |
| "A36" | 6-(4-Methoxybenzyl)-4H-pyrrolo[2,3-d]thiazole |
| "A37" | 6-(4-Bromobenzyl)-4H-pyrrolo[2,3-d]thiazole |
| "A38" | 6-(4-Isopropylbenzyl)-4H-pyrrolo[2,3-d]thiazole |
| "A39" | 6-(4-Bromo-2-fluorobenzyl)-4H-pyrrolo[2,3-d]thiazole |
| "A40" | 6-(4-tert-Butylbenzyl)-4H-pyrrolo[2,3-d]thiazole |
| "A41" | 6-(2-Chlorobenzyl)-4H-pyrrolo[2,3-d]thiazole |
| "A42" | 6-(4-Fluorobenzyl)-4H-pyrrolo[2,3-d]thiazole |
| "A43" | 6-(3-Fluorobenzyl)-4H-pyrrolo[2,3-d]thiazole |
| "A44" | 6-(2,3-Difluorobenzyl)-4H-pyrrolo[2,3-d]thiazole |
| "A45" | 6-(2,4-Difluorobenzyl)-4H-pyrrolo[2,3-d]thiazole |
| "A46" | 6-(2,5-Difluorobenzyl)-4H-pyrrolo[2,3-d]thiazole |
| "A47" | 6-(3,4-Difluorobenzyl)-4H-pyrrolo[2,3-d]thiazole |
| "A49" | 6-(3-Chlorobenzyl)-4H-pyrrolo[2,3-d]thiazole |
| "A50" | 6-(3,4-Dichlorobenzyl)-4H-pyrrolo[2,3-d]thiazole |
| "A56" | 6-Benzyl-2-(1H-pyrazol-4-yl)-4H-pyrrolo[2,3-d]thiazole or |
| "A58" | 6-Benzyl-2-pyrimidin-5-yl-4H-pyrrolo[2,3-d]thiazole | or a pharmaceutically acceptable salt, tautomer or stereoisomers thereof.

9. A compound according to claim 1, which is one of the following compounds

| | |
|---|---|
| "A48" | 6-(6-Chloropyridin-3-ylmethyl)-4H-pyrrolo[2,3-d]thiazole |
| "A52" | 6-Benzyl-2-(1-methyl-1H-pyrazol-4-yl)-4H-pyrrolo-[2,3-d]thiazole |
| "A53" | 5-(6-Benzyl-4H-pyrrolo[2,3-d]thiazol-2-yl)pyridin-2-ylamine |
| "A54" | 6-Prop-2-ynyl-4H-pyrrolo[2,3-d]thiazole or |
| "A55" | 3-(6-Benzyl-4H-pyrrolo[2,3-d]thiazol-2-yl)pyridin-2-ylamine | or a pharmaceutically acceptable salt, tautomer or stereoisomers thereof.

10. A compound according to claim 1, which is one of the following compounds

| | |
|---|---|
| "A51" | 6-Benzyl-2-pyridin-3-yl-4H-pyrrolo[2,3-d]thiazole | or a pharmaceutically acceptable salt, tautomer or stereoisomers thereof.

11. A compound according to claim 1, which is one of the following compounds

| | |
|---|---|
| "A57" | 6-Benzyl-2-(5-bromopyridin-3-yl)-4H-pyrrolo[2,3-d]thiazole | or a pharmaceutically acceptable salt, tautomer or stereoisomers thereof.

12. A compound according to claim 4, which is one of the following compounds

| No. | Name and/or structure |
|---|---|
| "A1" | 5-(4-Fluorophenyl)-4H-pyrrolo[2,3-d]-1,3-thiazole |
| "A2" | 5-Benzyl-4H-pyrrolo[2,3-d]thiazole |
| "A4" | 3-(4H-Pyrrolo[2,3-d]thiazol-5-yl)phenylamine |
| "A5" | Benzyl-[4-(4H-pyrrolo[2,3-d]thiazol-5-yl)pyridin-2-yl]amine |
| "A6" | Benzyl-[3-(4H-pyrrolo[2,3-d]thiazol-5-yl)phenyl]amine |
| "A7" | 6-Benzyl-4H-pyrrolo[2,3-d]thiazole |
| "A8" | 6-Benzyl-2-pyridin-4-yl-4H-pyrrolo[2,3-d]thiazole |

-continued

| No. | Name and/or structure |
|---|---|
| "A9" | 4-(4H-Pyrrolo[2,3-d]thiazol-5-yl)pyridin-2-ylamine |
| "A10" | 2-Chloro-5-(4-fluorophenyl)-4H-pyrrolo[2,3-d]thiazole |
| "A11" | 5-(4-Fluorophenyl)-2-(4-fluorophenylethynyl)-4H-pyrrolo[2,3-d]thiazole |
| "A12" | 5-(4-Fluorophenyl)-2-morpholin-4-yl-4H-pyrrolo[2,3-d]thiazole |
| "A13" | 5-(4-Fluorophenyl)-2-(4-pyridin-4-ylmethylpiperazin-1-yl)-4H-pyrrolo[2,3-d]thiazole |
| "A14" | 5-[5-(4-Fluorophenyl)-4H-pyrrolo[2,3-d]thiazol-2-yl]pyrimidin-2-ylamine |
| "A15" | tert-Butyl N-{5-[2-(4-fluorophenyl)ethynyl]-1,3-thiazol-4-yl}carbamate |

-continued

| No. | Name and/or structure |
|---|---|
| "A16" | tert-Butyl [5-(3-phenylprop-1-ynyl)thiazol-4-yl]carbamate |
| "A17" | tert-Butyl (5-triethylsilanylethynylthiazol-4-yl)carbamate |
| "A18" | tert-Butyl [5-(3-aminophenylethynyl)thiazol-4-yl]carbamate |
| "A19" | tert-Butyl [5-(3-benzylaminophenylethynyl)thiazol-4-yl]carbamate |
| "A20" | tert-Butyl [5-(2-benzylaminopyridin-4-ylethynyl)thiazol-4-yl]carbamate |

-continued

| No. | Name and/or structure |
|---|---|
| "A21" | tert-Butyl [5-(1H-pyrrolo[2,3-b]pyridin-5-ylethynyl)thiazol-4-yl]carbamate 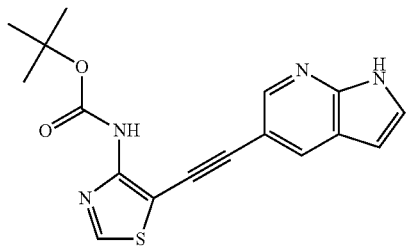 [SMILES: CC(C)(C)OC(=O)Nc1ncsc1C#Cc1cnc2[nH]ccc2c1] |
| "A22" | 5-(1H-Pyrrolo[2,3-b]pyridin-5-ylethynyl)thiazol-4-ylamine 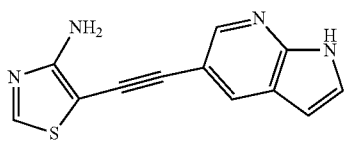 [SMILES: Nc1ncsc1C#Cc1cnc2[nH]ccc2c1] |
| "A25" | tert-Butyl [5-(3-morpholin-4-ylprop-1-ynyl)-2-pyridin-4-ylthiazol-4-yl]carbamate 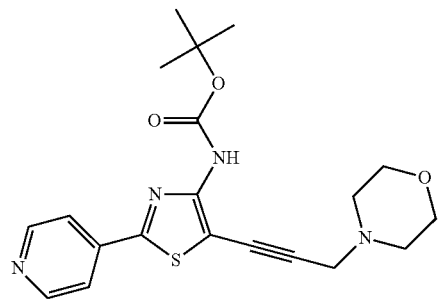 [SMILES: CC(C)(C)OC(=O)Nc1nc(-c2ccncc2)sc1C#CCN1CCOCC1] |
| "A26" | tert-Butyl {5-[3-(1,3-dioxo-1,3-dihydroisoindol-2-yl)prop-1-ynyl]thiazol-4-yl}-carbamate 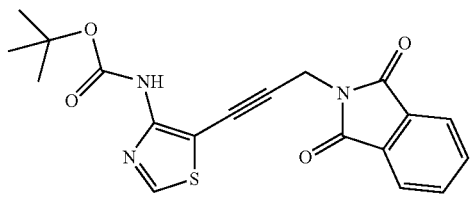 [SMILES: CC(C)(C)OC(=O)Nc1ncsc1C#CCN1C(=O)c2ccccc2C1=O] |
| "A27" | 3-(4-Aminothiazol-5-ylethynyl)phenol 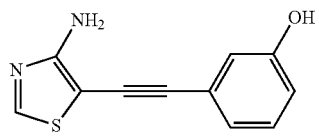 |
| "A28" | tert-Butyl [2-(2-aminopyridin-3-yl)-5-(4-fluorophenylethynyl)thiazol-4-yl]carbamate 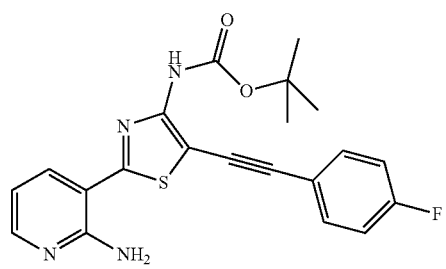 [SMILES: CC(C)(C)OC(=O)Nc1nc(-c2cccnc2N)sc1C#Cc1ccc(F)cc1] |

| No. | Name and/or structure |
|---|---|
| "A29a" | tert-Butyl N-{2-chloro-5-[2-(4-fluorophenyl)ethynyl]-1,3-thiazol-4-yl}carbamate |

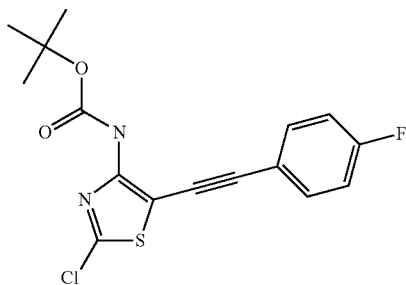 [SMILES: CC(C)(C)OC(=O)Nc1nc(Cl)sc1C#Cc1ccc(F)cc1]

| | |
|---|---|
| "A29" | tert-Butyl N-[2-(2-aminopyrimidin-5-yl)-5-[2-(4-fluorophenyl)ethynyl]-1,3-thiazol-4-yl]carbamate |

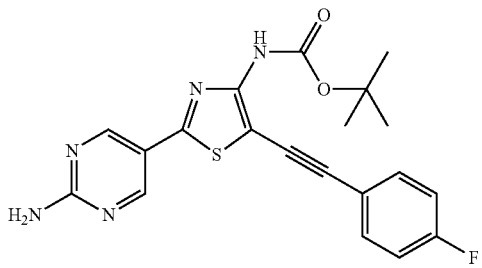 [SMILES: CC(C)(C)OC(=O)Nc1nc(-c2cnc(N)nc2)sc1C#Cc1ccc(F)cc1]

| | |
|---|---|
| "A30" | 3-[5-(4-Fluorophenyl)-4H-pyrrolo[2,3-d]thiazol-2-yl]pyridin-2-ylamine |

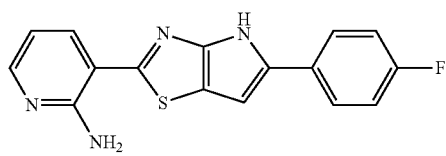

or a pharmaceutically acceptable salt, tautomer or stereoisomers thereof.

13. A compound according to claim 4, which is one of the following compounds

| No. | Name and/or structure |
|---|---|
| "2" | tert-Butyl N-(5-iodo-1,3-thiazol-4-yl)carbamate |
| "A1" | 5-(4-Fluorophenyl)-4H-pyrrolo[2,3-d]-1,3-thiazole |

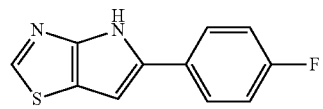 [SMILES: Fc1ccc(-c2cc3scnc3[nH]2)cc1]

| | |
|---|---|
| "A2" | 5-Benzyl-4H-pyrrolo[2,3-d]thiazole |
| "A5" | Benzyl-[4-(4H-pyrrolo[2,3-d]thiazol-5-yl)pyridin-2-yl]amine |

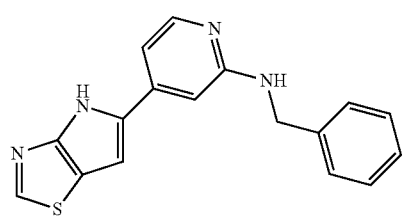 [SMILES: c1ccc(CNc2cc(-c3cc4scnc4[nH]3)ccn2)cc1]

| No. | Name and/or structure |
|---|---|
| "A6" | Benzyl-[3-(4H-pyrrolo[2,3-d]thiazol-5-yl)phenyl]amine |
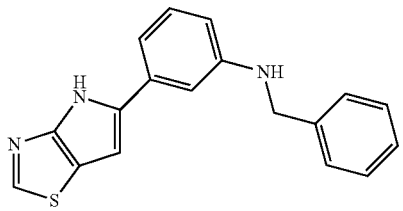 [SMILES: c1ccc(CNc2cccc(-c3cc4scnc4[nH]3)c2)cc1]
| | |
|---|---|
| "A7" | 6-Benzyl-4H-pyrrolo[2,3-d]thiazole |
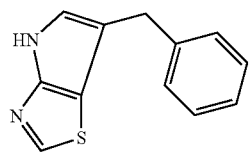 [SMILES: c1ccc(Cc2c[nH]c3ncsc23)cc1]
| | |
|---|---|
| "A8" | 6-Benzyl-2-pyridin-4-yl-4H-pyrrolo[2,3-d]thiazole |
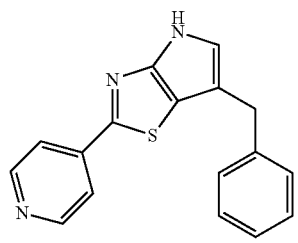 [SMILES: c1ccc(Cc2c[nH]c3nc(-c4ccncc4)sc23)cc1]
| | |
|---|---|
| "A9" | 4-(4H-Pyrrolo[2,3-d]thiazol-5-yl)pyridin-2-ylamine |
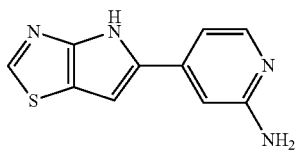
| | |
|---|---|
| "A10" | 2-Chloro-5-(4-fluorophenyl)-4H-pyrrolo[2,3-d]thiazole |
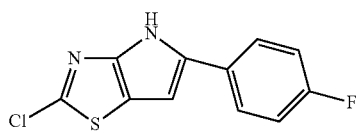 [SMILES: Fc1ccc(-c2cc3sc(Cl)nc3[nH]2)cc1]
| | |
|---|---|
| "A11" | 5-(4-Fluorophenyl)-2-(4-fluorophenylethynyl)-4H-pyrrolo[2,3-d]thiazole |
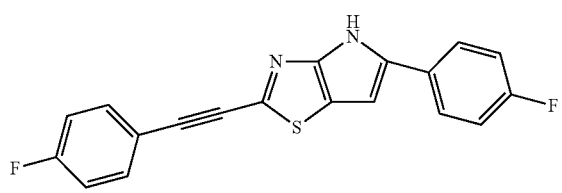 [SMILES: Fc1ccc(C#Cc2nc3[nH]c(-c4ccc(F)cc4)cc3s2)cc1]
| | |
|---|---|
| "A12" | 5-(4-Fluorophenyl)-2-morpholin-4-yl-4H-pyrrolo[2,3-d]thiazole |
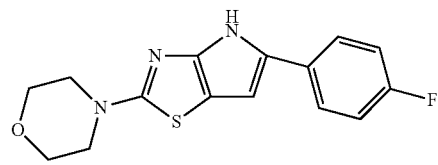 [SMILES: Fc1ccc(-c2cc3sc(N4CCOCC4)nc3[nH]2)cc1]

-continued

| No. | Name and/or structure |
|---|---|
| "A13" | 5-(4-Fluorophenyl)-2-(4-pyridin-4-ylmethylpiperazin-1-yl)-4H-pyrrolo[2,3-d]thiazole |

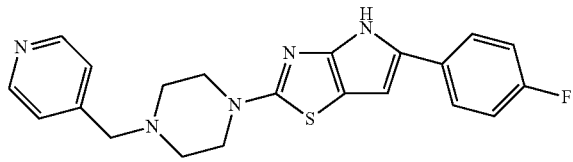 [SMILES: Fc1ccc(-c2cc3sc(N4CCN(Cc5ccncc5)CC4)nc3[nH]2)cc1]

| | |
|---|---|
| "A14" | 5-[5-(4-Fluorophenyl)-4H-pyrrolo[2,3-d]thiazol-2-yl]pyrimidin-2-ylamine |

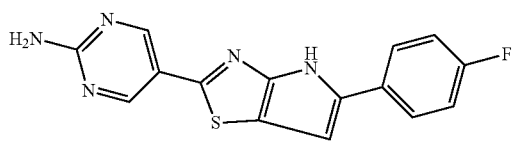 [SMILES: Nc1ncc(-c2nc3[nH]c(-c4ccc(F)cc4)cc3s2)cn1]

| | |
|---|---|
| "A15" | tert-Butyl N-{5-[2-(4-fluorophenyl)ethynyl]-1,3-thiazol-4-yl}carbamate |

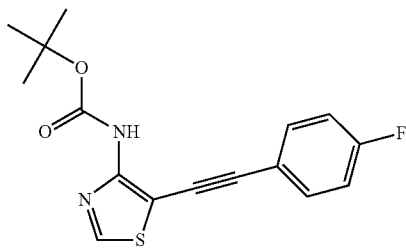 [SMILES: CC(C)(C)OC(=O)Nc1ncsc1C#Cc1ccc(F)cc1]

| | |
|---|---|
| "A16" | tert-Butyl [5-(3-phenylprop-1-ynyl)thiazol-4-yl]carbamate |

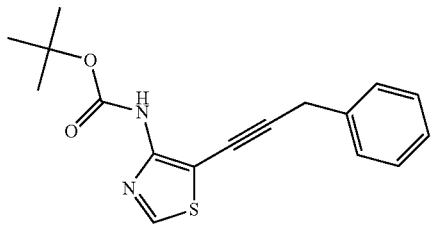 [SMILES: CC(C)(C)OC(=O)Nc1ncsc1C#CCc1ccccc1]

| | |
|---|---|
| "A17" | tert-Butyl (5-triethylsilanylethynylthiazol-4-yl)carbamate |

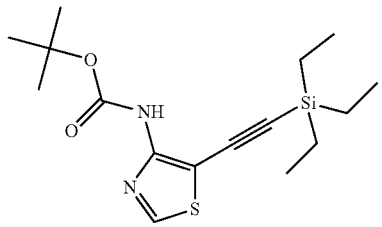 [SMILES: CC[Si](C#Cc1scnc1NC(=O)OC(C)(C)C)(CC)CC]

| | |
|---|---|
| "A18" | tert-Butyl [5-(3-aminophenylethynyl)thiazol-4-yl]carbamate |

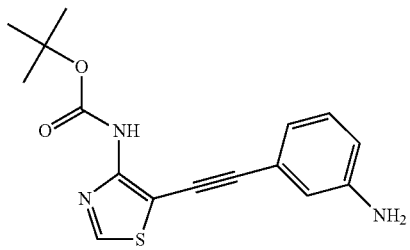 [SMILES: CC(C)(C)OC(=O)Nc1ncsc1C#Cc1cccc(N)c1]

-continued
| No. | Name and/or structure |
|---|---|
| "A19" | tert-Butyl [5-(3-benzylaminophenylethynyl)thiazol-4-yl]carbamate 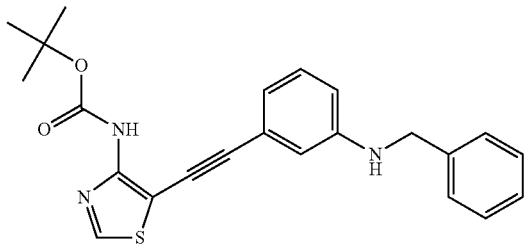 [SMILES: CC(C)(C)OC(=O)Nc1ncsc1C#Cc1cccc(NCc2ccccc2)c1] |
| "A20" | tert-Butyl [5-(2-benzylaminopyridin-4-ylethynyl)thiazol-4-yl]carbamate 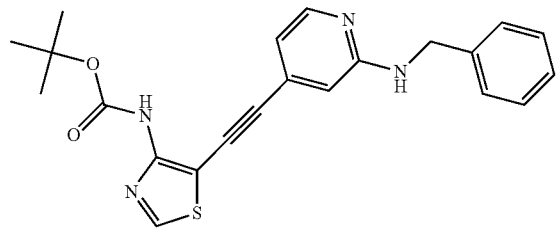 [SMILES: CC(C)(C)OC(=O)Nc1ncsc1C#Cc1ccnc(NCc2ccccc2)c1] |
| "A21" | tert-Butyl [5-(1H-pyrrolo[2,3-b]pyridin-5-ylethynyl)thiazol-4-yl]carbamate 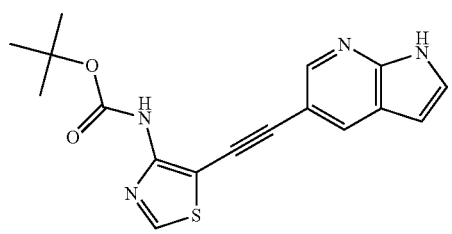 [SMILES: CC(C)(C)OC(=O)Nc1ncsc1C#Cc1cnc2[nH]ccc2c1] |
| "A22" | 5-(1H-Pyrrolo[2,3-b]pyridin-5-ylethynyl)thiazol-4-ylamine 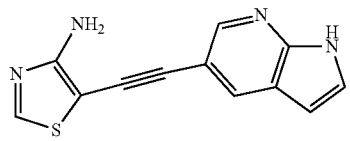 [SMILES: Nc1ncsc1C#Cc1cnc2[nH]ccc2c1] |
| "A24" | tert-Butyl N-(2-pyridin-4-yl-5-iodo-1,3-thiazol-4-yl)carbamate 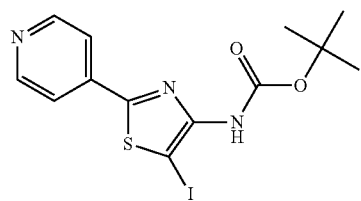 [SMILES: CC(C)(C)OC(=O)Nc1nc(-c2ccncc2)sc1I] |

| No. | Name and/or structure |
|---|---|
| "A25" | tert-Butyl [5-(3-morpholin-4-ylprop-1-ynyl)-2-pyridin-4-ylthiazol-4-yl]carbamate 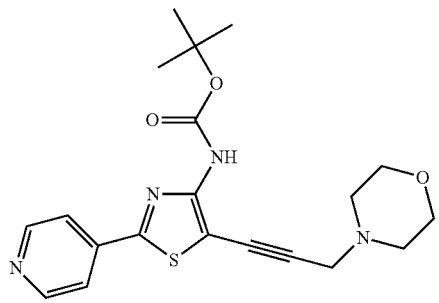 [SMILES: CC(C)(C)OC(=O)Nc1nc(-c2ccncc2)sc1C#CCN1CCOCC1] |
| "A26" | tert-Butyl {5-[3-(1,3-dioxo-1,3-dihydroisoindol-2-yl)prop-1-ynyl]thiazol-4-yl}-carbamate 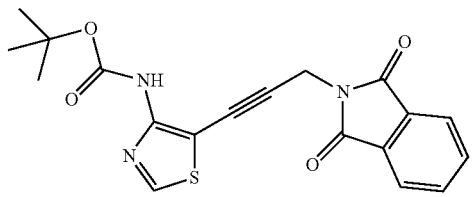 [SMILES: CC(C)(C)OC(=O)Nc1ncsc1C#CCN1C(=O)c2ccccc2C1=O] |
| "A27" | 3-(4-Aminothiazol-5-ylethynyl)phenol 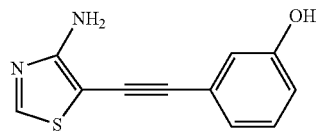 [SMILES: Nc1ncsc1C#Cc1cccc(O)c1] |
| "A28" | tert-Butyl [2-(2-aminopyridin-3-yl)-5-(4-fluorophenylethynyl)thiazol-4-yl]carbamate 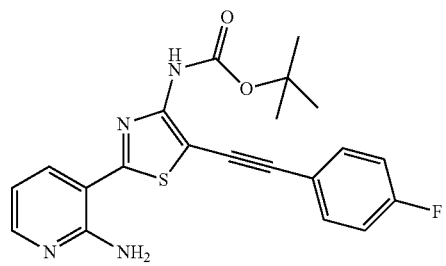 [SMILES: CC(C)(C)OC(=O)Nc1nc(-c2cccnc2N)sc1C#Cc1ccc(F)cc1] |
| "A29a" | tert-Butyl N-{2-chloro-5-[2-(4-fluorophenyl)ethynyl]-1,3-thiazol-4-yl}carbamate 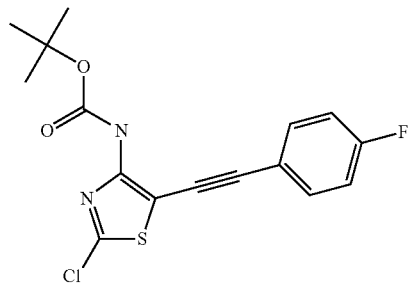 [SMILES: CC(C)(C)OC(=O)Nc1nc(Cl)sc1C#Cc1ccc(F)cc1] |

| No. | Name and/or structure |
|---|---|
| "A29" | tert-Butyl N-[2-(2-aminopyrimidin-5-yl)-5-[2-(4-fluorophenyl)ethynyl]-1,3-thiazol-4-yl]carbamate 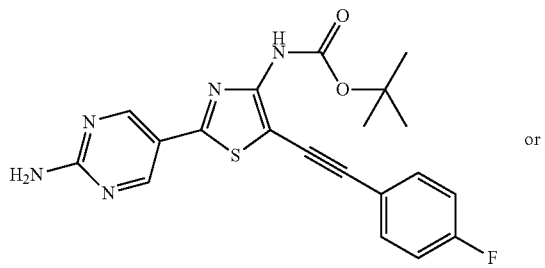 [SMILES: CC(C)(C)OC(=O)Nc1nc(-c2cnc(N)nc2)sc1C#Cc1ccc(F)cc1 ; "or"] or |
| "A30" | 3-[5-(4-Fluorophenyl)-4H-pyrrolo[2,3-d]thiazol-2-yl]pyridin-2-ylamine 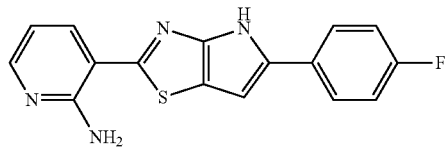 |
or a pharmaceutically acceptable salt, tautomer or stereoisomers thereof.
* * * * *

UNITED STATES PATENT AND TRADEMARK OFFICE
CERTIFICATE OF CORRECTION

PATENT NO. : 8,703,961 B2
APPLICATION NO. : 13/515537
DATED : April 22, 2014
INVENTOR(S) : Timo Heinrich et al.

Page 1 of 1

It is certified that error appears in the above-identified patent and that said Letters Patent is hereby corrected as shown below:

In the Claims

Claim 4, Column 74, structure ("A6"), reads,

" 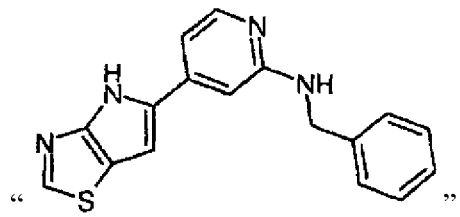 "

should read,

-- 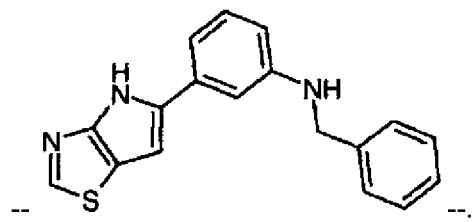 --.

Signed and Sealed this
Ninth Day of September, 2014

Michelle K. Lee
*Deputy Director of the United States Patent and Trademark Office*